United States Patent [19]

Haselkorn et al.

[11] Patent Number: 5,539,092
[45] Date of Patent: Jul. 23, 1996

[54] CYANOBACTERIAL AND PLANT ACETYL-COA CARBOXYLASE

[75] Inventors: Robert Haselkorn; Piotr Gornicki, both of Chicago, Ill.

[73] Assignee: ARCH Development Corporation, Chicago, Ill.

[21] Appl. No.: 956,700

[22] Filed: Oct. 2, 1992

[51] Int. Cl.⁶ .................................................. C07H 21/04
[52] U.S. Cl. ...................... 536/23.2; 536/23.1; 536/23.6; 536/23.7; 935/14
[58] Field of Search .......................... 800/205; 536/23.2, 536/23.6, 23.7, 24.1; 435/7.4, 7.6, 29, 69.1, 172.3, 240.4, 252.3, 257, 320.1, 946; 935/9, 10, 14, 64, 66, 67, 78, 79, 90; 530/300, 370

[56] References Cited

U.S. PATENT DOCUMENTS

| | | | |
|---|---|---|---|
| 4,535,060 | 8/1985 | Comai | 435/172.3 |
| 4,757,011 | 7/1988 | Chaleff et al. | 435/172.1 |
| 4,769,061 | 9/1988 | Comai | 71/86 |
| 4,940,835 | 7/1990 | Shah et al. | 800/205 |
| 4,971,908 | 11/1990 | Kishore et al. | 435/172.1 |

FOREIGN PATENT DOCUMENTS

| | | |
|---|---|---|
| 2048040 | 1/1992 | Canada . |
| 0469810 | 2/1992 | European Pat. Off. . |
| WO93/11243 | 6/1993 | WIPO . |

OTHER PUBLICATIONS

Alban et al., "Purification and characterization of 3-methylcrotonyl-coenzyme A carboxylase from higher plant mitochondria," *Plant. Physiol.*, 102:957–965, 1993.

Best, E. A., and Knauf, V. C., "Organization and nucleotide sequence of the genes encoding the biotin carboxyl carrier protein and biotin cargboxylase protein of Pseudomonas aeruginosa acetyl coenzyme A carboxylase," *J. Bacteriol.*, 175:6881–6889, 1993.

Bettey et al., "Purification and characterization of acetyl–coA carboxylase from developing pea embryos," *J. Plant. Physiol.*, 140:513–520, 1992.

Browner et al., "Sequence analysis, biogenesis and mitochonoriald import of the alpha–subunit of rat liver propionyl–CoA carboxylase," *J. Biol. Chem.*, 264:12680–12685.

Chen et al., "Purification and characterization of 3-methylocrotonyl–CoA carboxylase from somatic embryos of Dacuscarota.", *Arch. Biochem. Biophys.*, 305:103–109, 1993.

Chirala, S. S., "Coordinated regulation and inositol-mediated and fatty acid-mediaed repression of fatty acid synthase genes in Saccharomyces cerevisiae," *proc. Natl. Acad. Sci. USA*, 89:10232–10236, 1992.

Egin–Buhler, B. and Ebel, J., "Comparison of acetyl–CoA carboxylase from parsley cell culture and from wheat germ," *Eur J. Biochem.*, 133:335–339, 1983.

Egli et al., "Characterization of maize acetyl–coenzyme A carboxylase," *Plant. Physiol.*, 101:499–506, 1993.

Fall, R. R., "Analysis of microbiol biotin proteins," *Meth. Enzymol.*, 62:390–398, 1979.

Gornicki, P. and Haselkorn, R., "Wheat acetyl–CoA carboxylase," *Plant Mol. Biol.* 22:547–552, 1993.

Hardie et al., "The AMP–activated protein kinase: A multisubstrate regulator of lipid metabolism," *Trends in Biochem. Sci.*, 14:20–23, 1989.

(List continued on next page.)

*Primary Examiner*—Bruce R. Campell
*Attorney, Agent, or Firm*—Arnold, White & Durkee

[57] ABSTRACT

The present invention provides isolated and purified polynucleotides that encode plant and cyanobacterial polypeptides that participate in the carboxylation of acetyl-CoA. Isolated cyanobacterial and plant polypeptides that catalyze acetyl-CoA carboxylation are also provided. Processes for altering acetyl-CoA carboxylation, increasing herbicide resistance of plants and identifying herbicide resistant variants of acetyl-CoA carboxylase are also provided.

9 Claims, 16 Drawing Sheets

OTHER PUBLICATIONS

HaBlacher et al., "Acetyl–CoA carboxylase from yeast is an essential enzyme and is regulated by factors that control phospholipid metabolism," *J. Biol. Chem.*, 268:10946–10952, 1993.

Holt et al., "Mechanisms and agronomic aspects of herbicide resistance," *Annu. Rev. Plant. Physiol. Plant Mol. Biol.*, 44:203–229, 1993.

Li, S–1 and Cronan, J. E., "Growth rate regulation of *Escherichiacoli* acetyl coenzyme A carboxylase, which catalyzes the first commited step of lipid biosynthesis", *J. Bacteriol.*, 175:332–340, 1993.

Marshall et al., "Allelic mutations in acetyl–coenzyme A carboxylse confer herbicide tolerance in maiz," *Theor. Appl. Genet.*, 83:435–442, 1992.

Nikolau et al., "Acetyl–coenzyme A carboxylase in maize leaves," *Arch. Biochem. and Biophys.*, 211:605–612, 1981.

Nikolau et al., "Tissue distribution of ACC in leaves," *Plant Physiol.* 75:895–901, 1984.

Post–Beittenmiller et al., "Regulation of plant fatty acid biosynthesis," *Plant. Physiol.*, 100:923–930, 1992.

Reitzel, L. and Nielsen, N. C., "Acetyl–coenzyme A carboxylase during development of plastides in wild–type and mutant barley seedlings," *Eur. J. Biochem.*, 65:131–138, 1976.

Rendina et al., "Kinetic characterization, stereoselectivity and species selectivity of the inhibition of plant acetyl–CoA carboxylase by the aryloxyphenoxypropionic acid grass herbicides," *Arch. Biochem. Biophys.*, 265:219–225, 1988.

Roessler, P. G., and Ohlrogge, J. B., "Cloning and characterization of the gene that encodes acetyl–coenzyme A carboxylase in the alga *Cyclotellacryptica,*" *J. Biol. Chem.*, 268:19254–19259, 1993.

Sasaki et al., "Chloroplast–encloded protein as a subunit of acetyl–CoA carboxylase in pea plant," *J. Biol. Chem.*, 268:25118–25123, 1993.

Shenoy et al., "The importance of methionine residues for the catalysis of the biotin enzyme, transcarboxylase," *J. Biol. Chem.*, 18407–18412, 1992.

Slabas, A. R., and T. Fawcett, "The biochemistry and molecular biology of plant lipid biosynthesis," *Plant. Mol. Biol.*, 19:169–191, 1992.

Somers et al., "Expression of the Accl gene–encoded acetyl–coenzyme A carboxylase in developing maize (Zea mays L.) kernels," *Plant Physiol,* 101:1097–1101, 1993.

Somerville, A. and Browse, J., "Plant lipids: metabolism, mutants, and membranes," *Science,* 252:80–87, 1991.

Toh et al, "Molecular evolution of biotin–dependent carboxylases," *Eur. J. Biochem.*, 215:687–696, 1993.

Turnham, E., and Northcote, D. H., "Changes in the activity of acetyl–CoA carboxylase during rape–see formation," *Biochem. J.*, 212:223–229, 1983.

Witters, L. A., and Kemp, B. E., "Insulin activation of acetyl–CoA carboxylase by inhibition of the 5'–AMP–activated protein kinase," *J. Biol. Chem.*, 267:2864–2867, 1992.

Wood, H. G., and Barden, R. E., "Biotin enzymes," *Ann. Rev. Biochem.*, 46:385–413, 1977.

Wurtele, E. S., and Nikolau, B. J., "Differential accumulation of biotin enzymes during carrot somatic embryogenesis," *Plant. Physiol.* 99:1699–1703, 1992.

K. A. Walker et al (1988) Biochem. J. 254:307–310.

N C Nielsen et al (1979) Arch Biochem Biophys 192:446–456.

T A Brown (1990) Gene Cloning, An Introduction, 2nd edition, pp. 153–177.

Aebersold et. al, Internal amino acid sequence analysis of proteins separated by one or two–dimensional gel electrophoresis after in situ protease, *Proc. Natl. Acad. Sci. USA* 84:6970–6974, 1987.

Al–Feel et. al, Cloning of the yeast FAS3 gene and primary structure of yeast acetyl–CoA carboxylase, *Proc. Natl. Acad. Sci. USA,* 89:4534–4538, 1992.

Alix, Laboratory Methods; A Rapid Procedure for Cloning Genes from λLibraries by Complementation of *E. coli* Defective Mutants: Application to the fabE Region of the E. coli Chromosome, *DNA,* 8:(10)779–789, 1989.

Bai et. al, Analysis of the biotin–binding site on acetyl–CoA carboxylase from rat, *Eur. J. Biochem.* 182:239–245, 1989.

Buhler et. al, Improved Purification and Further Characterization of Acetyl–CoA Carboxylase from Cultured Cells of Parsley (*Petroselinum hortense*) *Eur. J. Biochem.* 133:335–339, 1983.

Craig et. al, Genetic engineering of micro–algae, Micro–Algal Biotechnology Cambridge University Press, 16:415–455, 1988.

Eichholtz et. al, Expression of Mouse Dihydrofolate Reductase Gene Confers Methotrexate Resistance in Transgenic Petunia Plants, *Somatic Cell and Molecular Genetics,* 13:(1)67–76, 1987.

Evenson et. al, Purification and Characterization of Acetyl–CoA Carboxylase from Diclofop–Resistant and Susceptible Italian Ryegrass (*Lolium Multiflorum*), *Plant Physiol,* 99(1 Suppl):59, Abstract #351, 1992.

Golden, Genetic Engineering of the cyanobacterial Chromosome, *J. Bacteriol,* 165:(964)215–231, 1986.

Guchhait et. al, Acetyl Coenzyme A Carboxylase System of *Escherichia coli, J. Biol. Chem.* 249:(20)6633–6645, 1974.

Harwood, Fatty Acid Metabolism, *Ann. Rev. Plant Physiol. Plant Mol. Biol.,* 39:101–138, 1988.

Harwood, Medium and Long–Chain Fatty Acid Synthesis in, The Metabolism, Structure, and Function of Plant Lipids, Edited by: Stumpf et. al, 465–472.

Haymerle et. al, Efficient construction of cDNA libraries in plastid expression vectors using an adaptor strategy, *Nucleic Acids Research,* 14:(21)8615–8624, 1986.

Jaye et. al, Isolation of a human anti–haemophilic factor IX cDNA clone using a unique 52–base synthetic oligonucleotide probe deduced from the amino acid sequence of bovine factor IX, *Nucleic Acids Research* 11:(8)2325–2335, 1983.

Knowles, The Mechanism of Biotin–Dependent Enzymes, *Annu. Rev. Biochem.* 58:195–221, 1989.

Kondo et. al, Acetyl–CoA carboxylase from *Escherichia coli:* Gene organization and nucleotide sequence of the biotin carboxylase subunit, *Proc. Natl. Acad. Sci. USA* 88:9730–9733, 1991.

Lamppa et. al, Structure and Developmental Regulation of a Wheat Gene Encoding the Major Chlorophyll a/b–BInding Polypeptide, *Mole. Cell. Bio.,* 5:(6)1370–1378, 1985.

Li et. al, The Gene Encoding the Biotin Carboxylase Subunit of *Escherichia coli* Acetyl–CoA Carboxylase, *J. Biol. chem.,* 267:(2)855–863, 1992.

Lichtenthaler, Mode of Action of Herbicides Affecting Acety;–CoA Carboxylase and Fatty Acid Biosynthesis, Z. Naturforsch, 45c:521–528, 1990.

Livine et. al, Acetyl–Coenzyme A Carboxylase from the Marine Prymnesiophyte Isochrysis galbana, *Plant Cell Physiol,* 31:(6)851–858, 1990.

Lopez–Casillas et. al, Structure of the coding sequence and primary amino acid sequence of acetyl–coenzyme A carboxylase, *Proc. Natl. Acad. Sci. USA*, 85:5784–5788, 1988.

Lopez–Casillas et. al, Heterogeneity at the 5' End of Rat Acetyl–coenzyme A Carboxylase mRNA, *J. Biological Chem.*, 264:(13)7176–7184, 1989.

Luo et. al, Structural features of the acetyl–CoA carboxylase gene: Mechanisms for the generation of mRNAs with 5' end heterogeneity, *Proc. Natl. Acad. Sci. USA*, 86:4042–4046, 1989.

Muramatsu et. al, Nucleotide sequence of the fabE gene and flanking regions containing a bent DNA sequence of *Escherichia coli, Nucleic Acids Research*, 17:(10)3982, 1989.

Palosarri et. al, Comparison of Acetyl–Coenzyme A Carboxylase From Graminicide–Tolerant and Susceptible Maize Lines, *Plant Physiol.*, 99(1 Suppl):59, Abstract #352, 1992.

Pecker et. al, A single polypeptide catalyzing the conversion of phytoene to ζ–carotene is transcriptionally regulated during tomato fruit ripening, *Proc. Natl. Acad. Sci. USA*, 89:4962–4966, 1992.

Post–Beittenmiller et. al, In Vivo Pools of Free and Acylated Acyl Carrier Proteins in Spinach, *J. Biol. Chem.*, 265:(3)1858–1865, 1991.

Roessler et. al, Characterization of the Gene for Acetyl–CoA Carboxylase From the Alga *Cyclotella Cryptica, Plant Physiol.*, 99(1 Suppl):19 Abstract #113, 1992.

Roessler et. al, Purification and Characterization of Acetyl–CoA Carboxylase from the Diatom *Cyclotella cryptica, Plant Physiol.*, 92:73–78, 1990.

Samols et. al, Evolutionary Conservation among Biotin Enyzmes, *J. Biol. Chem.*, 263;6461–6464, 1988.

Slabas et. al, Rapid Purification of a High Molecular Weight Subunit Polypeptide Form of Rape Seed Acetyl CoA Carboxylase, *Plant Science*, 39:177–182, 1985.

Sedlak, Iowa State Scientists Clone A Key Plant Oil Production Gene, *Genetic Engineering News*, May 1991.

Takai et. al, Primary Structure of Chicken Liver Acetyl–CoA Carboxylase Deduced from cDNA Sequence, *J. Biol. Chem.*, 263:(6)2651–2657, 1988.

Vasil et. al, Herbicide Resistant Fertile Transgenic Wheat Plants Obtained By Microprojectile Bombardment of Regenerable Embryogenic Callus, *Bio/Technology*, 10:667–674, 1992.

Wurtele et. al, Plants Contain Multiple Biotin Enzymes: Discovery of 3–Methylcrotonyl–CoA Carboxylase, Propionyl–CoA Carboxylase and Pyruvate Carboxylase in the Plant Kingdom, *Archives of Biochemistry and Biophysics*, 278:(1)179–186, 1990.Slabas et al., The Biochemistry and Molecular Biology of Plant Lipid Biosynthesis, *Plant Molecular Biology*, 19:169–191, 1992.

Egin–Buehler et al., Comparison of Acetyl Coenzyme A Carboxylases (ED 6.4.1.2 (From Parsley (Petroselinum Hortense) Cell Cultures and Wheat Germ, *Arch Biochem Biophys.*, 203(1):90–100, 1980. (Abstract).

Egli et al., A 223 kDa Subunit of Acetyl–CoA Carboxylase is Encoded by the Acc1 Gene, *Maize Genetics Cooperation Newsletter*, 66:94–95, 1992.

Egli et al., Purification of Maize Leaf Acetyl–CoA Carboxylase, *Maize Genetics Cooperation Newsletter*, 65:95, 1991.

Egli, et al., Purification and Characterization of Maize Acetyl–CoA Carboxylase, *Plant Physiology*, 96(1):92(581), 1991.

Gornicki, et al., Genes for Two Subunits of Acetyl Coenzyme A Carboxylase of *Anabaena* sp. Strain PCC 7120: Biotin Carboxylase and Biotin Carboxyl Carrier Protein, *Journal of Bacteriology*, 175(16):5268–5272, 1993.

Nicolau et al., Use of Streptavidin to Detect Biotin–Containing Proteins in Plants, *Anal Biochem.*, 149(2):448–453, 1985.

International Search Report, Mailed Feb. 22, 1994.

F. Lopez–Casillas et al (1988) Proc Natl Acad Sci 85:5784–5788.

P G Roessler (1990) Plant Physiol 92:73–78.

D A Eichholtz et al (1987) Somatic Cell & Molecular Genetics 13:67–76.

R Craig et al (1988) Genetic Engineering of Microalgae in Borowitzka et al, eds, Micro–algal biotechnology, Cambridge Press.

H Kondo et al (1991) Proc Natl Acad Sci 88:9730–9733.

D Samols et al (1988) J Biol Chem 263:6461–6464.

R B Guchhait et al (1974) J Biol Chem 249:6633–6645.

R H Abersold et al (1987) Proc Natl Acad Sci 84:6970–6974.

M Jaye et al (1983) Nucleic Acids Research 11:2325–2335.

FIG. 1A

```
ATGCTGGCGTTTATATAGAAAAATTTATTGAACGTCCGCGCCACATTGAATTTCAAATTTTGGCTGATAATTACGGCAATGTGATTCACT
 M  L  A  F  I  *                                                                              1980
                 A  G  V  Y  I  E  K  F  I  E  R  P  R  H  I  E  F  Q  I  L  A  D  N  Y  G  N  V  I  H  L
TGGGTGAGAGGGATTGCTCAATTCAGGTCGTAACCAAAAGTTACTAGAAGAAGCCCCAGCCTTGGACTCAGATCCTAAGGGAAA        2070
 G  E  R  D  C  S  I  Q  R  R  N  Q  K  L  L  E  E  A  P  S  P  A  L  D  S  D  L  R  E  K
AAATGGGACAAGCGGCGGTGAAAGCGGCTCAGTTTATCAATTACGCCGGGCAGGTACTATCGAGTTTTTGCTAGATAGATCCGGTCAGT    2160
 M  G  Q  A  A  V  K  A  A  Q  F  I  N  Y  A  G  T  I  E  F  L  L  D  R  S  G  Q  F
TTTACTTTATGGAGATGAACACCCGGATTCAAGTAGAACATCCCGTAACTGAGATGGTTACTGGAGTGGATTTATTGGTTGAGCAAATCA  2250
 Y  F  M  E  M  N  T  R  I  Q  V  E  H  P  V  T  E  M  V  T  G  V  D  L  L  V  E  Q  I  R
GAATTGCCCAAGGGGAAAGACTTAGACTAACTCAAGACCAAGTAGTTTTACGCGGTCATGCGATCGAATGTCGCATCAATGCCGAAGACC  2340
 I  A  Q  G  E  R  L  R  L  T  Q  D  Q  V  V  L  R  G  H  A  I  E  C  R  I  N  A  E  D  P
CAGACCACGATTTCCGCCCCAGCGACCCGGAGACGCATTAGCGGTTATCTTCCCCCTGGCGGTGCGGATTGACTCCCACGTTTACA     2430
 D  H  D  F  R  P  A  P  G  R  I  S  G  Y  L  P  P  G  G  P  G  V  R  I  D  S  H  V  Y  T
CGGATTACCAAATTCCGCCCTACTACGATTCCTTAATTGGTAAATTGATCGTTGGGGCCCTGATCGCGCTACTGCTATTAACCGCATGA   2520
 D  Y  Q  I  P  P  Y  Y  D  S  L  I  G  K  L  I  V  W  G  P  D  R  A  T  A  I  N  R  M  K  *
AACGGCCCCTCAGGAATGCGCCATCCATCGTCACTAGGATTACCTACCAACCATTGGGTTTCATCAAGAATTATGGAAAATCCCAATTTTACAAG 2610
 R  A  L  R  E  C  A  I  T  G  L  P  T  T  I  G  F  H  Q  R  I  M  E  N  P  Q  F  L  Q  G
GTAATGTGTCTACTAGTTTGTGCAGGAGATGAATAAATAGGGTAATGGTAATAGAGTTTCAATCACCAATTACC                 2700
 N  V  S  T  S  F  V  Q  E  M  N  K  *   *  W  V  M  G  N  R  V  S  I  T  N  Y  Q
AATTCCCTAACTCATCCGTGCCAACATCGTCAGTAATCCTTGCTGGCCTAGAAGAACTTCTCGCAACAGGCTAAAAATACCAACACACAC 2790
 F  P  N  S  S  V  P  T  S  S  V  I  L  A  G  L  E  E  L  L  A  T  G  *

AATGGGGGTGATATCAACACCACTATTGGTGGGATGATTTTTCGCAAGGAATGAGAAATGGTTCAGTCGGCCAAGCAATTAAGTTGAA    2880
GGGCAAACGGTTCAGATGCTTGCGGATCGACTTGCGGATACCAGGTCAGATTCAGAATGATACGGAGAAAATAAACAGAAATGTCATCACTCCCAATACAGGGCCAAG 2970
AATCCAAACGCTCAGGTTAACACCAGTCATCGATCTAAGCTACTATTTTGTGAATTTACAAAAAACTGCAAGCAAAAGCTGAAAATTTTA  3060
AGCTT                                                                                      3065
```

FIG. 1B

```
ATGCGTTTCA ACAAGATCCT GATCGCCAAT CGCGGCGAAA TCGCCCTGCG CATTCTCCGC

ACTTGTCAAG AACTCGGGAT CGGCACGATC GCCGTTCACT CCACTGTGGA TCGCAACGCG

CTCCATGTGC AGTTAGCGGA CGAAGCGGTC TGTATTGGCG AAGCGGCCAG CAGCAAAAGC

TATCTCAATA TCCCCAACAT CATTGCGGCG GCCCTGACCC CTAATGCCAG CGCCATTCAC

CCCGGCTATG GCTTCTTGGC GGAGAATGCC CGCTTTGCAG AAATCTGCGC CGATCACCAT

CTCACCTTTA TTGGCCCCAG CCCCGATTCG ATTCGAGCCA TGGGCGATAA ATCCACCGCT

AAGGAAACAA TGCAGCGGGT CGGCGTTCCG ACGATTCCGG GCAGTGACGG TCTGCTGACG

GATGTTGATT CGGCTGCCAA AGTTGCTGCC GAGATCGGCT ATCCCGTCAT GATCAAAGCG

ACGGCGGGGG GCGGTGGTCG CGGTATGCGG CTGGTGCGTG ACCCTGCAGA TCTGGAAAAA

CTGTTCCTTG CTGCCCAAGG AGAAGCCGAG GCAGCTTTTG GGAATCCAGG ACTGTATCTC

GAAAAATTTA TCGATCGCCC ACGCCACGTT GAATTTCAGA TCTTGGCCGA TGCCTACGGC

AATGTAGTGC ATCTAGGCGA GCGCGATTGC TCCATTCAAC GTCGTCACCA AAAGCTGCTC

GAAGAAGCCC CCAGTCCGGC GCTATCGGCA GACCTGCGGC AGAAAATGGG CGATGCCGCC

GTCAAAGTCG CTCAAGCGAT CGGCTACATC GGTGCCGGCA CCGTGGAGTT TCTGGTCGAT

GCGACCGGCA ACTTCTACTT CATGGAGATG AATACCCGCA TCCAAGTCGA GCATCCAGTC

ACAGAAATGA TTACGGGACT GGACTTGATT GCGGAGCAGA TTCGGATTGC CCAAGGCGAA

GCGCTGCGCT TCCGGCAAGC CGATATTCAA CTGCGCGGCC ATGCGATCGA ATGCCGTATC

AATGCGGAAG ATCCGGAATA CAATTTCCGG CCGAATCCTG GCCGCATTAC AGGCTATTTA

CCGCCCGGCG GCCCCGGCGT TCGTGTCGAT TCCCATGTTT ATACCGACTA CGAAATTCCG
```

FIG. 2A

```
CCCTATTACG ATTCGCTGAT TGGCAAATTG ATTGTCTGGG GTGCAACACG GGAAGAGGCG

ATCGCGCGGA TGCAGCGTGC TCTGCGGGAA TGCGCCATCA CCGGCTTGCC GACGACCCTT

AGTTTCCATC AGCTGATGTT GCAGATGCCT GAGTTCCTGC GCGGGGAACT CTATACCAAC

TTTGTTGAGC AGGTGATGCT ACCTCGGATC CTCAAGTCCT AG
``` amino acid sequence

```
MRFNKILIAN RGEIALRILR TCEELGIGTI AVHSTVDRNA LHVQLADEAV CIGEAASSKS

YLNIPNIIAA ALTRNASAIH PGYGFLAENA RFAEICADHH LTFIGPSPDS IRAMGDKSTA

KETMQRVGVP TIPGSDGLLT DVDSAADVAA EIGYPVMIKA TAGGGGRGMR LVREPADLEK

LFLAAQGEAE AAFGNPGLYL EKFIDRPRHV EFQILADAYG NVVELGERDC SIQRRHQKLL

EEAPSPALSA DLRQKMGDAA VKVAQAIGYI GAGTVEFLVD ATGNFYFMEM NTRIQVEHPV

TEMITGLDLI AEQIRIAQGE ALRFRQADIQ LRGHAIECRI NAEDPEYNFR PNPGRITGYL

PPGGPGVRVD SHVYTDYEIP PYYDSLIGKL IVWGATREEA IARMQRALRE CAITGLPTTL

SFHQLMLQMP EFLRGELYTN FVEQVMLPRI LKS
```

FIG. 2B

```
Wh ACC  ...
Rt ACC  MDEPSPLAKTLELNQHSRFIIGSVSEDNSEDEIS-NLVKLDLEEKEGSLSPASVSSDTLSDLGISALQDGLAFHMRSSMSGLHLVKQGRKRKKIDSQRDF
Ch ACC  MEESSQPAKPLEMNPHSRFIIGSVSEDNSEDETSSLVKLDLLEEKERSLSPVSVCSDSLSDLGLPSAQDGLANHMRPSMSGLHLVKQGRDRKKVDVQRDF
Yt ACC  MSEESLFESSPQKMEYEITNYSERHTELPGHFIGLNTVDKL
Sy ACC
An ACC
Ec ACC
Hm PCCA MLSAALRTLKHVLYYSRQCL
Rt PCCA MPYRERFCAIRWCRNSGRSSQQLLWTLKRAPVYSQQCL
Yt PC   MS                                                                                              100

Wh ACC  ...
Rt ACC  TVASPAEFVTRFGGNKVIEKVLIANNGIAABKCMRSIRRMSYEMFRNERAIRFVVMVTPEDLKANAEYIKMADHYVPVPGGANNNNYANVELILDIAKR
Ch ACC  TVASPAEFVTRFGGNRVIEKVLIANNGIAAVKCMRSIRRMSYEMFRNERAIRFVVMVTPEDLKANAEYIKMADHYVPVPGGPNNNNYANVELILDIAKR
Yt ACC  EESPLRDFVKSHGGHTVISKILIANNGIAAVKEIRSVRKWAYETFGDDRTVQFVAMATPEDLEANAEYIRMADQYIEVPGGTNNNNYANVDLIVDIAER
Sy ACC                                    MRFNKILIANRGEIALRILRTCEELGIGTIAVHSTVD--RNALHVQLADEAVCIGEAASS--------KSYLNIPNIIAAALT
An ACC                                    MKRFKILIANRGEIALRILRACEEMGIATIAVHSTVD--RNALHVQLADEAVCIGEPASA--------KSYLNIPNIIAAALT
Ec ACC                             MLDKIVIANRGEIALRILRACKELGIKTVAVHSSAD--RDLKHVLLADETVCIGPAPSV--------KSYLNIPAISAAEI
Hm PCCA MVSRNLGSVGYDPNEKTFDKILVANRGEIACRVIRTCKKMGIKTVAIHSDVD--ASSVHVKMADEAVCVGPAPTS--------KSYLMDAIMEAIKK
Rt PCCA VVSRSLSSVEYPEKETFDKILVANRGEIACRVIKTCRKMGIRTVAIHSDVD--ASSVHVKMADEAVCVGPAPTS--------KSYLMDAIMEAIKK
Yt PC   QRKFAGLRDNFNLLGEK-NKILVANRGEIPIRIFRTAHELSMQTVAIYSHED--RLSTHKQKADEAYVIGEVGQYTPV-----GAYLAIDEITSIAQK
                                    *   *** *                                                    *     *                  200

Wh ACC  ...
Rt ACC  IPVQAVWAGMGHASENPKLPELL--LKNGIAFMGPPSQAMWALGDKIASSIVAQTAGIPTLPWSGSGLRVDWQENDFSKRILNVPQDLYEKGYVKDVDD
Ch ACC  IPVQAVWAGMGHASENPKLPELL--HKNGIAFMGPPSQAMWALGDKIASSIVAQTAGIPTLPWNGSGLRVDWQENDLQKRILNVPQELYEKGYVKDADD
                                                                                                        300
```

```
Yt   ACC    ADVDAVWAGMGHASENPLLPEKLSQSKRKVIFIGPPGNAMRSLGDKISSTIVAQSAKVPCIPWSGTGVDTVH--VDEKTGLVSVDDDIYQKGCCTSPED
Sy   ACC    RNASAIHPGTGFLAENARFAEIC--ADHHLTFIGPSPDSIRAMGDKSTAKETMQRVGVPTIPGSDG-L----------------------------LTDVDS
An   ACC    RNASAIHPGYGFLSENAKFAEIC--ADHHIAFIGPTPEAIRLMGDKSTAKETMQKAGVPTCPGSEG-L----------------------------VETEQE
Ec   ACC    TGAVAIHPGYGFLSENANFAEQV--ERSGFIFIGPKAETIRLMGDKVSAIAAMKKAGVPCVPGSDGPL----------------------------GDDMDK
Hm   PCCA   TRAQAVHPGYGFLSENKEFARCL--AAEDVVFIGPDTHAIQAMGDKIESKLLAKKAEVNTIPGFDG-V----------------------------VKDAEE
Rt   PCCA   TGAQAVHPGYGFLSENKEFAKCL--AAEDVTFIGPDTHAIQAMGDKIESKLLAKRAKVNTIPGFDG-V----------------------------LKDADE
Yt   PC     HQVDFIHPGYGFLSENSEFADKV--VKAGITWIGPPAEVIDSVGDKVSARNLAAKANVPTVPGTPG-P----------------------------IETVEE
                * ***                    **             ***                    *                                      400

Wh   ACC    ..........VMIKASWGGGGKGIRKVHNDDEVRALFKQVQGEVPGS----PITFIMKVASQSRHLEVQLLCDKHGNVAALHSRDCSVQRRHQKIIEEG
Rt   ACC    GLKAAEEVGYPVMIKASEGGGGKGIRKVNNADDFPNLFRQVQAEVPGS----PIFVMRLAKQSRHLEVQILADQYGNAISLFGRDCSVQRRHQKIIEEA
Ch   ACC    GLRAAEEVGYPVMIKASEGGGGKGIRKVNNADDFPNLFRQFQAEVPGS----PIFVMRLAKQSRHLEVQILADQYGNAISLFGRDCSGQRRHQKIIEEA
Yt   ACC    GLQKAKRIGFPVMIKASEGGGGKGIRQVEREEDFIALYHQAANEIPGS----PIFIMKLAGRARHLEVQLLADQYGTNISLFGRDCSVQRRHQKIIEEA
Sy   ACC    AAKVAAEIGYPVMIKATAGGGGRGMRLVREPADLEKLFLAAQGEAEAAFGNPGLYLEKFIDRPRHVEFQILADAYGNVVHLGERDCSIQRRHQKLLEEA
An   ACC    GLELAKDIGYPVMIKATAGGGGRGMRLVRSPDEFVKLFLAAQGEAGAAFGNAGVYIEKFIERPRHIEFQILADNYGNVIHLGERDCSIQRRNQKLLEEA
Ec   ACC    NRAIAKRIGYPVIIKASGGGGKGMRLVREGDGGRGMRLVREPDALAQSIMTRAEAKAAFSNDMVYMEKYLENPRHVEIQVLADGQGNAIYLAERDCSMQRRHQKVVEEA
Hm   PCCA   AVRIAREIGYPVMIKATAGGGKGMRIAWDDEETRDGFRLSSQEAASSFGDDRLLIEKFIDNPRHIEIQVLGDKHGNALWLNERECSIQRRNQKVVEEA
Rt   PCCA   AVRIAREIGYPVMIKASAGGGGKGMRIPWDDEETRDGFRFSSQEAASSFGDDRLLIEKFIDNPRHIEIQVLGDKHGNALWLNERECSIQRRNQKVVEEA
Yt   PC     ALDFVNEYGYPVIIKAAFGGGGRGMRVVREGDDVADAFQRATSEARTAFGNGTCFVERFLDKPKHIEVQLLADNHGNVVHLFERDCSVQRRHQKVVEVA
                  *  * *****   * * ******* **                      ** **** **  *  * *** *** ** * * *** ** **         500

Wh   ACC    PITVAPPETIKELEQAARRLAKCVQYQGAATVEYLYSMETGEYYFLELNPRLQVEHPVTEWIAEINLPASQVVVGMGIPLYNIPEIRRFYGIEHGGGYH
Rt   ACC    PAAIATPAVFEHMEQCAVKLAKMVGYVSAGTVEYLYSAGTVEYLYSQD-GSFYFLELNPRLQVEHPCTEMVADVNLPAAQLQIAMGIPLFRIKDIRMMYGVSPWGDAP
Ch   ACC    PSIATSVVFEHMEQCAVKLAKMVGYVSAGTVEYLYSAGTVEYLYSQD-GSFYFLELNPRLQVEHPCTEMVADVNLPAAQLQIAMGIPLFRIKDIRVMYGVSPWGDGS
Yt   ACC    PVTIAKAETFHEMEKAAVRLGKLVGYVSAGTVEYLYSHDDGKFYFLELNPRLQVEHPTTEMVSGVNLPAAQLQIAMGIPMHRISDIRTLYGMNPHSASE
Sy   ACC    PSPALSADLRQKMGDAAVKVAQAIGYIGAGTVEFLVD-ATGNFYFMEMNTRIQVEHPVTEMITGLDLIAEQIRIAQGEALRFQADIQ---------
```

```
An  ACC   PSPALDSDLREKMGQAAVKAAQFINYAGAGTIEFLLD-RSGQFYFMEMNTRIQVEHPVTEMVTGVDLLVEQIRIAQGERLRLTQDQVV-------
Ec  ACC   PAPGITPELRRYIGERCAKACVDIGYRGAGTFEFLF--ENGEFYFIEMNTRIQVEHPVTEMITGVDLIKEQMRIAAGQPLSIKQEEVH-------
Hm  PCCA  PSIFLDAETRRAMGEQAVALARAVKYSSAGTVEFLVDSK-KNFYFLEMNTRLQVEHPVTECIHWPGPSPGKTVLQEHLSGTNKLIFA-------
Rt  PCCA  PSIFLDPETRRAMGEQAVAWPKAVKYSSAGTVEFLVDSQ-KNFYFLEMNTRLQVEHPVTECITGLDLVQEMILVAKGYPLRHKQEDIP------
Yt  PC    PAKTLPREVRDAILTDAVKLAKECGYRNAGTAEFLVDNQ-NRHYFIEINPRIQVEHTITEEITGIDIVAAQIQIAAGASLPQLGLFQDKIT----
                *      ***  **     * *** ** *        *     ** *     **      *    ****** **         *
                                                                                                        600
Wh  ACC   AMKEISAVATKFDLDKAQSVKPKGHCVAVRVTSEDPDDGFK-PTSGRVEELNFKSKPNVWAYF----SVKSGGAIHEFSDSQFGHVFAFGESRSLAIAN
Rt  ACC   IDFENSAHVPC--------PRGHVIAARITSENPDEGFK-PSSGTVQELNFRSNKNVWGYF----SVAAAGGLHEFADSQFGHCFSWGENREEAISN
Ch  ACC   IDFENSAHVPC--------PRGHVIAARITSENPDEGFK-PSSGTVQELNFRSNKNVWGYF----SVAAAGGLHEFADSQFGHCFSWGENREEAISN
Yt  ACC   IDFEFKTQDAT---KKQRRPIPKGHCTACRITSEDPNDGFK-PSGGTLHELNFRSSSNVWGYG---SVGNNGNIHSFSDSQFGHIFAFGENRQASRKH
Sy  ACC   -----------------LRGHAIECRINAEDPEYNF-RPNPGRITG--YLPPGG-PGVRVDS-HVYTDYEIPPYYDSLIGKLIVWGATREEAIAR
An  ACC   -----------------LRGHAIECRINAEDPDHDF-RPAPGRISG--YLPPGG-PGVRISG-HVYTDYQIPPYYDSLIFKLIVWGPDRATAINR
Ec  ACC   -----------------VRGHAVECRINAEDPN-TF-LPSPGKITR--FHAPGG-FGVRWES-HIYAGYTVPPYYDSMIGKLICYGENRDVAIAR
Hm  PCCA  -----------------FNGWAVECRVYAEDPYKSFGLPSIGRLSQ--YQEPLHLPGCRVDS-GIQPGSDISIYYDPMISKLITYGSDRTEALKR
Rt  PCCA  -----------------ISGWAVECRVYAEDPYKSFGLPSIGRLSQ--YQEPIHLPGVRVDS-GIQPGSDISIYHDPMISKLVTYGSDRAEALKR
Yt  PC    -----------------TRGFAIQCRITTEDPAKNFQ-PDTGRIEV--YRSAGG-NGVRLDGGNAYAGTIISPHYDSMLVKCSCSGSTYEIVRRK
                           *    *   *   *         *       *          *              *
                                                                                                        700
Wh  ACC   MVLGLKEIQIRGEIRTNVDYTVDLLNAAEYRENMIHTGWLDSRIAMRVRAERPPWYLSVVGGALYEASSRSSSVVTDVGYLSKGQIPPK-------
Rt  ACC   MVVALKELSIRGDGRTTVEYLIKLLETESFQLNRIDTGWLDRLIAEKVQAERPDTMLGVVCGALHCADVNLRNSISNGLHSLERGQVLPA-----
Ch  ACC   MVVALKELSIRGDFRTTVEYLIKLLETESFQQNRIDTGWLDRLIAEKVQAERPDTMLGVVCGALHVADVSFRNSVSNFLHSLERGQVLPA-----
Yt  ACC   MVVALKELSIRGDFRTTVEYLIKLLETEDFEDNTITTGWLDDLITHKMTAEKPDPTLAVICGAATKAFLASEEARHKYIESLQKGQVLSK-----
Sy  ACC   MQRALRECAITG-LPTTLSFHQLMLQMPEFLRGELYTNFVEQVMLPRILKS
An  ACC   MRKALRECAITG-LPTTIGFHQRIMENPQFLQGNVSTSFVQEMNK                    PLDFNEIRQLLTTIAQ
Ec  ACC   MKNALQELIIDG-IKTNVDLQIRIMNDENFQHGGTNIHYLEKKLGLQEK
```

FIG. 3C

```
Hm PCCA  MADALDNYVIRG-VTHNIALLREVIINSRFVKGDISTKFLSDVVPDGFKGHMLTKSEKNQLLAIASSLGVAVQLRAQHFQENSRMPVIKPDIANWELSV
Rt PCCA  MEDALDSYVIRG-VTHNIPLLREVIINTRFVKGDISTKFLSDVVPDGFKGHMLTPSERDQLLAIASSLFVASQLRAQRFQEHSRVPVIRPDVAKWELSV
Yt PC    MIRALIEFRIRG-VKTNIPFLLTLLTNPVFIEGTYWGTFIDDTPQLFQMVSSQNRAQKLLHYLADVADNGSSIKGQIGLPKLKSNPSVPH-#-SYNMYP
Kp ODA                                                                                            -##-NAIDD
          *  **          *       * *                                                                        800

Wh ACC   -------HISLVNLTVTLNIDGSKYTIETVRGGPRSYKLRINESEVEAEIHFLRDGGLLMQLDGNSHVIYAETEAAGTRLLINGRTCLLQKEHDPSRL
Rt ACC   -------HTLLNTVDVELIYEGIKYVLKVTRQSPNSYVVIMNGSCVEVDVHRLSDGGLLLSYDGSSYTTYMKEEVDRYRITIGNKTCVFEKENDPSVM
Ch ACC   -------HTLLNTVDVELIYEGIKYVLKVTRQSPNSYVVIMNSSCVEVDVHRLSDGGLLLSYDGSSYTTYMKEEVDRYRITIGNKTCVFEKENDPSIL
Yt ACC   -------DLLQTMFPVDFIHEGKRYKFTVAKSGNDRYTLFINGSKCDIILRQLSDGGLLIAIGGKSHTIYWKEEVAATRLSVDSMTTLLEVENDPTQL
An ACC   TDIAEVTLKSDDFELTVRKAVGVNNSVVPVVTAPLSGVVGSGLPSAIPIVAHAAPSPSPEPGTSRAADHAVTSSGSQPGAKIIDQKLAEVASPMVGTFY
Ec ACC           MDIRKIKKLIELVEESGISELEISEGEESVRISRAAPAASFPVMQQAYAAPMMQQPAQSNAAAPATVPSMEAPAAAEISGHIVRSPMVGTFY
Hm PCCA  KLHDKVHTVVASNNGSVFSVEVDGSKLNVTSTWNLASPLLSVSVDGTQRTVQCLSREAGGNMSIQFLGTVYKVNILTRLAAELNKFMLEKVTEDTSSVL
Rt PCCA  KLHDEDHTVVASNNGPTFNVEVDGSKLNVTSTWNLASPLLSVNVDGTQRTVQCLSPDAGGNMSIQFLGTVYKVHILTKLAAWLNKFMLEKVPKDTSSVL
Yt PC    RVYEDFQKMRETYGDLSVLPTRSFLSPLETDEEIEVVIEQGKTLIIKLQAVGDLNKKTGEREVYFDLNGEMRKIRVADRSQKVETVTKSKADMHDPLHI
Kp ODA   VLTVALFPQPGLKFLENRHNPAAFEPVPQAEAAQPVAKAEKPAASGVYTVEVEGKAFVVKVSDGGDVSQLTAAAPAPAPAPAPASAPAAAAPAGAGTPV
PS TC                               MKLKVTVNGTAYDVDVDVDVDKSHENPMGTILFGGGTGGAPAPRAAGGAGAGKAGEGEI
                                                                                                           900

Wh ACC   LADTPCKLLRFLVADGSHVVADTPYAEVEAMKM.............................
Rt ACC   RSPSAGKLIQYIVEDGGHVFAGQCYAEIEVMKMVMTLTAVESGCIHYVKRPGAALDPGCVIAKMALDNPSKVQQAELHTGSLPQIQSTALRGEKLHRIF
Ch ACC   RSPSAGKLIQYVVEDGGHVFAGQCFAEIEVMKMVMTLTAGESGCIHYVKRPGAVLDPGCVIAKLQLDDPSRVQQAELHTGTLPQIQSTALRGEKLHRIF
Yt ACC   RTPSPGKLVKFLVENGEHIIKGQPYAEIEVMKMQMPLVSQENGIVQLLKQPGSTIVAGDIMAIMTLDDPSKVKHALPFEGMLPDFGSPVIEGTKPAYKF
An ACC   RAPAPGE--AVFVEVGDRIRQGQTVCIIEAMKM.............................
Ec ACC   RTPSPDA--KAFIEVGQKVNVGDTLCIVEAMKMMNQIEADKSGTVKAILVESGQPVEFDEPLVVIE
Hm PCCA  RSPMPGVVVAVSVKPGDAVAEGQEICVIEAMKMQNSMTAGKTGTVKSVHCQAGDTVGEGDLLVELE
Rt PCCA  RSPKPGVVVAVSVKPGDMVAEGQEICVIEAMKMQNSMTAGKMGKVKLVHCKAGDTVGEGDLLVELE
```

FIG. 3D

```
Yt PC    GAPMAGVIVEVKVHKGSLIKKGQPVAVLSAMKMEMISSPSDGQVKEVFVSDGENVDSSDLLVLLEDQVPVETKA
Kp ODA   TAPLAGTIWKVLASEGQTVAAGEVLLILEAMKMETEIRAAQAGTVRGIAVKAGDAVAVGDTLMTLA
Ps TC    PAPLAGTVSKILVKEGDTVKAGDTVLVLEAMKMETEINAPTDGKVEKVLVKERDAVQGGGQGLIKIG
         *        *       *  ***               -------------------------
```

FIG. 3E

```
GTGATGATCAAGGCATCATGGGGTGGGGTGGTAAAGGAATAAGGAAGTACATAATGATGAGTCAGAGCATTGTTTAAGCAAGTG      90
 V  M  I  K  A  S  W  G  G  G  G  K  G  I  R  K  V  H  N  D  D  E  V  R  A  L  F  K  Q  V

CAAGGAGAAGTCCCCGGATGCCTATATTTATTATGAAGGTGGCATCTCAGAGTCGACATCTAGAGGTTCAATTGCTCTGTGACAAGCAT    180
 Q  G  E  V  P  G  S  P  I  F  I  M  K  V  A  S  Q  S  R  H  L  E  V  Q  L  L  C  D  K  H

GGCAACGTGGCAGCACTGCACAGTCGAGACTGTAGTGTTCAAAGAAGGCATCAAAAGATCATTGAGGAGGACCAATTACAGTTGCTCCT    270
 G  N  V  A  A  L  H  S  R  D  C  S  V  Q  R  R  H  Q  K  I  I  E  E  G  P  I  T  V  A  P

CCAGAAACAATTAAAGAGCTTGAGCAGGCGGCAAGGCGACTAGCTAAATGTGTGCAATATCAGGTTGCTGCTACAGTGGAATATCTGTAC    360
 P  E  T  I  K  E  L  E  Q  A  A  R  R  L  A  K  C  V  Q  Y  Q  G  A  A  T  V  E  Y  L  Y

AGCATGGAAACAGGCGAATACTATTTCCTGGAGCTTAATCCAAGTTGCAGGTAGAACACCCTGTGACCGAATGGATTGCTGAAATAAAC    450
 S  M  E  T  G  E  Y  Y  F  L  E  L  N  P  R  L  Q  V  E  H  P  V  T  E  W  I  A  E  I  N

TTACCTGCATCTCAAGTTGTAGTAGGAATGGGCATACCACTCTACAACATTCCAGAGATCAGAGCGCTTTTATGAATAGAACATGGAGGT    540
 L  P  A  S  Q  V  V  V  G  M  G  I  P  L  Y  N  I  P  E  I  R  R  F  Y  G  I  E  H  G  G

GGCTATCATGCTTGGAAGGAAATATCAGCTGTTGCAACTAAATTTGATTTGGACAAAGCACAGTCTGTAAAGCCAAAAGGTCATTGTGTA    630
 G  Y  H  A  W  K  E  I  S  A  V  A  T  K  F  D  L  D  K  A  Q  S  V  K  P  K  G  H  C  V

GCAGTTAGAGTTACTAGCGAGGATCCAGATGATGGGTTTAAGCCTACCAGTGGAAGAGTAGAAGAGCTGAACTTTAAAAGTAAACCCAAT    720
 A  V  R  V  T  S  E  D  P  D  D  G  F  K  P  T  S  G  R  V  E  E  L  N  F  K  S  K  P  N
```

FIG. 6A

```
                                                                                                    C
GTTTGGGCCTATTCTCCGTAAGTCCGAGGTGCAATTCACGAGTTCTCTGATTCCCAGTTGGTCATGTTTTGCTTTTGGGGAATCT            810
 V  W  A  Y  F  S  V  K  S  G  G  A  I  H  E  F  S  D  S  Q  F  G  H  V  F  A  F  G  E  S
                R                                                            S
                T
                A
                                                                   A    C
AGGTCATTGGCAATAGCCAATATGGTACTTGGGGTTAAAAGAGATCCAAATTCGTGGAGAGATACGCACTAATGTTGACTACACTGTGGAT       900
 R  S  L  A  I  A  N  M  V  L  G  L  K  E  I  Q  I  R  G  E  I  R  T  N  V  D  Y  T  V  D
                         K
CTCTTGAATGCTGCAGAGTACCGAGAGAATATGATTCACACTGGTTGGCTAGACAGCAGAATAGCTATGCGGTTAGAGCAGAGAGGCCC        990
 L  L  N  A  A  E  Y  R  E  N  M  I  H  T  G  W  L  D  S  R  I  A  M  R  V  R  A  E  R  P
                                C
CCATGGTACCTTTCAGTTGTTGGTGGAGCTCTATATGAAGCATCAAGCAGGAGCTCGAGTGTTGTAACCGATTATGTTGGTTATCTCAGT      1080
 P  W  Y  L  S  V  V  G  G  A  L  Y  E  A  S  S  R  S  S  S  V  V  T  D  Y  V  G  Y  L  S
                                                                        CG
                                                                        CG
AAAGGTCAAATACCACCAAAGCACATCTCTTGTCAATTTGACTGTAACACTGAATATAGATGGGAGCAAATATACGATTGAGACAGTA         1170
 K  G  Q  I  P  P  K  H  I  S  L  V  N  L  T  V  T  L  N  I  D  G  S  K  Y  T  I  E  T  V
                            A                                                              C
                            A                                                              T
CGAGGTGGACCCCGTAGCTACAAATTAAGAATTAATGAATCAGAGGTTGAGGCAGAGATACATTCCTGCGAGATGGCGGACTCTTAATG        1260
 R  G  G  P  R  S  Y  K  L  R  I  N  E  S  E  V  E  A  E  I  H  F  L  R  D  G  G  L  L  M
                G
                T
CAGTTGGATGGAAACAGTCATGTAATTTACGCCGAGAGAAGCTGCTGGCACGGCCTTCTAATCAATGGGAGAACATGCTTATTACAG         1350
 Q  L  D  G  N  S  H  V  I  Y  A  E  T  E  A  A  G  T  R  L  L  I  N  G  R  T  C  L  L  Q
    S                                                   S

FIG. 6B
```

```
                    T               A       G                   A
                    ↓               ↓       ↓                   ↓
AAAGAGCAGATCCTTCCAGGTTGTTGGCTGATACACCGTGCAAACTTCTCGGTTTTTGGTCGCGGATGGTTCTCATGTGGTTGCTGAT   1440
 K  E  H  D  P  S  R  L  L  A  D  T  P  C  K  L  L  R  F  L  V  A  D  G  S  H  V  V  A  D
                                                          A         S
                                                          G
          T
          ↓
ACGCCATATGCCGAGGTGGAAGCCATGAAAATG
 T  P  Y  A  E  V  E  A  M  K  M
```

FIG. 6C

TCTAGACTTTAACGAGATTCGTCAACTGCTGACAACTATTGCACAAACAGATATCGGGAAGTAACGCTCAAAAGTGATGATTTTGAACT    90
 L  D  F  N  E  I  R  Q  L  L  T  T  I  A  Q  T  D  I  A  E  V  T  L  K  S  D  D  F  E  L

AACGGTGCGTAAAGCTGTTGGTGTGAATAATAGTGTTGTGCCGGTTGTGACAGCACCCTTGAGTGGTGTAGGTTCGGATTGCCATC    180
 T  V  R  K  A  V  G  V  N  N  S  V  V  P  V  V  T  A  P  L  S  G  V  V  G  S  G  L  P  S

GGCTATACCGATTGTAGCCCCATGCTGCCCCATCTCCAGAGCCGGGAACAAGCCGTGCTGATCATGCTGTCAGAGTTCTGG    270
 A  I  P  I  V  A  H  A  A  P  S  P  E  P  G  T  S  R  A  A  D  H  A  V  T  S  S  G

CTCACAGCCAGGAGCAAAAATCATTGACCAAAAATTAGCAGAAGTGGCTTCCCCAATGGTGGGAACATTTTACGCGCTCCTGCACCAGG    360
 S  Q  P  G  A  K  I  I  D  Q  K  L  A  E  V  A  S  P  M  V  G  T  F  Y  R  A  P  A  P  G

TGAAGCGGGTATTTGTGGAAGTCGGCGATCGCATCCGTCAAGGTCAAACCGTCTGCATCATCGAAGCGATGAAAAUG
 E  A  V  F  V  E  V  G  D  R  I  R  Q  G  Q  T  V  C  I  I  E  A  M  K  M

FIG. 8

SEQUENCE LISTING ( 1 ) GENERAL INFORMATION:

( i i i ) NUMBER OF SEQUENCES: 116

( 2 ) INFORMATION FOR SEQ ID NO:1:

( i ) SEQUENCE CHARACTERISTICS:
        ( A ) LENGTH: 3065 base pairs
        ( B ) TYPE: Nucleic acid
        ( C ) STRANDEDNESS: Single
        ( D ) TOPOLOGY: Linear ( i i ) MOLECULE TYPE: Oligonucleotide ( x i ) SEQUENCE DESCRIPTION: SEQ ID NO:1:

```
GTAATAAATA CCCCGCACAT CCCGATACAA CTCCGTGCGA AGACGAGCTA GACTTGCCCA   240
AATTGGTAAT GAACGGTTTT GCAAATACTC GTCTACATGG CTGGCTTCCC ACCATGAGGT   300
TGCATAGGCG AGTCGTTGGC CAGAGCGTGT ACGTAGCCAT ACCTGTCGCC GCAGTCTTGG   360
CGCTGGAACA GATTGGATTA AATCCGGCGC ACTATCTAAA TCCAAACCAA TCAATGACAT   420
ATCAATGACA TCGACTTCTG TTGGCTCACC AGTAAGTAAT TCTAAATGCC TTGTGGGTGA   480
GCCATCACCT AAGAGTAGTA GTTGCCACGC TGGAGCCAGC TGAGTGTGAG GCAAACTATG   540
TTTAATTACT TCTTCCCCAC CTTGCCAAAT AGGAGTGAGG CGATGCCATC CGGCTGGCAG   600
TGTTGAGTTG TTGCTTGGAG TAAAAGTGGC AGTCAATGTT CTTTACAAAA GTTCACCTAT   660
TTATATCAAA GCATAAAAAA TTAATTAGTT GTCAGTTGTC ATTGGTTATT CTTCTTTGCT   720
CCCCCTGCCC CCTACTTCCC TCCTCTGCCC AATAATTAGA AAGGTCAGGA GTCAAAAACT   780
TATCACTTTT GACCACTGAC CTTTCACAAT TGACTATAGT CACTAAAAAA TGCGGATGGC   840
GAGACTCGAA CTCGCAAGGC AAAGCCACAC GCACCTCAAG CGTGCGCGTA TACCAATTCC   900
GCCACATCCG CACGGGTTGT ACAAGAAGAT ATACTAGCAC AAAAAAATTG CATAAAACAA   960
GGTAAAACTA TATTTGCCAA ACTTTATGGA AAATTATCT TGCTAAATAT ACAAATTTCC  1020
CGAAGAGGAT ACGAGACTAA CAGAAATGTA GTATCGCCAC AAGTGATATT AAGGGGGTA   1080
TGGGGGTTTT CTTCCCTTAC ACCCTTAAAC CCTCACACCC CACCTCCATG AAAAATCTTG  1140
TTGGTAAGTC CGTTTCCTGC AATTTATTTA AAGATGAGCC TGGGGTATCT CCTGTCATAA  1200
TTTGAGATGA AGCGATGCCT AAGGCGGCTA CGCTACGCGC TAAAAGCAAC TTGGATGGGA  1260
GACAATTTCT ATCTGCTGGT ACTGATACTG ATATCGAAAA CTAGAAAATG AAGTTTGACA  1320
AAATATTAAT TGCCAATCGG GGAGAAATAG CGCTGCGCAT TCTCCGCGCC TGTGAGGAAA  1380
TGGGGATTGC GACGATCGCA GTTCATTCGA CTGTTGACCG GAATGCTCTT CATGTCCAAC  1440
TTGCTGACGA AGCGGTTTGT ATTGGCGAAC CTGCTAGCGC TAAAAGTTAT TTGAATATTC  1500
CCAATATTAT TGCTGCGGCT TAACGCGCA ATGCCAGTGC TATTCATCCT GGGTATGGCT  1560
TTTTATCTGA AAATGCCAAA TTTGCGGAAA TCTGTGCTGA CCATCACATT GCATTCATTG  1620
GCCCCACCCC AGAAGCTATC CGCCTCATGG GGGACAAATC CACTGCCAAG GAAACCATGC  1680
AAAAAGCTGG TGTACCGACA GTACCGGGTA GTGAAGGTTT GGTAGAGACA GAGCAAGAAG  1740
GATTAGAACT GGCGAAAGAT ATTGGCTACC CAGTGATGAT CAAAGCCACG GCTGGTGGTG  1800
GCGGCCGGGG TATGCGACTG GTGCGATCGC CAGATGAATT TGTCAAACTG TTCTTAGCCG  1860
CCCAAGGTGA AGCTGGTGCA GCCTTTGGTA ATGCTGGCGT TTATATAGAA AAATTTATTG  1920
AACGTCCGCG CCACATTGAA TTTCAAATTT GGCTGATAA TTACGGCAAT GTGATTCACT  1980
TGGGTGAGAG GGATTGCTCA ATTCAGCGTC GTAACCAAAA GTTACTAGAA GAAGCCCCA   2040
GCCCAGCCTT GGACTCAGAC CTAAGGGAAA AAATGGGACA AGCGGCGGTG AAAGCGGCTC  2100
AGTTTATCAA TTACGCCGGG GCAGGTACTA TCGAGTTTTT GCTAGATAGA TCCGGTCAGT  2160
TTTACTTTAT GGAGATGAAC ACCCGGATTC AAGTAGAACA TCCCGTAACT GAGATGGTTA  2220
CTGGAGTGGA TTTATTGGTT GAGCAAATCA GAATTGCCCA AGGGGAAAGA CTTAGACTAA  2280
CTCAAGACCA AGTAGTTTTA CGCGGTCATG CGATCGAATG TCGCATCAAT GCCGAAGACC  2340
CAGACCACGA TTTCCGCCCA GCACCGGAC GCATTAGCGG TTATCTTCCC CCTGGCGGCC  2400
CTGGCGTGCG GATTGACTCC CACGTTTACA CGGATTACCA AATTCCGCCC TACTACGATT  2460
CCTTAATTGG TAAATTGATC GTTTGGGGCC CTGATCGCGC TACTGCTATT AACCGCATGA  2520
AACGCGCCCT CAGGGAATGC GCCATCACTG GATTACCTAC AACCATTGGG TTTCATCAAA  2580
```

```
GAATTATGGA  AAATCCCCAA  TTTTTACAAG  GTAATGTGTC  TACTAGTTTT  GTGCAGGAGA    2640

TGAATAAATA  GGGTAATGGG  TAATGGGTAA  TGGGTAATAG  AGTTTCAATC  ACCAATTACC    2700

AATTCCCTAA  CTCATCCGTG  CCAACATCGT  CAGTAATCCT  TGCTGGCCTA  GAAGAACTTC    2760

TCGCAACAGG  CTAAAAATAC  CAACACACAC  AATGGGGGTG  ATATCAACAC  CACCTATTGG    2820

TGGGATGATT  TTTCGCAAGG  GAATGAGAAA  TGGTTCAGTC  GGCCAAGCAA  TTAAGTTGAA    2880

GGGCAAACGG  TTCAGATCGA  CTTGCGGATA  CCAGGTCAGA  ATGATACGGA  AAATAAACAG    2940

AAATGTCATC  ACTCCCAATA  CAGGGCCAAG  AATCCAAACG  CTCAGGTTAA  CACCAGTCAT    3000

CGATCTAAGC  TACTATTTTG  TGAATTTACA  AAAAACTGCA  AGCAAAAGCT  GAAAATTTTA    3060

AGCTT                                                                     3065
```

( 2 ) INFORMATION FOR SEQ ID NO:2:

( i ) SEQUENCE CHARACTERISTICS:
        ( A ) LENGTH: 32 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:2:

```
Asp Glu Ala Met Pro Lys Ala Ala Thr Leu Arg Ala Lys Ser Asn Leu
              5                   10                  15
Asp Gly Arg Gln Phe Leu Ser Ala Gly Thr Asp Thr Asp Ile Glu Asn
             20                   25                  30
```

INFORMATION FOR SEQ ID NO:3:

( i ) SEQUENCE CHARACTERISTICS:
        ( A ) LENGTH: 427 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:3:

```
Lys Met Lys Phe Asp Lys Ile Leu Ile Ala Asn Arg Gly Glu Ile Ala
              5                   10                  15
Leu Arg Ile Leu Arg Ala Cys Glu Glu Met Gly Ile Ala Thr Ile Ala
             20                   25                  30
Val His Ser Thr Val Asp Arg Asn Ala Leu His Val Gln Leu Ala Asp
             35                   40                  45
Glu Ala Val Cys Ile Gly Glu Pro Ala Ser Ala Lys Ser Tyr Leu Asn
         50                   55                  60
Ile Pro Asn Ile Ile Ala Ala Ala Leu Thr Arg Asn Ala Ser Ala Ile
65                       70                  75  80
His Pro Gly Tyr Gly Phe Leu Ser Glu Asn Ala Lys Phe Ala Glu Ile
                     85                   90                  95
Cys Ala Asp His His Ile Ala Phe Ile Gly Pro Thr Pro Glu Ala Ile
                    100                  105                 110
Arg Leu Met Gly Asp Lys Ser Thr Ala Lys Glu Thr Met Gln Lys Ala
            115                  120                  125
Gly Val Pro Thr Val Pro Gly Ser Glu Gly Leu Val Glu Thr Glu Gln
        130                  135                  140
Glu Gly Leu Glu Leu Ala Lys Asp Ile Gly Tyr Pro Val Met Ile Lys
145                  150                  155                 160
Ala Thr Ala Gly Gly Gly Gly Arg Gly Met Arg Leu Val Arg Ser Pro
                    165                  170                  175
Asp Glu Phe Val Lys Leu Phe Leu Ala Ala Gln Gly Glu Ala Gly Ala
```

|   |   |   |   |   | 180 |   |   |   |   |   | 185 |   |   |   |   |   | 190 |   |   |
|---|---|---|---|---|---|---|---|---|---|---|---|---|---|---|---|---|---|---|---|
| Ala | Phe | Gly 195 | Asn | Ala | Gly | Val | Tyr | Ile | Glu 200 | Lys | Phe | Ile | Glu 205 | Arg | Pro |
| Arg | His 210 | Ile | Glu | Phe | Gln | Ile 215 | Leu | Ala | Asp | Asn | Tyr | Gly 220 | Asn | Val | Ile |
| His 225 | Leu | Glu | Arg | Asp | Cys 230 | Ser | Ile | Gln | Arg | Arg 235 | Asn | Gln | Lys | Leu | Leu 240 |
| Glu | Glu | Ala | Pro | Ser 245 | Pro | Ala | Leu | Asp | Ser 250 | Asp | Leu | Arg | Glu | Lys 255 | Met |
| Gly | Gln | Ala | Ala 260 | Val | Lys | Ala | Ala | Gln 265 | Phe | Ile | Asn | Tyr | Ala 270 | Gly | Ala |
| Gly | Thr | Ile 275 | Glu | Phe | Leu | Leu | Asp 280 | Arg | Ser | Gly | Gln | Phe 285 | Gly | Val | Asp |
| Leu | Leu 290 | Val | Glu | Gln | Ile | Arg 295 | Ile | Ala | Gln | Gly | Glu 300 | Arg | Leu | Arg | Leu |
| Thr 305 | Gln | Asp | Gln | Val | Val 310 | Leu | Arg | Gly | His | Ala 315 | Ile | Glu | Cys | Arg | Ile 320 |
| Asn | Ala | Glu | Asp | Pro 325 | Asp | His | Asp | Phe | Arg 330 | Pro | Ala | Pro | Gly | Arg 335 | Ile |
| Ser | Gly | Tyr | Leu 340 | Pro | Pro | Gly | Gly | Pro 345 | Gly | Val | Arg | Ile | Asp 350 | Ser | His |
| Val | Tyr | Thr 355 | Asp | Tyr | Gln | Ile | Pro 360 | Pro | Tyr | Tyr | Asp | Ser 365 | Leu | Ile | Gly |
| Lys | Leu 370 | Ile | Val | Trp | Gly | Pro 375 | Asp | Arg | Ala | Thr | Ala 380 | Ile | Asn | Arg | Met |
| Lys 385 | Arg | Ala | Leu | Arg | Glu 390 | Cys | Ala | Ile | Thr | Gly 395 | Leu | Pro | Thr | Thr | Ile 400 |
| Gly | Phe | His | Gln | Arg 405 | Ile | Met | Glu | Asn | Pro 410 | Gln | Phe | Leu | Gln | Gly 415 | Asn |
| Val | Ser | Thr | Ser 420 | Phe | Val | Gln | Glu | Met 425 | Asn | Lys |

INFORMATION FOR SEQ ID NO:4:

( i ) SEQUENCE CHARACTERISTICS:
        ( A ) LENGTH: 36 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:4:

| Trp | Val | Met | Gly | Asn 5 | Arg | Val | Ser | Ile | Thr 10 | Asn | Tyr | Gln | Phe | Pro 15 | Asn |
|---|---|---|---|---|---|---|---|---|---|---|---|---|---|---|---|
| Ser | Ser | Val | Pro | Thr 20 | Ser | Ser | Val | Ile | Leu 25 | Ala | Gly | Leu | Glu | Glu 30 | Leu |
| Leu | Ala | Thr | Gly 35 | | | | | | | | | | | | |

( 2 ) INFORMATION FOR SEQ ID NO:5:

( i ) SEQUENCE CHARACTERISTICS:
        ( A ) LENGTH: 1362 base pairs
        ( B ) TYPE: Nucleic acid
        ( C ) STRANDEDNESS: Single
        ( D ) TOPOLOGY: Linear ( i i ) MOLECULE TYPE: Oligonucleotide ( x i ) SEQUENCE DESCRIPTION: SEQ ID NO:5:

```
TGCGTTTCA ACAAGATCCT GATCGCCAAT CGCGGCGAAA TCGCCCTGCG CATTCTCCGC  60
ACTTGTCAAG AACTCGGGAT CGGCACGATC GCCGTTCACT CCACTGTGGA TCGCAACGCG 120
CTCCATGTGC AGTTAGCGGA CGAAGCGGTC TGTATTGGCG AAGCGGCCAG CAGCAAAAGC 180
TATCTCAATA TCCCCAACAT CATTGCGGCG GCCCTGACCC CTAATGCCAG CGCCATTCAC 240
CCCGGCTATG GCTTCTTGGC GGAGAATGCC CGCTTTGCAG AAATCTGCGC CGATCACCAT 300
CTCACCTTTA TTGGCCCCAG CCCCGATTCG ATTCGAGCCA TGGGCGATAA ATCCACCGCT 360
AAGGAAACAA TGCAGCGGGT CGGCGTTCCG ACGATTCCGG GCAGTGACGG TCTGCTGACG 420
GATGTTGATT CGGCTGCCAA AGTTGCTGCC GAGATCGGCT ATCCCGTCAT GATCAAAGCG 480
ACGGCGGGGG GCGGTGGTCG CGGTATGCGG CTGGTGCGTG ACCCTGCAGA TCTGGAAAAA 540
CTGTTCCTTG CTGCCCAAGG AGAAGCCGAG GCAGCTTTTG GAATCCAGG ACTGTATCTC 600
GAAAAATTTA TCGATCGCCC ACGCCACGTT GAATTTCAGA TCTTGGCCGA TGCCTACGGC 660
AATGTAGTGC ATCTAGGCGA GCGCGATTGC TCCATTCAAC GTCGTCACCA AAAGCTGCTC 720
GAAGAAGCCC CCAGTCCGGC GCTATCGGCA GACCTGCGGC AGAAAATGGG CGATGCCGCC 780
GTCAAAGTCG CTCAAGCGAT CGGCTACATC GGTGCCGGCA CCGTGGAGTT TCTGGTCGAT 840
GCGACCGGCA ACTTCTACTT CATGGAGATG AATACCCGCA TCCAAGTCGA GCATCCAGTC 900
ACAGAAATGA TTACGGGACT GGACTTGATT GCGGAGCAGA TTCGGATTGC CAAGGCGAA 960
GCGCTGCGCT TCCGGCAAGC CGATATTCAA CTGCGCGGCC ATGCGATCGA ATGCCGTATC 1020
AATGCGGAAG ATCCGGAATA CAATTTCCGG CCGAATCCTG CCGCATTAC AGGCTATTTA 1080
CCGCCCGGCG GCCCCGGCGT TCGTGTCGAT TCCCATGTTT ATACCGACTA CGAAATTCCG 1140
CCCTATTACG ATTCGCTGAT TGGCAAATTG ATTGTCTGGG GTGCAACACG GAAGAGGCG 1200
ATCGCGCGGA TGCAGCGTGC TCTGCGGGAA TGCGCCATCA CCGGCTTGCC GACGACCCTT 1260
AGTTTCCATC AGCTGATGTT GCAGATGCCT GAGTTCCTGC GCGGGGAACT CTATACCAAC 1320
TTTGTTGAGC AGGTGATGCT ACCTCGGATC CTCAAGTCCT AG                  1362
```

INFORMATIONN FOR SEQ ID NO:6:

( i ) SEQUENCE CHARACTERISTICS:
  ( A ) LENGTH: 453 amino acids
  ( B ) TYPE: Amino acid
  ( C ) STRANDEDNESS: Single
  ( D ) TOPOLOGY: Linear ( i i ) MOLECULE TYPE: Peptide ( x i ) SEQUENCE DESCRIPTION: SEQ ID NO:6:

```
Met Arg Phe Asn Lys Ile Leu Ile Ala Asn Arg Gly Glu Ile Ala Leu
              5                  10                  15
Arg Ile Leu Arg Thr Cys Glu Glu Leu Gly Ile Gly Thr Ile Ala Val
             20                  25                  30
His Ser Thr Val Asp Arg Asn Ala Leu His Val Gln Leu Ala Asp Glu
         35                  40                  45
Ala Val Cys Ile Gly Glu Ala Ala Ser Ser Lys Ser Tyr Leu Asn Ile
     50                  55                  60
Pro Asn Ile Ile Ala Ala Leu Thr Arg Asn Ala Ser Ala Ile His
 65                  70                  75                  80
Pro Gly Tyr Gly Phe Leu Ala Glu Asn Ala Arg Phe Ala Glu Ile Cys
                 85                  90                  95
Ala Asp His His Leu Thr Phe Ile Gly Pro Ser Pro Asp Ser Ile Arg
            100                 105                 110
Ala Met Gly Asp Lys Ser Thr Ala Lys Glu Thr Met Gln Arg Val Gly
```

|     |     |     |     |     | 115 |     |     |     |     | 120 |     |     |     |     | 125 |     |     |     |
|---|---|---|---|---|---|---|---|---|---|---|---|---|---|---|---|---|---|---|

Val Pro Thr Ile Pro Gly Ser Asp Gly Leu Leu Thr Asp Val Asp Ser
130                     135                 140

Ala Ala Lys Val Ala Ala Glu Ile Gly Tyr Pro Val Met Ile Lys Ala
145                 150                 155                 160

Thr Ala Gly Gly Gly Gly Arg Gly Met Arg Leu Val Arg Glu Pro Ala
                    165             170             175

Asp Leu Glu Lys Leu Phe Leu Ala Ala Gln Gly Glu Ala Ala Ala Ala
            180                 185             190

Phe Gly Asn Pro Gly Leu Tyr Leu Glu Lys Phe Ile Asp Arg Pro Arg
        195             200             205

His Val Glu Phe Gln Ile Leu Ala Asp Ala Tyr Gly Asn Val Val Glu
    210             215             220

Leu Gly Glu Arg Asp Cys Ser Ile Gln Arg Arg His Gln Lys Leu Leu
225                 230             235             240

Glu Glu Ala Pro Ser Pro Ala Leu Ser Ala Asp Leu Arg Gln Lys Met
            245                 250             255

Gly Asp Ala Ala Val Lys Val Ala Gln Ala Ile Gly Tyr Ile Gly Ala
            260             265             270

Gly Thr Val Glu Phe Leu Val Asp Ala Thr Gly Asn Phe Tyr Phe Met
        275             280             285

Glu Met Asn Thr Arg Ile Gln Val Glu His Pro Val Thr Glu Met Ile
    290             295             300

Thr Gly Leu Asp Leu Ile Ala Glu Gln Ile Arg Ile Ala Gln Gly Glu
305             310             315             320

Ala Leu Arg Phe Arg Gln Ala Asp Ile Gln Leu Arg Gly His Ala Ile
                325             330             335

Glu Cys Arg Ile Asn Ala Glu Asp Pro Glu Tyr Asn Phe Arg Pro Asn
            340             345             350

Pro Gly Arg Ile Thr Gly Tyr Leu Pro Pro Gly Gly Pro Gly Val Arg
        355             360             365

Val Asp Ser His Val Tyr Thr Asp Tyr Glu Ile Pro Pro Tyr Tyr Asp
    370             375             380

Ser Leu Ile Gly Lys Leu Ile Val Trp Gly Ala Thr Arg Glu Glu Ala
385             390             395             400

Ile Ala Arg Met Gln Arg Ala Leu Arg Glu Gly Ala Ile Thr Gly Leu
            405             410             415

Pro Thr Thr Leu Ser Phe His Gln Leu Met Leu Gln Met Pro Glu Phe
            420             425             430

Leu Arg Gly Glu Leu Tyr Thr Asn Phe Val Glu Gln Val Met Leu Pro
        435             440             445

Arg Ile Leu Lys Ser
        450

( 2 ) INFORMATION FOR SEQ ID NO:7:

( i ) SEQUENCE CHARACTERISTICS:
    ( A ) LENGTH: 34 amino acids
    ( B ) TYPE: Amino acid
    ( C ) STRANDEDNESS: Single
    ( D ) TOPOLOGY: Linear ( i i ) MOLECULE TYPE: Peptide ( x i ) SEQUENCE DESCRIPTION: SEQ ID NO:7:

Met Asp Glu Pro Ser Pro Leu Ala Lys Thr Leu Glu Leu Asn Gln His
            5               10              15

Ser Arg Phe Ile Ile Gly Ser Val Ser Glu Asp Asn Ser Glu Asp Glu
              20                  25                  30

Ile Ser ( 2 ) INFORMATION FOR SEQ ID NO:8:

( i ) SEQUENCE CHARACTERISTICS:
        ( A ) LENGTH: 187 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:8:

Asn Leu Val Lys Leu Asp Leu Glu Glu Lys Glu Gly Ser Leu Ser Pro
              5                   10                  15

Ala Ser Val Ser Ser Asp Thr Leu Ser Asp Leu Gly Ile Ser Ala Leu
              20                  25                  30

Gln Asp Gly Leu Ala Phe His Met Arg Ser Ser Met Ser Gly Leu His
              35                  40                  45

Leu Val Lys Gln Gly Arg Asp Arg Lys Lys Ile Asp Ser Gln Arg Asp
        50                  55                  60

Phe Thr Val Ala Ser Pro Ala Glu Phe Val Thr Arg Phe Gly Gly Asn
65                  70                  75                  80

Lys Val Ile Glu Lys Val Leu Ile Ala Asn Asn Gly Ile Ala Ala Val
              85                  90                  95

Lys Cys Met Arg Ser Ile Arg Arg Trp Ser Tyr Glu Met Phe Arg Asn
              100                 105                 110

Glu Arg Ala Ile Arg Phe Val Val Met Val Thr Pro Glu Asp Leu Lys
              115                 120                 125

Ala Asn Ala Glu Tyr Ile Lys Met Ala Asp His Tyr Val Pro Val Pro
        130                 135                 140

Gly Gly Ala Asn Asn Asn Tyr Ala Asn Val Glu Leu Ile Leu Asp
145                 150                 155             160

Ile Ala Lys Arg Ile Pro Val Gln Ala Val Trp Ala Gly Trp Gly His
              165                 170                 175

Ala Ser Glu Asn Pro Lys Leu Pro Glu Leu Leu
              180                 185

INFORMATIONN FOR SEQ ID NO:9:

( i ) SEQUENCE CHARACTERISTICS:
        ( A ) LENGTH: 122 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:9:

Leu Lys Asn Gly Ile Ala Phe Met Gly Pro Pro Ser Gln Ala Met Trp
              5                   10                  15

Ala Leu Gly Asp Lys Ile Ala Ser Ser Ile Val Ala Gln Thr Ala Gly
              20                  25                  30

Ile Pro Thr Leu Pro Trp Ser Gly Ser Gly Leu Arg Val Asp Trp Gln
              35                  40                  45

Glu Asn Asp Phe Ser Lys Arg Ile Leu Asn Val Pro Gln Asp Leu Tyr
        50                  55                  60

Glu Lys Gly Tyr Val Lys Asp Val Asp Asp Gly Leu Lys Ala Ala Glu
65                  70                  75                  80

Glu Val Gly Tyr Pro Val Met Ile Lys Ala Ser Glu Gly Gly Gly Gly
            85                  90                  95

Lys Gly Ile Arg Lys Val Asn Asn Ala Asp Asp Phe Pro Asn Leu Phe
            100                 105                 110

Arg Gln Val Gln Ala Glu Val Pro Gly Ser
            115                 120

( 2 ) INFORMATION FOR SEQ ID NO:10:

( i ) SEQUENCE CHARACTERISTICS:
        ( A ) LENGTH: 86 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:10:

Pro Ile Phe Val Met Arg Leu Ala Lys Gln Ser Arg His Leu Glu Val
                5                   10                  15

Gln Ile Leu Ala Asp Gln Tyr Gly Asn Ala Ile Ser Leu Phe Gly Arg
            20                  25                  30

Asp Cys Ser Val Gln Arg Arg His Gln Lys Ile Ile Glu Glu Ala Pro
            35                  40                  45

Ala Ala Ile Ala Thr Pro Ala Val Phe Glu His Met Glu Gln Cys Ala
            50                  55                  60

Val Lys Leu Ala Lys Met Val Gly Tyr Val Ser Ala Gly Thr Val Glu
65                  70                  75                  80

Tyr Leu Tyr Ser Gln Asp
            85

( 2 ) INFORMATION FOR SEQ ID NO:11:

( i ) SEQUENCE CHARACTERISTICS:
        ( A ) LENGTH: 70 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:11:

Gly Ser Phe Tyr Phe Leu Glu Leu Asn Pro Arg Leu Gln Val Glu His
                5                   10                  15

Pro Cys Thr Glu Met Val Ala Asp Val Asn Leu Pro Ala Ala Gln Leu
            20                  25                  30

Gln Ile Ala Met Gly Ile Pro Leu Phe Arg Ile Lys Asp Ile Arg Met
            35                  40                  45

Met Tyr Gly Val Ser Pro Trp Gly Asp Ala Pro Ile Asp Phe Glu Asn
    50                  55                  60

Ser Ala His Val Pro Cys
65                  70

( 2 ) INFORMATION FOR SEQ ID NO:12:

( i ) SEQUENCE CHARACTERISTICS:
        ( A ) LENGTH: 20 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:12:

Pro Arg Gly His Val Ile Ala Ala Arg Ile Thr Ser Glu Asn Pro Asp
                    5                   10                  15
Glu Gly Phe Lys
            20

( 2 ) INFORMATION FOR SEQ ID NO:13:

( i ) SEQUENCE CHARACTERISTICS:
        ( A ) LENGTH: 21 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:13:

Pro Ser Ser Gly Thr Val Gln Glu Leu Asn Phe Arg Ser Asn Lys Asn
                    5                   10                  15
Val Trp Gly Tyr Phe
            20

( 2 ) INFORMATION FOR SEQ ID NO:14:

( i ) SEQUENCE CHARACTERISTICS:
        ( A ) LENGTH: 122 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:14:

Ser Val Ala Ala Ala Gly Gly Leu His Glu Phe Ala Asp Ser Gln Phe
                    5                   10                  15
Gly His Cys Phe Ser Trp Gly Glu Asn Arg Glu Glu Ala Ile Ser Asn
            20                  25                  30
Met Val Val Ala Leu Lys Glu Leu Ser Ile Arg Gly Asp Phe Arg Thr
        35                  40                  45
Thr Val Glu Tyr Leu Ile Lys Leu Leu Glu Thr Glu Ser Phe Gln Leu
    50                  55                  60
Asn Arg Ile Asp Thr Gly Trp Leu Asp Arg Leu Ile Ala Glu Lys Val
65                  70                  75                  80
Gln Ala Glu Arg Pro Asp Thr Met Leu Gly Val Val Cys Gly Ala Leu
                85                  90                  95
His Val Ala Asp Val Asn Leu Arg Asn Ser Ile Ser Asn Phe Leu His
            100                 105                 110
Ser Leu Glu Arg Gly Gln Val Leu Pro Ala
        115                 120

( 2 ) INFORMATION FOR SEQ ID NO:15:

( i ) SEQUENCE CHARACTERISTICS:
        ( A ) LENGTH: 190 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:15:

His Thr Leu Leu Asn Thr Val Asp Val Glu Leu Ile Tyr Glu Gly Ile

|  | 5 |  |  |  |  | 10 |  |  |  |  | 15 |  |  |
|---|---|---|---|---|---|---|---|---|---|---|---|---|---|
| Lys | Tyr | Val | Leu | Lys | Val | Thr | Arg | Gln | Ser | Pro | Asn | Ser | Tyr | Val | Val |
|  |  |  | 20 |  |  |  |  | 25 |  |  |  |  | 30 |
| Ile | Met | Asn | Gly | Ser | Cys | Val | Glu | Val | Asp | Val | His | Arg | Leu | Ser | Asp |
|  |  | 35 |  |  |  |  | 40 |  |  |  |  | 45 |
| Gly | Gly | Leu | Leu | Leu | Ser | Tyr | Asp | Gly | Ser | Ser | Tyr | Thr | Thr | Tyr | Met |
|  | 50 |  |  |  |  | 55 |  |  |  |  | 60 |
| Lys | Glu | Glu | Val | Asp | Arg | Tyr | Arg | Ile | Thr | Ile | Gly | Asn | Lys | Thr | Cys |
| 65 |  |  |  |  | 70 |  |  |  |  | 75 |  |  |  |  | 80 |
| Val | Phe | Glu | Lys | Glu | Asn | Asp | Pro | Ser | Val | Met | Arg | Ser | Pro | Ser | Ala |
|  |  |  |  | 85 |  |  |  |  | 90 |  |  |  |  | 95 |
| Gly | Lys | Leu | Ile | Gln | Tyr | Ile | Val | Glu | Asp | Gly | Gly | His | Val | Phe | Ala |
|  |  |  | 100 |  |  |  |  | 105 |  |  |  |  | 110 |
| Gly | Gln | Cys | Tyr | Ala | Glu | Ile | Glu | Val | Met | Lys | Met | Val | Met | Thr | Leu |
|  |  | 115 |  |  |  |  | 120 |  |  |  |  | 125 |
| Thr | Ala | Val | Glu | Ser | Gly | Cys | Ile | His | Tyr | Val | Lys | Arg | Pro | Gly | Ala |
|  |  | 130 |  |  |  |  | 135 |  |  |  |  | 140 |
| Ala | Leu | Asp | Pro | Gly | Cys | Val | Ile | Ala | Lys | Met | Gln | Leu | Asp | Asn | Pro |
| 145 |  |  |  |  | 150 |  |  |  |  | 155 |  |  |  |  | 160 |
| Ser | Lys | Val | Gln | Gln | Ala | Glu | Leu | His | Thr | Gly | Ser | Leu | Pro | Gln | Ile |
|  |  |  |  | 165 |  |  |  |  | 170 |  |  |  |  | 175 |
| Gln | Ser | Thr | Ala | Leu | Arg | Gly | Glu | Lys | Leu | His | Arg | Ile | Phe |
|  |  |  | 180 |  |  |  |  | 185 |  |  |  |  | 190 |

( 2 ) INFORMATION FOR SEQ ID NO:16:

( i ) SEQUENCE CHARACTERISTICS:
        ( A ) LENGTH: 37 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:16:

| Val | Met | Ile | Lys | Ala | Ser | Trp | Gly | Gly | Gly | Gly | Lys | Gly | Ile | Arg | Lys |
|---|---|---|---|---|---|---|---|---|---|---|---|---|---|---|---|
|  |  |  |  | 5 |  |  |  |  | 10 |  |  |  |  | 15 |
| Val | His | Asn | Asp | Asp | Glu | Val | Arg | Ala | Leu | Phe | Lys | Gln | Val | Gln | Gly |
|  |  |  | 20 |  |  |  |  | 25 |  |  |  |  | 30 |
| Glu | Val | Pro | Gly | Ser |
|  |  |  | 35 |

( 2 ) INFORMATION FOR SEQ ID NO:17:

( i ) SEQUENCE CHARACTERISTICS:
        ( A ) LENGTH: 187 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:17:

| Pro | Ile | Phe | Ile | Met | Lys | Val | Ala | Ser | Gln | Ser | Arg | His | Leu | Glu | Val |
|---|---|---|---|---|---|---|---|---|---|---|---|---|---|---|---|
|  |  |  |  | 5 |  |  |  |  | 10 |  |  |  |  | 15 |
| Gln | Leu | Leu | Cys | Asp | Lys | His | Gly | Asn | Val | Ala | Ala | Leu | His | Ser | Arg |
|  |  |  | 20 |  |  |  |  | 25 |  |  |  |  | 30 |
| Asp | Cys | Ser | Val | Gln | Arg | Arg | His | Gln | Lys | Ile | Ile | Glu | Glu | Gly | Pro |
|  |  | 35 |  |  |  |  | 40 |  |  |  |  | 45 |
| Ile | Thr | Val | Ala | Pro | Pro | Glu | Thr | Ile | Lys | Glu | Leu | Glu | Gln | Ala | Ala |

```
             50                       55                         60
Arg  Arg  Leu  Ala  Lys  Cys  Val  Gln  Tyr  Gln  Gly  Ala  Ala  Thr  Val  Glu
65                        70                         75                      80

Tyr  Leu  Tyr  Ser  Met  Glu  Thr  Gly  Glu  Tyr  Tyr  Phe  Leu  Glu  Leu  Asn
                     85                         90                      95

Pro  Arg  Leu  Gln  Val  Glu  His  Pro  Val  Thr  Glu  Trp  Ile  Ala  Glu  Ile
               100                      105                     110

Asn  Leu  Pro  Ala  Ser  Gln  Val  Val  Val  Gly  Met  Gly  Ile  Pro  Leu  Tyr
               115                      120                     125

Asn  Ile  Pro  Glu  Ile  Arg  Arg  Phe  Tyr  Gly  Ile  Glu  His  Gly  Gly  Gly
          130                      135                     140

Tyr  His  Ala  Trp  Lys  Glu  Ile  Ser  Ala  Val  Ala  Thr  Lys  Phe  Asp  Leu
145                      150                     155                         160

Asp  Lys  Ala  Gln  Ser  Val  Lys  Pro  Lys  Gly  His  Cys  Val  Ala  Val  Arg
                    165                     170                     175

Val  Thr  Ser  Glu  Asp  Pro  Asp  Asp  Gly  Phe  Lys
                    180                     185
```

( 2 ) INFORMATION FOR SEQ ID NO:18:

( i ) SEQUENCE CHARACTERISTICS:
        ( A ) LENGTH: 21 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:18:

```
Pro  Thr  Ser  Gly  Arg  Val  Glu  Glu  Leu  Asn  Phe  Lys  Ser  Lys  Pro  Asn
                     5                         10                      15

Val  Trp  Ala  Tyr  Phe
                     20
```

( 2 ) INFORMATION FOR SEQ ID NO:19:

( i ) SEQUENCE CHARACTERISTICS:
        ( A ) LENGTH: 122 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:19:

```
Ser  Val  Lys  Ser  Gly  Gly  Ala  Ile  His  Glu  Phe  Ser  Asp  Ser  Gln  Phe
                     5                         10                      15

Gly  His  Val  Phe  Ala  Phe  Gly  Glu  Ser  Arg  Ser  Leu  Ala  Ile  Ala  Asn
                    20                      25                      30

Met  Val  Leu  Gly  Leu  Lys  Glu  Ile  Gln  Ile  Arg  Gly  Glu  Ile  Arg  Thr
               35                      40                      45

Asn  Val  Asp  Tyr  Thr  Val  Asp  Leu  Leu  Asn  Ala  Ala  Glu  Tyr  Arg  Glu
          50                      55                      60

Asn  Met  Ile  His  Thr  Gly  Trp  Leu  Asp  Ser  Arg  Ile  Ala  Met  Arg  Val
65                      70                      75                      80

Arg  Ala  Glu  Arg  Pro  Pro  Trp  Tyr  Leu  Ser  Val  Val  Gly  Gly  Ala  Leu
                    85                      90                      95

Tyr  Glu  Ala  Ser  Ser  Arg  Ser  Ser  Val  Val  Thr  Asp  Tyr  Val  Gly
               100                     105                     110

Tyr  Leu  Ser  Lys  Gly  Gln  Ile  Pro  Pro  Lys
```

(2) INFORMATION FOR SEQ ID NO:20:

(i) SEQUENCE CHARACTERISTICS:
(A) LENGTH: 124 amino acids
(B) TYPE: Amino acid
(C) STRANDEDNESS: Single
(D) TOPOLOGY: Linear (ii) MOLECULE TYPE: Peptide (xi) SEQUENCE DESCRIPTION: SEQ ID NO:20:

| His | Ile | Ser | Leu | Val | Asn | Leu | Thr | Val | Thr | Leu | Asn | Ile | Asp | Gly | Ser |
|-----|-----|-----|-----|-----|-----|-----|-----|-----|-----|-----|-----|-----|-----|-----|-----|
|     |     |     |     | 5   |     |     |     |     | 10  |     |     |     |     | 15  |     |
| Lys | Tyr | Thr | Ile | Glu | Thr | Val | Arg | Gly | Gly | Pro | Arg | Ser | Tyr | Lys | Leu |
|     |     |     | 20  |     |     |     |     | 25  |     |     |     |     | 30  |     |     |
| Arg | Ile | Asn | Glu | Ser | Glu | Val | Glu | Ala | Glu | Ile | His | Phe | Leu | Arg | Asp |
|     |     | 35  |     |     |     |     | 40  |     |     |     |     | 45  |     |     |     |
| Gly | Gly | Leu | Leu | Met | Gln | Leu | Asp | Gly | Asn | Ser | His | Val | Ile | Tyr | Ala |
|     | 50  |     |     |     |     | 55  |     |     |     |     | 60  |     |     |     |     |
| Glu | Thr | Glu | Ala | Ala | Gly | Thr | Arg | Leu | Leu | Ile | Asn | Gly | Arg | Thr | Cys |
| 65  |     |     |     |     | 70  |     |     |     |     | 75  |     |     |     |     | 80  |
| Leu | Leu | Gln | Lys | Glu | His | Asp | Pro | Ser | Arg | Leu | Leu | Ala | Asp | Thr | Pro |
|     |     |     |     | 85  |     |     |     |     | 90  |     |     |     |     | 95  |     |
| Cys | Lys | Leu | Leu | Arg | Phe | Leu | Val | Ala | Asp | Gly | Ser | His | Val | Val | Ala |
|     |     |     | 100 |     |     |     |     | 105 |     |     |     |     | 110 |     |     |
| Asp | Thr | Pro | Tyr | Ala | Glu | Val | Glu | Ala | Met | Lys | Met |     |     |     |     |
|     |     | 115 |     |     |     |     | 120 |     |     |     |     |     |     |     |     |

(2) INFORMATION FOR SEQ ID NO:21:

(i) SEQUENCE CHARACTERISTICS:
(A) LENGTH: 222 amino acids
(B) TYPE: Amino acid
(C) STRANDEDNESS: Single
(D) TOPOLOGY: Linear (ii) MOLECULE TYPE: Peptide (xi) SEQUENCE DESCRIPTION: SEQ ID NO:21:

| Met | Glu | Glu | Ser | Ser | Gln | Pro | Ala | Lys | Pro | Leu | Glu | Met | Asn | Pro | His |
|-----|-----|-----|-----|-----|-----|-----|-----|-----|-----|-----|-----|-----|-----|-----|-----|
|     |     |     |     | 5   |     |     |     |     | 10  |     |     |     |     | 15  |     |
| Ser | Arg | Phe | Ile | Ile | Gly | Ser | Val | Ser | Glu | Asp | Asn | Ser | Glu | Asp | Glu |
|     |     |     | 20  |     |     |     |     | 25  |     |     |     |     | 30  |     |     |
| Thr | Ser | Ser | Leu | Val | Lys | Leu | Asp | Leu | Leu | Glu | Glu | Lys | Glu | Arg | Ser |
|     |     | 35  |     |     |     |     | 40  |     |     |     |     | 45  |     |     |     |
| Leu | Ser | Pro | Val | Ser | Val | Cys | Ser | Asp | Ser | Leu | Ser | Asp | Leu | Gly | Leu |
|     | 50  |     |     |     |     | 55  |     |     |     |     | 60  |     |     |     |     |
| Pro | Ser | Ala | Gln | Asp | Gly | Leu | Ala | Asn | His | Met | Arg | Pro | Ser | Met | Ser |
| 65  |     |     |     |     | 70  |     |     |     |     | 75  |     |     |     |     | 80  |
| Gly | Leu | His | Leu | Val | Lys | Gln | Gly | Arg | Asp | Arg | Lys | Lys | Val | Asp | Val |
|     |     |     |     | 85  |     |     |     |     | 90  |     |     |     |     | 95  |     |
| Gln | Arg | Asp | Phe | Thr | Val | Ala | Ser | Pro | Ala | Glu | Phe | Val | Thr | Arg | Phe |
|     |     |     | 100 |     |     |     |     | 105 |     |     |     |     | 110 |     |     |
| Gly | Gly | Asn | Arg | Val | Ile | Glu | Lys | Val | Leu | Ile | Ala | Asn | Asn | Gly | Ile |
|     |     | 115 |     |     |     |     | 120 |     |     |     |     | 125 |     |     |     |
| Ala | Ala | Val | Lys | Cys | Met | Arg | Ser | Ile | Arg | Arg | Trp | Ser | Tyr | Glu | Met |
|     |     | 130 |     |     |     |     | 135 |     |     |     |     | 140 |     |     |     |
| Phe | Arg | Asn | Glu | Arg | Ala | Ile | Arg | Phe | Val | Val | Met | Val | Thr | Pro | Glu |
| 145 |     |     |     |     | 150 |     |     |     |     | 155 |     |     |     |     | 160 |

```
Asp  Leu  Lys  Ala  Asn  Ala  Glu  Tyr  Ile  Lys  Met  Ala  Asp  His  Tyr  Val
               165                      170                     175

Pro  Val  Pro  Gly  Gly  Pro  Asn  Asn  Asn  Tyr  Ala  Asn  Val  Glu  Leu
               180                      185                     190

Ile  Leu  Asp  Ile  Ala  Lys  Arg  Ile  Pro  Val  Gln  Ala  Val  Trp  Ala  Gly
               195                      200                     205

Trp  Gly  His  Ala  Ser  Glu  Asn  Pro  Lys  Leu  Pro  Glu  Leu  Leu
     210                      215                     220
```

( 2 ) INFORMATION FOR SEQ ID NO:22:

( i ) SEQUENCE CHARACTERISTICS:
        ( A ) LENGTH: 122 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:22:

```
His  Lys  Asn  Gly  Ile  Ala  Phe  Met  Gly  Pro  Pro  Ser  Gln  Ala  Met  Trp
                    5                        10                      15

Ala  Leu  Gly  Asp  Lys  Ile  Ala  Ser  Ser  Ile  Val  Ala  Gln  Thr  Ala  Gly
               20                       25                      30

Ile  Pro  Thr  Leu  Pro  Trp  Asn  Gly  Ser  Gly  Leu  Arg  Val  Asp  Trp  Gln
          35                       40                      45

Glu  Asn  Asp  Leu  Gln  Lys  Arg  Ile  Leu  Asn  Val  Pro  Gln  Glu  Leu  Tyr
     50                       55                      60

Glu  Lys  Gly  Tyr  Val  Lys  Asp  Ala  Asp  Gly  Leu  Arg  Ala  Ala  Glu
65                       70                       75                      80

Glu  Val  Gly  Tyr  Pro  Val  Met  Ile  Lys  Ala  Ser  Glu  Gly  Gly  Gly  Gly
               85                       90                      95

Lys  Gly  Ile  Arg  Lys  Val  Asn  Asn  Ala  Asp  Asp  Phe  Pro  Asn  Leu  Phe
               100                      105                     110

Arg  Gln  Val  Gln  Ala  Glu  Val  Pro  Gly  Ser
          115                      120
```

( 2 ) INFORMATION FOR SEQ ID NO:23:

( i ) SEQUENCE CHARACTERISTICS:
        ( A ) LENGTH: 95 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:23:

```
Pro  Ile  Phe  Val  Met  Arg  Leu  Ala  Lys  Gln  Ser  Arg  His  Leu  Glu  Val
                    5                        10                      15

Gln  Ile  Leu  Ala  Asp  Gln  Tyr  Gly  Asn  Ala  Ile  Ser  Leu  Phe  Gly  Arg
               20                       25                      30

Asp  Cys  Ser  Val  Gln  Arg  Arg  His  Gln  Lys  Ile  Ile  Glu  Glu  Ala  Gly
               35                       40                      45

Leu  Arg  Ala  Ala  Glu  Glu  Val  Gly  Tyr  Pro  Val  Met  Ile  Lys  Ala  Ser
     50                       55                      60

Glu  Gly  Gly  Gly  Gly  Lys  Gly  Ile  Arg  Lys  Val  Asn  Asn  Ala  Asp  Asp
65                       70                       75                      80

Phe  Pro  Asn  Leu  Phe  Arg  Gln  Val  Gln  Ala  Glu  Val  Pro  Gly  Ser
               85                       90                      95
```

(2) INFORMATION FOR SEQ ID NO:24:

(i) SEQUENCE CHARACTERISTICS:
        (A) LENGTH: 86 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:24:

```
Pro Ile Phe Val Met Arg Leu Ala Lys Gln Ser Arg His Leu Glu Val
                 5                  10                 15
Gln Ile Leu Ala Asp Gln Tyr Gly Asn Ala Ile Ser Leu Phe Gly Arg
             20                  25                 30
Asp Cys Ser Val Gln Arg Arg His Gln Lys Ile Ile Glu Glu Ala Pro
         35                  40                 45
Ala Ser Ile Ala Thr Ser Val Val Phe Glu His Met Glu Gln Cys Ala
     50                  55                 60
Val Lys Leu Ala Lys Met Val Gly Tyr Val Ser Ala Gly Thr Val Glu
 65                 70                  75                 80
Tyr Leu Tyr Ser Gln Asp
                 85
```

(2) INFORMATION FOR SEQ ID NO:25:

(i) SEQUENCE CHARACTERISTICS:
        (A) LENGTH: 70 amino acids
        (B) TYPE: Amino acids
        (C) STRANDEDNESS: Single
        (D) TOPOLOGY: Linear (ii) MOLECULE TYPE: Peptide (xi) SEQUENCE DESCRIPTION: SEQ ID NO:25:

```
Gly Ser Phe Tyr Phe Leu Glu Leu Asn Pro Arg Leu Gln Val Glu His
                 5                  10                 15
Pro Cys Thr Glu Met Val Ala Asp Val Asn Leu Pro Ala Ala Gln Leu
             20                  25                 30
Gln Ile Ala Met Gly Ile Pro Leu His Arg Ile Lys Asp Ile Arg Val
         35                  40                 45
Met Tyr Gly Val Ser Pro Trp Gly Asp Gly Ser Ile Asp Phe Glu Asn
     50                  55                 60
Ser Ala His Val Pro Cys
 65                 70
```

(2) INFORMATION FOR SEQ ID NO:26:

(i) SEQUENCE CHARACTERISTICS:
        (A) LENGTH: 20 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:26:

```
Pro Arg Gly His Val Ile Ala Ala Arg Ile Thr Ser Glu Asn Pro Asp
                 5                  10                 15
Glu Gly Phe Lys
         20
```

(2) INFORMATION FOR SEQ ID NO:27:

( i ) SEQUENCE CHARACTERISTICS:
  ( A ) LENGTH: 21 amino acids
  ( B ) TYPE: Amino acid
  ( C ) STRANDEDNESS: Single
  ( D ) TOPOLOGY: Linear ( i i ) MOLECULE TYPE: Peptide ( x i ) SEQUENCE DESCRIPTION: SEQ ID NO:27:

| Pro | Ser | Ser | Gly | Thr | Val | Gln | Glu | Leu | Asn | Phe | Arg | Ser | Asn | Lys | Asn |
|---|---|---|---|---|---|---|---|---|---|---|---|---|---|---|---|
| | | | | 5 | | | | | 10 | | | | | 15 | |

| Val | Trp | Gly | Tyr | Phe |
|---|---|---|---|---|
| | | | | 20 |

( 2 ) INFORMATION FOR SEQ ID NO:28:

( i ) SEQUENCE CHARACTERISTICS:
  ( A ) LENGTH: 122 amino acids
  ( B ) TYPE: Amino acid
  ( C ) STRANDEDNESS: Single
  ( D ) TOPOLOGY: Linear ( i i ) MOLECULE TYPE: Peptide ( x i ) SEQUENCE DESCRIPTION: SEQ ID NO:28:

| Ser | Val | Ala | Ala | Ala | Gly | Gly | Leu | His | Glu | Phe | Ala | Asp | Ser | Gln | Phe |
|---|---|---|---|---|---|---|---|---|---|---|---|---|---|---|---|
| | | | | 5 | | | | | 10 | | | | | 15 | |

| Gly | His | Cys | Phe | Ser | Trp | Gly | Glu | Asn | Arg | Glu | Glu | Ala | Ile | Ser | Asn |
|---|---|---|---|---|---|---|---|---|---|---|---|---|---|---|---|
| | | | 20 | | | | | 25 | | | | | 30 | | |

| Met | Val | Val | Ala | Leu | Lys | Glu | Leu | Ser | Ile | Arg | Gly | Asp | Phe | Arg | Thr |
|---|---|---|---|---|---|---|---|---|---|---|---|---|---|---|---|
| | | 35 | | | | | 40 | | | | | 45 | | | |

| Thr | Val | Glu | Tyr | Leu | Ile | Lys | Leu | Leu | Glu | Thr | Glu | Ser | Phe | Gln | Gln |
|---|---|---|---|---|---|---|---|---|---|---|---|---|---|---|---|
| | 50 | | | | | 55 | | | | | 60 | | | | |

| Asn | Arg | Ile | Asp | Thr | Gly | Trp | Leu | Asp | Arg | Leu | Ile | Ala | Glu | Lys | Val |
|---|---|---|---|---|---|---|---|---|---|---|---|---|---|---|---|
| 65 | | | | | 70 | | | | | 75 | | | | | 80 |

| Gln | Ala | Glu | Arg | Pro | Asp | Thr | Met | Leu | Gly | Val | Val | Cys | Gly | Ala | Leu |
|---|---|---|---|---|---|---|---|---|---|---|---|---|---|---|---|
| | | | | 85 | | | | | 90 | | | | | 95 | |

| His | Val | Ala | Asp | Val | Ser | Phe | Arg | Asn | Ser | Val | Ser | Asn | Phe | Leu | His |
|---|---|---|---|---|---|---|---|---|---|---|---|---|---|---|---|
| | | | 100 | | | | | 105 | | | | | 110 | | |

| Ser | Leu | Glu | Arg | Gly | Gln | Val | Leu | Pro | Ala |
|---|---|---|---|---|---|---|---|---|---|
| | | 115 | | | | | 120 | | |

( 2 ) INFORMATION FOR SEQ ID NO:29:

( i ) SEQUENCE CHARACTERISTICS:
  ( A ) LENGTH: 90 amino acids
  ( B ) TYPE: Amino acid
  ( C ) STRANDEDNESS: Single
  ( D ) TOPOLOGY: Linear ( i i ) MOLECULE TYPE: Peptide ( x i ) SEQUENCE DESCRIPTION: SEQ ID NO:29:

| Met | Val | Val | Ala | Leu | Lys | Glu | Leu | Ser | Ile | Arg | Gly | Asp | Phe | Arg | Thr |
|---|---|---|---|---|---|---|---|---|---|---|---|---|---|---|---|
| | | | | 5 | | | | | 10 | | | | | 15 | |

| Thr | Val | Glu | Tyr | Leu | Ile | Lys | Leu | Leu | Glu | Thr | Glu | Ser | Phe | Gln | Gln |
|---|---|---|---|---|---|---|---|---|---|---|---|---|---|---|---|
| | | | 20 | | | | | 25 | | | | | 30 | | |

| Asn | Arg | Ile | Asp | Thr | Gly | Trp | Leu | Asp | Arg | Leu | Ile | Ala | Glu | Lys | Val |
|---|---|---|---|---|---|---|---|---|---|---|---|---|---|---|---|
| | | | 35 | | | | | 40 | | | | | 45 | | |

| Gln | Ala | Glu | Arg | Pro | Asp | Thr | Met | Leu | Gly | Val | Val | Cys | Gly | Ala | Leu |
|---|---|---|---|---|---|---|---|---|---|---|---|---|---|---|---|
| | 50 | | | | | 55 | | | | | 60 | | | | |

| His | Val | Ala | Asp | Val | Ser | Phe | Arg | Asn | Ser | Val | Ser | Asn | Phe | Leu | His |
|---|---|---|---|---|---|---|---|---|---|---|---|---|---|---|---|

65                     70                    75                    80

Ser  Leu  Glu  Arg  Gly  Gln  Val  Leu  Pro  Ala
                    85                         90

(2) INFORMATION FOR SEQ ID NO:30:

(i) SEQUENCE CHARACTERISTICS:
        (A) LENGTH: 190 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:30:

His  Thr  Leu  Leu  Asn  Thr  Val  Asp  Val  Glu  Leu  Ile  Tyr  Glu  Gly  Arg
                    5                         10                        15

Lys  Tyr  Val  Leu  Lys  Val  Thr  Arg  Gln  Ser  Pro  Asn  Ser  Tyr  Val  Val
                    20                        25                        30

Ile  Met  Asn  Ser  Ser  Cys  Val  Glu  Val  Asp  Val  His  Arg  Leu  Ser  Asp
               35                        40                   45

Gly  Gly  Leu  Leu  Leu  Ser  Tyr  Asp  Gly  Ser  Ser  Tyr  Thr  Thr  Tyr  Met
          50                        55                        60

Lys  Glu  Glu  Val  Asp  Arg  Tyr  Arg  Ile  Thr  Ile  Gly  Asn  Lys  Thr  Cys
65                        70                        75                        80

Val  Phe  Glu  Lys  Glu  Asn  Asp  Pro  Ser  Ile  Leu  Arg  Ser  Pro  Ser  Ala
                    85                        90                        95

Gly  Lys  Leu  Ile  Gln  Tyr  Val  Val  Glu  Asp  Gly  Gly  His  Val  Phe  Ala
                    100                       105                       110

Gly  Gln  Cys  Phe  Ala  Glu  Ile  Glu  Val  Met  Lys  Met  Val  Met  Thr  Leu
               115                       120                  125

Thr  Ala  Gly  Glu  Ser  Gly  Cys  Ile  His  Tyr  Val  Lys  Arg  Pro  Gly  Ala
          130                       135                       140

Val  Leu  Asp  Pro  Gly  Cys  Val  Ile  Ala  Lys  Leu  Gln  Leu  Asp  Asp  Pro
145                       150                       155                       160

Ser  Arg  Val  Gln  Gln  Ala  Glu  Leu  His  Thr  Gly  Thr  Leu  Pro  Gln  Ile
                    165                       170                       175

Gln  Ser  Thr  Ala  Leu  Arg  Gly  Glu  Lys  Leu  His  Arg  Ile  Phe
               180                       185                  190

(2) INFORMATION FOR SEQ ID NO:31:

(i) SEQUENCE CHARACTERISTICS:
        (A) LENGTH: 41 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:31:

Met  Ser  Glu  Glu  Ser  Leu  Phe  Glu  Ser  Ser  Pro  Gln  Lys  Met  Glu  Tyr
                    5                         10                        15

Glu  Ile  Thr  Asn  Tyr  Ser  Glu  Arg  His  Thr  Glu  Leu  Pro  Gly  His  Phe
                    20                        25                        30

Ile  Gly  Leu  Asn  Thr  Val  Asp  Lys  Leu
               35                        40

(2) INFORMATION FOR SEQ ID NO:32:

(i) SEQUENCE CHARACTERISTICS:

( A ) LENGTH: 74 amino acids
( B ) TYPE: Amino acid
( C ) STRANDEDNESS: Single
( D ) TOPOLOGY: Linear ( i i ) MOLECULE TYPE: Peptide ( x i ) SEQUENCE DESCRIPTION: SEQ ID NO:32:

```
Ala Asp Val Asp Ala Val Trp Ala Gly Trp Gly His Ala Ser Glu Asn
                 5                  10                  15
Pro Leu Leu Pro Glu Lys Leu Ser Gln Ser Lys Arg Lys Val Ile Phe
                20                  25                  30
Ile Gly Pro Pro Gly Asn Ala Met Arg Ser Leu Gly Asp Lys Ile Ser
            35                  40                  45
Ser Thr Thr Ile Val Ala Gln Ser Ala Lys Val Pro Cys Ile Pro Trp
50                      55                  60
Ser Gly Thr Thr Gly Val Asp Thr Val His
65                  70
```

( 2 ) INFORMATION FOR SEQ ID NO:33:

( i ) SEQUENCE CHARACTERISTICS:
( A ) LENGTH: 73 amino acids
( B ) TYPE: Amino acid
( C ) STRANDEDNESS: Single
( D ) TOPOLOGY: Linear ( i i ) MOLECULE TYPE: Peptide ( x i ) SEQUENCE DESCRIPTION: SEQ ID NO:33:

```
Val Asp Glu Lys Thr Gly Leu Val Ser Val Asp Asp Ile Tyr Gln
                 5                  10                  15
Lys Gly Cys Cys Thr Ser Pro Glu Asp Gly Leu Gln Lys Ala Lys Arg
                20                  25                  30
Ile Gly Phe Pro Val Met Ile Lys Ala Ser Glu Gly Gly Gly Gly Lys
            35                  40                  45
Gly Ile Arg Gln Val Glu Arg Glu Glu Asp Phe Ile Ala Leu Tyr His
50                      55                  60
Gln Ala Ala Asn Glu Ile Pro Gly Ser
65                  70
```

( 2 ) INFORMATION FOR SEQ ID NO:34:

( i ) SEQUENCE CHARACTERISTICS:
( A ) LENGTH: 157 amino acids
( B ) TYPE: Amino acid
( C ) STRANDEDNESS: Single
( D ) TOPOLOGY: Linear ( i i ) MOLECULE TYPE: Peptide ( x i ) SEQUENCE DESCRIPTION: SEQ ID NO:34:

```
Pro Ile Phe Ile Met Lys Leu Ala Gly Arg Ala Arg His Leu Glu Val
                 5                  10                  15
Gln Leu Leu Ala Asp Gln Tyr Gly Thr Asn Ile Ser Leu Phe Gly Arg
                20                  25                  30
Asp Cys Ser Val Gln Arg Arg His Gln Lys Ile Ile Glu Glu Ala Pro
            35                  40                  45
Val Thr Ile Ala Lys Ala Glu Thr Phe His Glu Met Glu Lys Ala Ala
50                      55                  60
Val Arg Leu Gly Lys Leu Val Gly Tyr Val Ser Ala Gly Thr Val Glu
65                  70                  75                  80
```

```
Tyr  Leu  Tyr  Ser  His  Asp  Asp  Gly  Lys  Phe  Tyr  Phe  Leu  Glu  Leu  Asn
                    85                  90                       95

Pro  Arg  Leu  Gln  Val  Glu  His  Pro  Thr  Thr  Glu  Met  Val  Ser  Gly  Val
               100                      105                      110

Asn  Leu  Pro  Ala  Ala  Gln  Leu  Gln  Ile  Ala  Met  Gly  Ile  Pro  Met  His
               115                 120                      125

Arg  Ile  Ser  Asp  Ile  Arg  Thr  Leu  Tyr  Gly  Met  Asn  Pro  His  Ser  Ala
          130                 135                 140

Ser  Glu  Ile  Asp  Phe  Glu  Phe  Lys  Thr  Gln  Asp  Ala  Thr
145                      150                 155
```

( 2 ) INFORMATION FOR SEQ ID NO:35:

( i ) SEQUENCE CHARACTERISTICS:
        ( A ) LENGTH: 27 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:35:

```
Lys  Lys  Gln  Arg  Arg  Pro  Ile  Pro  Lys  Gly  His  Cys  Thr  Ala  Cys  Arg
                    5                        10                       15

Ile  Thr  Ser  Glu  Asp  Pro  Asn  Asp  Gly  Phe  Lys
                    20                   25
```

( 2 ) INFORMATION FOR SEQ ID NO:36:

( i ) SEQUENCE CHARACTERISTICS:
        ( A ) LENGTH: 21 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:36:

```
Pro  Ser  Gly  Gly  Thr  Leu  His  Glu  Leu  Asn  Phe  Arg  Ser  Ser  Ser  Asn
                    5                        10                       15

Val  Trp  Gly  Tyr  Phe
                    20
```

( 2 ) INFORMATION FOR SEQ ID NO:37:

( i ) SEQUENCE CHARACTERISTICS:
        ( A ) LENGTH: 122 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:37:

```
Ser  Val  Gly  Asn  Asn  Gly  Asn  Ile  His  Ser  Phe  Ser  Asp  Ser  Gln  Phe
               5                        10                       15

Gly  His  Ile  Phe  Ala  Phe  Gly  Glu  Asn  Arg  Gln  Ala  Ser  Arg  Lys  His
               20                       25                       30

Met  Val  Val  Ala  Leu  Lys  Glu  Leu  Ser  Ile  Arg  Gly  Asp  Phe  Arg  Thr
               35                       40                       45

Thr  Val  Glu  Tyr  Leu  Ile  Lys  Leu  Leu  Glu  Thr  Glu  Asp  Phe  Glu  Asp
     50                       55                       60

Asn  Thr  Ile  Thr  Thr  Gly  Trp  Leu  Asp  Asp  Leu  Ile  Thr  His  Lys  Met
65                       70                       75                       80
```

Thr Ala Glu Lys Pro Asp Pro Thr Leu Ala Val Ile Cys Gly Ala Ala
                85                  90                  95

Thr Lys Ala Phe Leu Ala Ser Glu Glu Ala Arg His Lys Tyr Ile Glu
            100                 105                 110

Ser Leu Gln Lys Gly Gln Val Leu Ser Lys
            115                 120

( 2 ) INFORMATION FOR SEQ ID NO:38:

( i ) SEQUENCE CHARACTERISTICS:
        ( A ) LENGTH: 190 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:38:

Asp Leu Leu Gln Thr Met Phe Pro Val Asp Phe Ile His Glu Gly Lys
                5                   10                  15

Arg Tyr Lys Phe Thr Val Ala Lys Ser Gly Asn Asp Arg Tyr Thr Leu
            20                  25                  30

Phe Ile Asn Gly Ser Lys Cys Asp Ile Ile Leu Arg Gln Leu Ser Asp
            35                  40                  45

Gly Gly Leu Leu Ile Ala Ile Gly Gly Lys Ser His Thr Ile Tyr Trp
    50                  55                  60

Lys Glu Glu Val Ala Ala Thr Arg Leu Ser Val Asp Ser Met Thr Thr
65                  70                  75                  80

Leu Leu Glu Val Glu Asn Asp Pro Thr Gln Leu Arg Thr Pro Ser Pro
                85                  90                  95

Gly Lys Leu Val Lys Phe Leu Val Glu Asn Gly Glu His Ile Ile Lys
            100                 105                 110

Gly Gln Pro Tyr Ala Glu Ile Glu Val Met Lys Met Gln Met Pro Leu
            115                 120                 125

Val Ser Gln Glu Asn Gly Ile Val Gln Leu Leu Lys Gln Pro Gly Ser
    130                 135                 140

Thr Ile Val Ala Gly Asp Ile Met Ala Ile Met Thr Leu Asp Asp Pro
145                 150                 155                 160

Ser Lys Val Lys His Ala Leu Pro Phe Glu Gly Met Leu Pro Asp Phe
                165                 170                 175

Gly Ser Pro Val Ile Glu Gly Thr Lys Pro Ala Tyr Lys Phe
            180                 185                 190

( 2 ) INFORMATION FOR SEQ ID NO:39:

( i ) SEQUENCE CHARACTERISTICS:
        ( A ) LENGTH: 37 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:39:

Met Arg Phe Asn Lys Ile Leu Ile Ala Asn Arg Gly Glu Ile Ala Leu
                5                   10                  15

Arg Ile Leu Arg Thr Cys Glu Glu Leu Gly Ile Gly Thr Ile Ala Val
            20                  25                  30

His Ser Thr Val Asp
            35

( 2 ) INFORMATION FOR SEQ ID NO:40:

( i ) SEQUENCE CHARACTERISTICS:
    ( A ) LENGTH: 21 amino acids
    ( B ) TYPE: Amino acid
    ( C ) STRANDEDNESS: Single
    ( D ) TOPOLOGY: Linear ( i i ) MOLECULE TYPE: Peptide ( x i ) SEQUENCE DESCRIPTION: SEQ ID NO:40:

```
Arg  Asn  Ala  Leu  His  Val  Gln  Leu  Ala  Asp  Glu  Ala  Val  Cys  Ile  Gly
              5                        10                       15
Glu  Ala  Ala  Ser  Ser
              20
```

( 2 ) INFORMATION FOR SEQ ID NO:41:

( i ) SEQUENCE CHARACTERISTICS:
    ( A ) LENGTH: 38 amino acids
    ( B ) TYPE: Amino acid
    ( C ) STRANDEDNESS: Single
    ( D ) TOPOLOGY: Linear ( i i ) MOLECULE TYPE: Peptide ( x i ) SEQUENCE DESCRIPTION: SEQ ID NO:41:

```
Lys  Ser  Tyr  Leu  Asn  Ile  Pro  Asn  Ile  Ala  Ala  Ala  Leu  Thr  Arg
              5                        10                       15
Asn  Ala  Ser  Ala  Ile  His  Pro  Gly  Tyr  Gly  Phe  Leu  Ala  Glu  Asn  Ala
                   20                        25                       30
Arg  Phe  Ala  Glu  Ile  Cys
              35
```

( 2 ) INFORMATION FOR SEQ ID NO:42:

( i ) SEQUENCE CHARACTERISTICS:
    ( A ) LENGTH: 41 amino acids
    ( B ) TYPE: Amino acid
    ( C ) STRANDEDNESS: Single
    ( D ) TOPOLOGY: Linear ( i i ) MOLECULE TYPE: Peptide ( x i ) SEQUENCE DESCRIPTION: SEQ ID NO:42:

```
Ala  Asp  His  His  Leu  Thr  Phe  Ile  Gly  Pro  Ser  Pro  Asp  Ser  Ile  Arg
                   5                        10                       15
Ala  Met  Gly  Asp  Lys  Ser  Thr  Ala  Lys  Glu  Thr  Met  Gln  Arg  Val  Gly
              20                        25                       30
Val  Pro  Thr  Ile  Pro  Gly  Ser  Asp  Gly
              35                  40
```

( 2 ) INFORMATION FOR SEQ ID NO:43:

( i ) SEQUENCE CHARACTERISTICS:
    ( A ) LENGTH: 143 amino acids
    ( B ) TYPE: Amino acid
    ( C ) STRANDEDNESS: Single
    ( D ) TOPOLOGY: Linear ( i i ) MOLECULE TYPE: Peptide ( x i ) SEQUENCE DESCRIPTION: SEQ ID NO:43:

```
Leu  Leu  Thr  Asp  Val  Asp  Ser  Ala  Ala  Lys  Val  Ala  Ala  Glu  Ile  Gly
              5                        10                       15
```

Tyr Pro Val Met Ile Lys Ala Thr Ala Gly Gly Gly Gly Arg Gly Met
         20              25                     30

Arg Leu Val Arg Glu Pro Ala Asp Leu Glu Lys Leu Phe Leu Ala Ala
         35              40              45

Gln Gly Glu Ala Glu Ala Ala Phe Gly Asn Pro Gly Leu Tyr Leu Glu
    50              55              60

Lys Phe Ile Asp Arg Pro Arg His Val Glu Phe Gln Ile Leu Ala Asp
65              70              75              80

Ala Tyr Gly Asn Val Val His Leu Gly Glu Arg Asp Cys Ser Ile Gln
            85              90              95

Arg Arg His Gln Lys Leu Leu Glu Glu Ala Pro Ser Pro Ala Leu Ser
            100             105             110

Ala Asp Leu Arg Gln Lys Met Gly Asp Ala Ala Val Lys Val Ala Gln
        115             120             125

Ala Ile Gly Tyr Ile Gly Ala Gly Thr Val Glu Phe Leu Val Asp
        130             135             140

( 2 ) INFORMATION FOR SEQ ID NO:44:

( i ) SEQUENCE CHARACTERISTICS:
        ( A ) LENGTH: 50 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:44:

Ala Thr Gly Asn Phe Tyr Phe Met Glu Met Asn Thr Arg Ile Gln Val
            5               10              15

Glu His Pro Val Thr Glu Met Ile Thr Gly Leu Asp Leu Ile Ala Glu
         20              25              30

Gln Ile Arg Ile Ala Gln Gly Glu Ala Leu Arg Phe Arg Gln Ala Asp
        35              40              45

Ile Gln
50

( 2 ) INFORMATION FOR SEQ ID NO:45:

( i ) SEQUENCE CHARACTERISTICS:
        ( A ) LENGTH: 19 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:45:

Leu Arg Gly His Ala Ile Glu Cys Arg Ile Asn Ala Glu Asp Pro Glu
            5               10              15

Tyr Asn Phe ( 2 ) INFORMATION FOR SEQ ID NO:46:

( i ) SEQUENCE CHARACTERISTICS:
        ( A ) LENGTH: 9 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:46:

Arg Pro Asn Pro Gly Arg Ile Thr Gly
                    5

( 2 ) INFORMATION FOR SEQ ID NO:47:

( i ) SEQUENCE CHARACTERISTICS:
        ( A ) LENGTH: 7 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:47:

Pro Gly Val Arg Val Asp Ser
                5

( 2 ) INFORMATION FOR SEQ ID NO:48:

( i ) SEQUENCE CHARACTERISTICS:
        ( A ) LENGTH: 44 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:48:

His Val Tyr Thr Asp Tyr Glu Ile Pro Pro Tyr Tyr Asp Ser Leu Ile
                5                   10                  15

Gly Lys Leu Ile Val Trp Gly Ala Thr Arg Glu Glu Ala Ile Ala Arg
            20                  25                  30

Met Gln Arg Ala Leu Arg Glu Cys Ala Ile Thr Gly
        35                  40

INFORMATION FOR SEQ ID NO:49:

( i ) SEQUENCE CHARACTERISTICS:
        ( A ) LENGTH: 38 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:49:

Leu Pro Thr Thr Leu Ser Phe His Gln Leu Met Leu Gln Met Pro Glu
                5                   10                  15

Phe Leu Arg Gly Glu Leu Tyr Thr Asn Phe Val Glu Gln Val Met Leu
            20                  25                  30

Pro Arg Ile Leu Lys Ser
            35

( 2 ) INFORMATION FOR SEQ ID NO:50:

( i ) SEQUENCE CHARACTERISTICS:
        ( A ) LENGTH: 37 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:50:

Met Lys Phe Asp Lys Ile Leu Ile Ala Asn Arg Gly Glu Ile Ala Leu
                5                   10                  15

Arg Ile Leu Arg Ala Cys Glu Glu Met Gly Ile Ala Thr Ile Ala Val 5,539,092

| 20 | 25 | 30 |

His Ser Thr Val Asp
35

( 2 ) INFORMATION FOR SEQ ID NO:51:

( i ) SEQUENCE CHARACTERISTICS:
        ( A ) LENGTH: 21 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:51:

Arg Asn Ala Leu His Val Gln Leu Ala Asp Glu Ala Val Cys Ile Gly
            5                      10                  15

Glu Pro Ala Ser Ala
        20

( 2 ) INFORMATION FOR SEQ ID NO:52:

( i ) SEQUENCE CHARACTERISTICS:
        ( A ) LENGTH: 38 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:52:

Lys Ser Tyr Leu Asn Ile Pro Asn Ile Ile Ala Ala Ala Leu Thr Arg
            5                      10                  15

Asn Ala Ser Ala Ile His Pro Gly Tyr Gly Phe Leu Ser Glu Asn Ala
        20                  25                  30

Lys Phe Ala Glu Ile Cys
        35

( 2 ) INFORMATION FOR SEQ ID NO:53:

( i ) SEQUENCE CHARACTERISTICS:
        ( A ) LENGTH: 42 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:53:

Ala Asp His His Ile Ala Phe Ile Gly Pro Thr Pro Glu Ala Ile Arg
            5                      10                  15

Leu Met Gly Asp Lys Ser Thr Ala Lys Glu Thr Met Gln Lys Ala Gly
        20                  25                  30

Val Pro Thr Val Pro Gly Ser Glu Gly Leu
        35                  40

( 2 ) INFORMATION FOR SEQ ID NO:54:

( i ) SEQUENCE CHARACTERISTICS:
        ( A ) LENGTH: 142 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:54:

Val Glu Thr Glu Gln Glu Gly Leu Glu Leu Ala Lys Asp Ile Gly Tyr
                  5                  10                 15

Pro Val Met Ile Lys Ala Thr Ala Gly Gly Gly Arg Gly Met Arg
                20              25              30

Leu Val Arg Ser Pro Asp Glu Phe Val Lys Leu Phe Leu Ala Ala Gln
            35              40              45

Gly Glu Ala Gly Ala Ala Phe Gly Asn Ala Gly Val Tyr Ile Glu Lys
    50              55              60

Phe Ile Glu Arg Pro Arg His Ile Glu Phe Gln Ile Leu Ala Asp Asn
65              70              75                          80

Tyr Gly Asn Val Ile His Leu Gly Glu Arg Asp Cys Ser Ile Gln Arg
                85              90                      95

Arg Asn Gln Lys Leu Leu Glu Glu Ala Pro Ser Pro Ala Leu Asp Ser
            100             105             110

Asp Leu Arg Glu Lys Met Gly Gln Ala Ala Val Lys Ala Ala Gln Phe
            115             120             125

Ile Asn Tyr Ala Gly Ala Gly Thr Ile Glu Phe Leu Leu Asp
        130             135             140

( 2 ) INFORMATION FOR SEQ ID NO:55:

( i ) SEQUENCE CHARACTERISTICS:
    ( A ) LENGTH: 50 amino acids
    ( B ) TYPE: Amino acid
    ( C ) STRANDEDNESS: Single
    ( D ) TOPOLOGY: Linear ( i i ) MOLECULE TYPE: Peptide ( x i ) SEQUENCE DESCRIPTION: SEQ ID NO:55:

Arg Ser Gly Gln Phe Tyr Phe Met Glu Met Asn Thr Arg Ile Gln Val
                5               10              15

Glu His Pro Val Thr Glu Met Val Thr Gly Val Asp Leu Leu Val Glu
            20              25              30

Gln Ile Arg Ile Ala Gln Gly Glu Arg Leu Arg Leu Thr Gln Asp Gln
        35              40              45

Val Val
50

( 2 ) INFORMATION FOR SEQ ID NO:56:

( i ) SEQUENCE CHARACTERISTICS:
    ( A ) LENGTH: 19 amino acids
    ( B ) TYPE: Amino acid
    ( C ) STRANDEDNESS: Single
    ( D ) TOPOLOGY: Linear ( i i ) MOLECULE TYPE: Peptide ( x i ) SEQUENCE DESCRIPTION: SEQ ID NO:56:

Leu Arg Gly His Ala Ile Glu Cys Arg Ile Asn Ala Glu Asp Pro Asp
                5               10              15

His Asp Phe ( 2 ) INFORMATION FOR SEQ ID NO:57:

( i ) SEQUENCE CHARACTERISTICS:
    ( A ) LENGTH: 9 amino acids
    ( B ) TYPE: Amino acid
    ( C ) STRANDEDNESS: Single
    ( D ) TOPOLOGY: Linear ( i i ) MOLECULE TYPE: Peptide ( x i ) SEQUENCE DESCRIPTION: SEQ ID NO:57:

Arg Pro Ala Pro Gly Arg Ile Ser Gly
                 5

( 2 ) INFORMATION FOR SEQ ID NO:58:

( i ) SEQUENCE CHARACTERISTICS:
        ( A ) LENGTH: 6 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:58:

Tyr Leu Pro Pro Gly Gly
                 5

( 2 ) INFORMATION FOR SEQ ID NO:59:

( i ) SEQUENCE CHARACTERISTICS:
        ( A ) LENGTH: 7 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:59:

Pro Gly Val Arg Ile Asp Ser
                 5

( 2 ) INFORMATION FOR SEQ ID NO:60:

( i ) SEQUENCE CHARACTERISTICS:
        ( A ) LENGTH: 44 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:60:

His Val Tyr Thr Asp Tyr Gln Ile Pro Pro Tyr Tyr Asp Ser Leu Ile
                 5                  10                  15
Gly Lys Leu Ile Val Trp Gly Pro Asp Arg Ala Thr Ala Ile Asn Arg
                20                  25                  30
Met Lys Arg Ala Leu Arg Glu Cys Ala Ile Thr Gly
                35                  40

( 2 ) INFORMATION FOR SEQ ID NO:61:

( i ) SEQUENCE CHARACTERISTICS:
        ( A ) LENGTH: 154 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:61:

Leu Pro Thr Thr Ile Gly Phe His Gln Arg Ile Met Glu Asn Pro Gln
                 5                  10                  15
Phe Leu Gln Gly Asn Val Ser Thr Ser Phe Val Gln Glu Met Asn Lys
                20                  25                  30

```
Pro  Leu  Asp  Phe  Asn  Glu  Ile  Arg  Gln  Leu  Leu  Thr  Thr  Ile  Ala  Gln
          35                       40                      45

Thr  Asp  Ile  Ala  Glu  Val  Thr  Leu  Lys  Ser  Asp  Asp  Phe  Glu  Leu  Thr
     50                       55                      60

Val  Arg  Lys  Ala  Val  Gly  Val  Asn  Asn  Ser  Val  Val  Pro  Val  Val  Thr
65                       50                            75                      80

Ala  Pro  Leu  Ser  Gly  Val  Val  Gly  Ser  Gly  Leu  Pro  Ser  Ala  Ile  Pro
               85                       90                            95

Ile  Val  Ala  His  Ala  Ala  Pro  Ser  Pro  Ser  Pro  Glu  Pro  Gly  Thr  Ser
               100                      105                     110

Arg  Ala  Ala  Asp  His  Ala  Val  Thr  Ser  Ser  Gly  Ser  Gln  Pro  Gly  Ala
          115                      120                     125

Lys  Ile  Ile  Asp  Gln  Lys  Leu  Ala  Glu  Val  Ala  Ser  Pro  Met  Val  Gly
          130                      135                     140

Thr  Phe  Tyr  Arg  Ala  Pro  Ala  Pro  Gly  Glu
145                      150
```

( 2 ) INFORMATION FOR SEQ ID NO:62:

( i ) SEQUENCE CHARACTERISTICS:
        ( A ) LENGTH: 24 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:62:

```
Ala  Val  Phe  Val  Glu  Val  Gly  Asp  Arg  Ile  Arg  Gln  Gly  Gln  Thr  Val
                    5                        10                      15

Cys  Ile  Ile  Glu  Ala  Met  Lys  Met
               20
```

( 2 ) INFORMATION FOR SEQ ID NO:63:

( i ) SEQUENCE CHARACTERISTICS:
        ( A ) LENGTH: 36 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:63:

```
Met  Leu  Asp  Lys  Ile  Val  Ile  Ala  Asn  Arg  Gly  Glu  Ile  Ala  Leu  Arg
               5                        10                      15

Ile  Leu  Arg  Ala  Cys  Lys  Glu  Leu  Gly  Ile  Lys  Thr  Val  Ala  Val  His
          20                       25                      30

Ser  Ser  Ala  Asp
          35
```

( 2 ) INFORMATION FOR SEQ ID NO:64:

( i ) SEQUENCE CHARACTERISTICS:
        ( A ) LENGTH: 21 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:64:

```
Arg  Asp  Leu  Lys  His  Val  Leu  Leu  Ala  Asp  Glu  Thr  Val  Cys  Ile  Gly
               5                        10                      15
```

Pro Ala Pro Ser Val
            20

( 2 ) INFORMATION FOR SEQ ID NO:65:

( i ) SEQUENCE CHARACTERISTICS:
        ( A ) LENGTH: 38 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:65:

Lys Ser Tyr Leu Asn Ile Pro Ala Ile Ile Ser Ala Ala Glu Ile Thr
                 5                  10                     15

Gly Ala Val Ala Ile His Pro Gly Tyr Gly Phe Leu Ser Glu Asn Ala
            20                  25                  30

Asn Phe Ala Glu Gln Val
            35

( 2 ) INFORMATION FOR SEQ ID NO:66:

( i ) SEQUENCE CHARACTERISTICS:
        ( A ) LENGTH: 43 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:66:

Glu Arg Ser Gly Phe Ile Phe Ile Gly Pro Lys Ala Glu Thr Ile Arg
                 5                  10                     15

Leu Met Gly Asp Lys Val Ser Ala Ile Ala Ala Met Lys Lys Ala Gly
            20                  25                  30

Val Pro Cys Val Pro Gly Ser Asp Gly Pro Leu
            35                  40

( 2 ) INFORMATION FOR SEQ ID NO:67:

( i ) SEQUENCE CHARACTERISTICS:
        ( A ) LENGTH: 141 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:67:

Gly Asp Asp Met Asp Lys Asn Arg Ala Ile Ala Lys Arg Ile Gly Tyr
                 5                  10                     15

Pro Val Ile Ile Lys Ala Ser Gly Gly Gly Gly Gly Arg Gly Met Arg
            20                  25                  30

Val Val Arg Gly Asp Ala Glu Leu Ala Gln Ser Ile Ser Met Thr Arg
            35                  40                  45

Ala Glu Ala Lys Ala Ala Phe Ser Asn Asp Met Val Tyr Met Glu Lys
            50                  55                  60

Tyr Leu Glu Asn Pro Arg His Val Glu Ile Gln Val Leu Ala Asp Gly
65                  70                  75                  80

Gln Gly Asn Ala Ile Tyr Leu Ala Glu Arg Asp Cys Ser Met Gln Arg
                85                  90                  95

Arg His Gln Lys Val Val Glu Glu Ala Pro Ala Pro Gly Ile Thr Pro
                100                 105                 110

```
Glu Leu Arg Arg Tyr Ile Gly Glu Arg Cys Ala Lys Ala Cys Val Asp
        115                 120                 125

Ile Gly Tyr Arg Gly Ala Gly Thr Phe Glu Phe Leu Phe
        130                 135             140
```

(2) INFORMATION FOR SEQ ID NO:68:

(i) SEQUENCE CHARACTERISTICS:
        (A) LENGTH: 50 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:68:

```
Glu Asn Gly Glu Phe Tyr Phe Ile Glu Met Asn Thr Arg Ile Gln Val
                5                   10                  15

Glu His Pro Val Thr Glu Met Ile Thr Gly Val Asp Leu Ile Lys Glu
        20                  25                  30

Gln Met Arg Ile Ala Ala Gly Gln Pro Leu Ser Ile Lys Gln Glu Glu
        35                  40                  45

Val His
 50
```

(2) INFORMATION FOR SEQ ID NO:69:

(i) SEQUENCE CHARACTERISTICS:
        (A) LENGTH: 25 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:69:

```
Val Arg Gly His Ala Val Glu Cys Arg Ile Asn Ala Glu Asp Pro Asn
                5                   10                  15

Leu Pro Ser Pro Gly Lys Ile Thr Arg
        20                  25
```

(2) INFORMATION FOR SEQ ID NO:70:

(i) SEQUENCE CHARACTERISTICS:
        (A) LENGTH: 6 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:70:

```
Phe His Ala Pro Gly Gly
                5
```

(2) INFORMATION FOR SEQ ID NO:71:

(i) SEQUENCE CHARACTERISTICS:
        (A) LENGTH: 7 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:71:

```
Phe Gly Val Arg Trp Glu Ser
                5
```

(2) INFORMATION FOR SEQ ID NO:72:

(i) SEQUENCE CHARACTERISTICS:
        (A) LENGTH: 44 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:72:

His Ile Tyr Ala Gly Tyr Thr Val Pro Pro Tyr Tyr Asp Ser Met Ile
            5                        10                    15

Gly Lys Leu Ile Cys Tyr Gly Glu Asn Arg Asp Val Ala Ile Ala Arg
         20                    25                    30

Met Lys Asn Ala Leu Gln Glu Leu Ile Ile Asp Gly
       35                 40

INFORMATION FOR SEQ ID NO:73:

(i) SEQUENCE CHARACTERISTICS:
        (A) LENGTH: 135 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:73:

Ile Lys Thr Asn Val Asp Leu Gln Ile Arg Ile Met Asn Asp Glu Asn
            5                        10                    15

Phe Gln His Gly Gly Thr Asn Ile His Tyr Leu Glu Lys Lys Leu Gly
         20                    25                    30

Leu Gln Glu Lys Met Asp Ile Arg Lys Ile Lys Lys Leu Ile Glu Leu
       35                 40                    45

Val Glu Glu Ser Gly Ile Ser Glu Leu Glu Ile Ser Glu Gly Glu Glu
    50                    55                    60

Ser Val Arg Ile Ser Arg Ala Ala Pro Ala Ala Ser Phe Pro Val Met
65                    70                    75                    80

Gln Gln Ala Tyr Ala Ala Pro Met Met Gln Gln Pro Ala Gln Ser Asn
             85                    90                    95

Ala Ala Ala Pro Ala Thr Val Pro Ser Met Glu Ala Pro Ala Ala Ala
         100                   105                 110

Glu Ile Ser Gly His Ile Val Arg Ser Pro Met Val Gly Thr Phe Tyr
       115                 120                 125

Arg Thr Pro Ser Pro Asp Ala
    130               135

(2) INFORMATION FOR SEQ ID NO:74:

(i) SEQUENCE CHARACTERISTICS:
        (A) LENGTH: 57 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:74:

Lys Ala Phe Ile Glu Val Gly Gln Lys Val Asn Val Gly Asp Thr Leu
            5                        10                    15

Cys Ile Val Glu Ala Met Lys Met Met Asn Gln Ile Glu Ala Asp Lys
         20                    25                    30

Ser Gly Thr Val Lys Ala Ile Leu Val Glu Ser Gly Gln Pro Val Glu
            35                  40                  45

Phe Asp Glu Pro Leu Val Val Ile Glu
        50                  55

( 2 ) INFORMATION FOR SEQ ID NO:75:

( i ) SEQUENCE CHARACTERISTICS:
            ( A ) LENGTH: 72 amino acids
            ( B ) TYPE: Amino acid
            ( C ) STRANDEDNESS: Single
            ( D ) TOPOLOGY: Linear ( i i ) MOLECULE TYPE: Peptide ( x i ) SEQUENCE DESCRIPTION: SEQ ID NO:75:

Met Leu Ser Ala Ala Leu Arg Thr Leu Lys His Val Leu Tyr Tyr Ser
                5                   10                  15

Arg Gln Cys Leu Met Val Ser Arg Asn Leu Gly Ser Val Gly Tyr Asp
            20                  25                  30

Pro Asn Glu Lys Thr Phe Asp Lys Ile Leu Val Ala Asn Arg Gly Glu
        35                  40                  45

Ile Ala Cys Arg Val Ile Arg Thr Cys Lys Lys Met Gly Ile Lys Thr
    50                  55                  60

Val Ala Ile His Ser Asp Val Asp
65                  70

( 2 ) INFORMATION FOR SEQ ID NO:76:

( i ) SEQUENCE CHARACTERISTICS:
            ( A ) LENGTH: 21 amino acids
            ( B ) TYPE: Amino acid
            ( C ) STRANDEDNESS: Single
            ( D ) TOPOLOGY: Linear ( i i ) MOLECULE TYPE: Peptide ( x i ) SEQUENCE DESCRIPTION: SEQ ID NO:76:

Ala Ser Ser Val His Val Lys Met Ala Asp Glu Ala Val Cys Val Gly
                5                   10                  15

Pro Ala Pro Thr Ser
            20

( 2 ) INFORMATION FOR SEQ ID NO:77:

( i ) SEQUENCE CHARACTERISTICS:
            ( A ) LENGTH: 38 amino acids
            ( B ) TYPE: Amino acid
            ( C ) STRANDEDNESS: Single
            ( D ) TOPOLOGY: Linear ( i i ) MOLECULE TYPE: Peptide ( x i ) SEQUENCE DESCRIPTION: SEQ ID NO:77:

Lys Ser Tyr Leu Asn Met Asp Ala Ile Met Glu Ala Ile Lys Lys Thr
                5                   10                  15

Arg Ala Gln Ala Val His Pro Gly Tyr Gly Phe Leu Ser Glu Asn Lys
            20                  25                  30

Glu Phe Ala Arg Cys Leu
        35

( 2 ) INFORMATION FOR SEQ ID NO:78:

( i ) SEQUENCE CHARACTERISTICS:
            ( A ) LENGTH: 41 amino acids
            ( B ) TYPE: Amino acid
            ( C ) STRANDEDNESS: Single ( D ) TOPOLOGY: Linear ( i i ) MOLECULE TYPE: Peptide ( x i ) SEQUENCE DESCRIPTION: SEQ ID NO:78:

| Ala | Ala | Glu | Asp | Val | Val | Phe | Ile | Gly | Pro | Asp | Thr | His | Ala | Ile | Gln |
|---|---|---|---|---|---|---|---|---|---|---|---|---|---|---|---|
| | | | | 5 | | | | | 10 | | | | | 15 | |
| Ala | Met | Gly | Asp | Lys | Ile | Glu | Ser | Lys | Leu | Leu | Ala | Lys | Lys | Ala | Glu |
| | | | 20 | | | | | 25 | | | | | 30 | | |
| Val | Asn | Thr | Ile | Pro | Gly | Phe | Asp | Gly | | | | | | | |
| | | 35 | | | | | 40 | | | | | | | | |

( 2 ) INFORMATION FOR SEQ ID NO:79:

( i ) SEQUENCE CHARACTERISTICS:
    ( A ) LENGTH: 144 amino acids
    ( B ) TYPE: Amino acid
    ( C ) STRANDEDNESS: Single
    ( D ) TOPOLOGY: Linear ( i i ) MOLECULE TYPE: Peptide ( x i ) SEQUENCE DESCRIPTION: SEQ ID NO:79:

| Val | Lys | Asp | Ala | Glu | Glu | Ala | Val | Arg | Ile | Ala | Arg | Glu | Ile | Gly | Tyr |
|---|---|---|---|---|---|---|---|---|---|---|---|---|---|---|---|
| | | | | 5 | | | | | 10 | | | | | 15 | |
| Pro | Val | Met | Ile | Lys | Ala | Ser | Ala | Gly | Gly | Gly | Lys | Gly | Met | Arg | |
| | | | 20 | | | | | 25 | | | | | 30 | | |
| Ile | Ala | Trp | Asp | Asp | Glu | Glu | Thr | Arg | Asp | Gly | Phe | Arg | Leu | Ser | Ser |
| | | | 35 | | | | | 40 | | | | | 45 | | |
| Gln | Glu | Ala | Ala | Ser | Ser | Phe | Gly | Asp | Asp | Arg | Leu | Leu | Ile | Glu | Lys |
| | | 50 | | | | | 55 | | | | | 60 | | | |
| Phe | Ile | Asp | Asn | Pro | Arg | His | Ile | Glu | Ile | Gln | Val | Leu | Gly | Asp | Lys |
| 65 | | | | | 70 | | | | | 75 | | | | | 80 |
| His | Gly | Asn | Ala | Leu | Trp | Leu | Asn | Glu | Arg | Glu | Cys | Ser | Ile | Gln | Arg |
| | | | | 85 | | | | | 90 | | | | | 95 | |
| Arg | Asn | Gln | Lys | Val | Val | Glu | Glu | Ala | Pro | Ser | Ile | Phe | Leu | Asp | Ala |
| | | | 100 | | | | | 105 | | | | | 110 | | |
| Glu | Thr | Arg | Arg | Ala | Met | Gly | Glu | Gln | Ala | Val | Ala | Leu | Ala | Arg | Ala |
| | | 115 | | | | | 120 | | | | | 125 | | | |
| Val | Lys | Tyr | Ser | Ser | Ala | Gly | Thr | Val | Glu | Phe | Leu | Val | Asp | Ser | Lys |
| | 130 | | | | | 135 | | | | | 140 | | | | |

INFORMATION FOR SEQ ID NO:80:

( i ) SEQUENCE CHARACTERISTICS:
    ( A ) LENGTH: 47 amino acids
    ( B ) TYPE: Amino acid
    ( C ) STRANDEDNESS: Single
    ( D ) TOPOLOGY: Linear ( i i ) MOLECULE TYPE: Peptide ( x i ) SEQUENCE DESCRIPTION: SEQ ID NO:80:

| Lys | Asn | Phe | Tyr | Phe | Leu | Glu | Met | Asn | Thr | Arg | Leu | Gln | Val | Glu | His |
|---|---|---|---|---|---|---|---|---|---|---|---|---|---|---|---|
| | | | | 5 | | | | | 10 | | | | | 15 | |
| Pro | Val | Thr | Glu | Cys | Ile | His | Trp | Pro | Gly | Pro | Ser | Pro | Gly | Lys | Thr |
| | | | 20 | | | | | 25 | | | | | 30 | | |
| Val | Leu | Gln | Glu | His | Leu | Ser | Gly | Thr | Asn | Lys | Leu | Ile | Phe | Ala | |
| | | | 35 | | | | | 40 | | | | | 45 | | |

( 2 ) INFORMATION FOR SEQ ID NO:81:

( i ) SEQUENCE CHARACTERISTICS:
    ( A ) LENGTH: 29 amino acids (B) TYPE: Amino acid
(C) STRANDEDNESS: Single
(D) TOPOLOGY: Linear (ii) MOLECULE TYPE: Peptide (xi) SEQUENCE DESCRIPTION: SEQ ID NO:81:

Phe Asn Gly Trp Ala Val Glu Cys Arg Val Tyr Ala Glu Asp Pro Tyr
                5                   10                  15
Lys Ser Phe Gly Leu Pro Ser Ile Gly Arg Leu Ser Gln
            20                  25

(2) INFORMATION FOR SEQ ID NO:82:

(i) SEQUENCE CHARACTERISTICS:
    (A) LENGTH: 14 amino acids
    (B) TYPE: Amino acid
    (C) STRANDEDNESS: Single
    (D) TOPOLOGY: Linear (ii) MOLECULE TYPE: Peptide (xi) SEQUENCE DESCRIPTION: SEQ ID NO:82:

Tyr Gln Glu Pro Leu His Leu Pro Gly Val Arg Val Asp Ser
                5                   10

(2) INFORMATION FOR SEQ ID NO:83:

(i) SEQUENCE CHARACTERISTICS:
    (A) LENGTH: 44 amino acids
    (B) TYPE: Amino acid
    (C) STRANDEDNESS: Single
    (D) TOPOLOGY: Linear (ii) MOLECULE TYPE: Peptide (xi) SEQUENCE DESCRIPTION: SEQ ID NO:83:

Gly Ile Gln Pro Gly Ser Asp Ile Ser Ile Tyr Tyr Asp Pro Met Ile
                5                   10                  15
Ser Lys Leu Ile Thr Tyr Gly Ser Asp Arg Thr Glu Ala Leu Lys Arg
            20                  25                  30
Met Ala Asp Ala Leu Asp Asn Tyr Val Ile Arg Gly
            35                  40

(2) INFORMATION FOR SEQ ID NO:84:

(i) SEQUENCE CHARACTERISTICS:
    (A) LENGTH: 251 amino acids
    (B) TYPE: Amino acid
    (C) STRANDEDNESS: Single
    (D) TOPOLOGY: Linear (ii) MOLECULE TYPE: Peptide (xi) SEQUENCE DESCRIPTION: SEQ ID NO:84:

Val Thr His Asn Ile Ala Leu Leu Arg Glu Val Ile Ile Asn Ser Arg
                5                   10                  15
Phe Val Lys Gly Asp Ile Ser Thr Lys Phe Leu Ser Asp Val Tyr Pro
            20                  25                  30
Asp Gly Phe Lys Gly His Met Leu Thr Lys Ser Glu Lys Asn Gln Leu
            35                  40                  45
Leu Ala Ile Ala Ser Ser Leu Phe Val Ala Phe Gln Leu Arg Ala Gln
        50              55                  60
His Phe Gln Glu Asn Ser Arg Met Pro Val Ile Lys Pro Asp Ile Ala
65                  70                  75                  80
Asn Trp Glu Leu Ser Val Lys Leu His Asp Lys Val His Thr Val Val
                85                  90                  95

Ala Ser Asn Asn Gly Ser Val Phe Ser Val Glu Val Asp Gly Ser Lys
                100                 105                 110

Leu Asn Val Thr Ser Thr Trp Asn Leu Ala Ser Pro Leu Leu Ser Val
        115                 120                 125

Ser Val Asp Gly Thr Gln Arg Thr Val Gln Cys Leu Ser Arg Glu Ala
    130                 135                 140

Gly Gly Asn Met Ser Ile Gln Phe Leu Gly Thr Val Tyr Lys Val Asn
145                 150                 155                 160

Ile Leu Thr Arg Leu Ala Ala Glu Leu Asn Lys Phe Met Leu Glu Lys
            165                 170                 175

Val Thr Glu Asp Thr Ser Ser Val Leu Arg Ser Pro Met Pro Gly Val
            180                 185                 190

Val Val Ala Val Ser Val Lys Pro Gly Asp Ala Val Ala Glu Gly Gln
        195                 200                 205

Glu Ile Cys Val Ile Glu Ala Met Lys Met Gln Asn Ser Met Thr Ala
    210                 215                 220

Gly Lys Thr Gly Thr Val Lys Ser Val His Cys Gln Ala Gly Asp Thr
225                 230                 235                 240

Val Gly Glu Gly Asp Leu Leu Val Glu Leu Glu
            245                 250

( 2 ) INFORMATION FOR SEQ ID NO:85:

( i ) SEQUENCE CHARACTERISTICS:
            ( A ) LENGTH: 90 amino acids
            ( B ) TYPE: Amino acid
            ( C ) STRANDEDNESS: Single
            ( D ) TOPOLOGY: Linear ( i i ) MOLECULE TYPE: Peptide ( x i ) SEQUENCE DESCRIPTION: SEQ ID NO:85:

Met Pro Tyr Arg Glu Arg Phe Cys Ala Ile Arg Trp Cys Arg Asn Ser
                5                   10                  15

Gly Arg Ser Ser Gln Gln Leu Leu Trp Thr Leu Lys Arg Ala Pro Val
            20                  25                  30

Tyr Ser Gln Gln Cys Leu Val Val Ser Arg Ser Leu Ser Ser Val Glu
        35                  40                  45

Tyr Glu Pro Lys Glu Lys Thr Phe Asp Lys Ile Leu Ile Ala Asn Arg
    50                  55                  60

Gly Glu Ile Ala Cys Arg Val Ile Lys Thr Cys Arg Lys Met Gly Ile
65                  70                  75                  80

Arg Thr Val Ala Ile His Ser Asp Val Asp
            85                  90

( 2 ) INFORMATION FOR SEQ ID NO:86:

( i ) SEQUENCE CHARACTERISTICS:
            ( A ) LENGTH: 21 amino acids
            ( B ) TYPE: Amino acid
            ( C ) STRANDEDNESS: Single
            ( D ) TOPOLOGY: Linear ( i i ) MOLECULE TYPE: Peptide ( x i ) SEQUENCE DESCRIPTION: SEQ ID NO:86:

Ala Ser Ser Val His Val Lys Met Ala Asp Glu Ala Val Cys Val Gly
                5                   10                  15
Pro Ala Pro Thr Ser
            20

( 2 ) INFORMATION FOR SEQ ID NO:87:

( i ) SEQUENCE CHARACTERISTICS:
        ( A ) LENGTH: 38 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:87:

```
Lys  Ser  Tyr  Leu  Asn  Met  Asp  Ala  Ile  Met  Glu  Ala  Ile  Lys  Lys  Thr
                    5                        10                      15
Gly  Ala  Gln  Ala  Val  His  Pro  Gly  Tyr  Gly  Phe  Leu  Ser  Glu  Asn  Lys
               20                       25                      30
Glu  Phe  Ala  Lys  Cys  Leu
               35
```

( 2 ) INFORMATION FOR SEQ ID NO:88:

( i ) SEQUENCE CHARACTERISTICS:
        ( A ) LENGTH: 41 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:88:

```
Ala  Ala  Glu  Asp  Val  Thr  Phe  Ile  Gly  Pro  Asp  Thr  His  Ala  Ile  Gln
                    5                        10                      15
Ala  Met  Gly  Asp  Lys  Ile  Glu  Ser  Lys  Leu  Leu  Ala  Lys  Arg  Ala  Lys
               20                       25                      30
Val  Asn  Thr  Ile  Pro  Gly  Phe  Asp  Gly
               35                  40
```

( 2 ) INFORMATION FOR SEQ ID NO:89:

( i ) SEQUENCE CHARACTERISTICS:
        ( A ) LENGTH: 144 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:89:

```
Leu  Lys  Asp  Ala  Asp  Glu  Ala  Val  Arg  Ile  Ala  Arg  Glu  Ile  Gly  Tyr
                    5                        10                      15
Pro  Val  Met  Ile  Lys  Ala  Ser  Ala  Gly  Gly  Gly  Gly  Lys  Gly  Met  Arg
               20                       25                      30
Ile  Pro  Trp  Asp  Asp  Glu  Glu  Thr  Arg  Asp  Gly  Phe  Arg  Phe  Ser  Ser
               35                       40                      45
Gln  Glu  Ala  Ala  Ser  Ser  Phe  Gly  Asp  Asp  Arg  Leu  Leu  Ile  Glu  Lys
50                            55                       60
Phe  Ile  Asp  Asn  Pro  Arg  His  Ile  Glu  Ile  Gln  Val  Leu  Gly  Asp  Lys
65                       70                       75                      80
His  Gly  Asn  Ala  Leu  Trp  Leu  Asn  Glu  Arg  Glu  Cys  Ser  Ile  Gln  Arg
                    85                       90                      95
Arg  Asn  Gln  Lys  Val  Val  Glu  Glu  Ala  Pro  Ser  Ile  Phe  Leu  Asp  Pro
               100                           105                    110
Glu  Thr  Arg  Arg  Ala  Met  Gly  Glu  Gln  Ala  Val  Ala  Trp  Pro  Lys  Ala
               115                      120                     125
Val  Lys  Tyr  Ser  Ser  Ala  Gly  Thr  Val  Glu  Phe  Leu  Val  Asp  Ser  Gln
               130                      135                     140
```

INFORMATION FOR SEQ ID NO:90:

( i ) SEQUENCE CHARACTERISTICS:
       ( A ) LENGTH: 48 amino acids
       ( B ) TYPE: Amino acid
       ( C ) STRANDEDNESS: Single
       ( D ) TOPOLOGY: Linear ( i i ) MOLECULE TYPE: Peptide ( x i ) SEQUENCE DESCRIPTION: SEQ ID NO:90:

Lys Asn Phe Tyr Phe Leu Glu Met Asn Thr Arg Leu Gln Val Glu His
                  5                  10                 15

Pro Val Thr Glu Cys Ile Thr Gly Leu Asp Leu Val Gln Glu Met Ile
            20                  25                 30

Leu Val Ala Lys Gly Tyr Pro Leu Arg His Lys Gln Glu Asp Ile Pro
        35                  40                 45

INFORMATION FOR SEQ ID NO:91:

( i ) SEQUENCE CHARACTERISTICS:
       ( A ) LENGTH: 29 amino acids
       ( B ) TYPE: Amino acid
       ( C ) STRANDEDNESS: Single
       ( D ) TOPOLOGY: Linear ( i i ) MOLECULE TYPE: Peptide ( x i ) SEQUENCE DESCRIPTION: SEQ ID NO:91:

Ile Ser Gly Trp Ala Val Glu Cys Arg Val Tyr Ala Glu Asp Pro Tyr
                  5                  10                 15

Lys Ser Phe Gly Leu Pro Ser Ile Gly Arg Leu Ser Gln
            20                  25

( 2 ) INFORMATION FOR SEQ ID NO:92:

( i ) SEQUENCE CHARACTERISTICS:
       ( A ) LENGTH: 14 amino acids
       ( B ) TYPE: Amino acid
       ( C ) STRANDEDNESS: Single
       ( D ) TOPOLOGY: Linear ( i i ) MOLECULE TYPE: Peptide ( x i ) SEQUENCE DESCRIPTION: SEQ ID NO:92:

Tyr Gln Glu Pro Ile His Leu Pro Gly Val Arg Val Asp Ser
                  5                  10

INFORMATION FOR SEQ ID NO:93:

( i ) SEQUENCE CHARACTERISTICS:
       ( A ) LENGTH: 44 amino acids
       ( B ) TYPE: Amino acid
       ( C ) STRANDEDNESS: Single
       ( D ) TOPOLOGY: Linear ( i i ) MOLECULE TYPE: Peptide ( x i ) SEQUENCE DESCRIPTION: SEQ ID NO:93:

Gly Ile Gln Pro Gly Ser Asp Ile Ser Ile Tyr His Asp Pro Met Ile
                  5                  10                 15

Ser Lys Leu Val Thr Tyr Gly Ser Asp Arg Ala Glu Ala Leu Lys Arg
            20                  25                 30

Met Glu Asp Ala Leu Asp Ser Tyr Val Ile Arg Gly
        35                  40

95

-continued

INFORMATION FOR SEQ ID NO:94:

( i ) SEQUENCE CHARACTERISTICS:
        ( A ) LENGTH: 251 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:94:

```
Val Thr His Asn Ile Pro Leu Leu Arg Glu Val Ile Ile Asn Thr Arg
                  5                  10                 15
Phe Val Lys Gly Asp Ile Ser Thr Lys Phe Leu Ser Asp Val Tyr Pro
            20                  25              30
Asp Gly Phe Lys Gly His Met Leu Thr Pro Ser Glu Arg Asp Gln Leu
        35                  40                  45
Leu Ala Ile Ala Ser Ser Leu Phe Val Ala Ser Gln Leu Arg Ala Gln
    50                  55                  60
Arg Phe Gln Glu His Ser Arg Val Pro Val Ile Arg Pro Asp Val Ala
65                  70                  75                  80
Lys Trp Glu Leu Ser Val Lys Leu His Asp Glu Asp His Thr Val Val
                85                  90                  95
Ala Ser Asn Asn Gly Pro Thr Phe Asn Val Glu Val Asp Gly Ser Lys
            100                 105                 110
Leu Asn Val Thr Ser Thr Trp Asn Leu Ala Ser Pro Leu Leu Ser Val
        115                 120                 125
Asn Val Asp Gly Thr Gln Arg Thr Val Gln Cys Leu Ser Pro Asp Ala
    130                 135                 140
Gly Gly Asn Met Ser Ile Gln Phe Leu Gly Thr Val Tyr Lys Val His
145                 150                 155                 160
Ile Leu Thr Lys Leu Ala Ala Glu Leu Asn Lys Phe Met Leu Glu Lys
                165                 170                 175
Val Pro Lys Asp Thr Ser Ser Val Leu Arg Ser Pro Lys Pro Gly Val
            180                 185                 190
Val Val Ala Val Ser Val Lys Pro Gly Asp Met Val Ala Glu Gly Gln
        195                 200                 205
Glu Ile Cys Val Ile Glu Ala Met Lys Met Gln Asn Ser Met Thr Ala
    210                 215                 220
Gly Lys Met Gly Lys Val Lys Leu Val His Cys Lys Ala Gly Asp Thr
225                 230                 235                 240
Val Gly Glu Gly Asp Leu Leu Val Glu Leu Glu
                245                 250
```

( 2 ) INFORMATION FOR SEQ ID NO:95:

( i ) SEQUENCE CHARACTERISTICS:
        ( A ) LENGTH: 17 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:95:

```
Gln Arg Lys Phe Ala Gly Leu Arg Asp Asn Phe Asn Leu Leu Gly Glu
                  5                  10                  15
Lys
```

( 2 ) INFORMATION FOR SEQ ID NO:96:

( i ) SEQUENCE CHARACTERISTICS:
        ( A ) LENGTH: 34 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:96:

```
Asn  Lys  Ile  Leu  Val  Ala  Asn  Arg  Gly  Glu  Ile  Pro  Ile  Arg  Ile  Phe
                    5                        10                       15
Arg  Thr  Ala  His  Glu  Leu  Ser  Met  Gln  Thr  Val  Ala  Ile  Tyr  Ser  His
               20                        25                       30
Glu  Asp
```

( 2 ) INFORMATION FOR SEQ ID NO:97:

( i ) SEQUENCE CHARACTERISTICS:
        ( A ) LENGTH: 24 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:97:

```
Arg  Leu  Ser  Thr  His  Lys  Gln  Lys  Ala  Asp  Glu  Ala  Tyr  Val  Ile  Gly
                    5                        10                       15
Glu  Val  Gly  Gln  Tyr  Thr  Pro  Val
               20
```

( 2 ) INFORMATION FOR SEQ ID NO:98:

( i ) SEQUENCE CHARACTERISTICS:
        ( A ) LENGTH: 38 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:98:

```
Gly  Ala  Tyr  Leu  Ala  Ile  Asp  Glu  Ile  Ser  Ile  Ala  Gln  Lys  His
                    5                        10                       15
Gln  Val  Asp  Phe  Ile  His  Pro  Gly  Tyr  Gly  Phe  Leu  Ser  Glu  Asn  Ser
               20                        25                       30
Glu  Phe  Ala  Asp  Lys  Val
               35
```

( 2 ) INFORMATION FOR SEQ ID NO:99:

( i ) SEQUENCE CHARACTERISTICS:
        ( A ) LENGTH: 41 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:99:

```
Val  Lys  Ala  Gly  Ile  Thr  Trp  Ile  Gly  Pro  Pro  Ala  Glu  Val  Ile  Asp
                    5                        10                       15
Ser  Val  Gly  Asp  Lys  Val  Ser  Ala  Arg  Asn  Leu  Ala  Ala  Lys  Ala  Asn
               20                        25                       30
Val  Pro  Thr  Val  Pro  Gly  Thr  Pro  Gly
```

(2) INFORMATION FOR SEQ ID NO:100:

(i) SEQUENCE CHARACTERISTICS:
        (A) LENGTH: 144 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:100:

```
Ile Glu Thr Val Glu Glu Ala Leu Asp Phe Val Asn Glu Tyr Gly Tyr
              5                  10                 15
Pro Val Ile Ile Lys Ala Ala Phe Gly Gly Gly Arg Gly Met Arg
             20                  25                 30
Val Val Arg Glu Gly Asp Asp Val Ala Asp Ala Phe Gln Arg Ala Thr
            35                  40                 45
Ser Glu Ala Arg Thr Ala Phe Gly Asn Gly Thr Cys Phe Val Glu Arg
     50                 55                 60
Phe Leu Asp Lys Pro Lys His Ile Glu Val Gln Leu Leu Ala Asp Asn
 65                70                 75                 80
His Gly Asn Val Val His Leu Phe Glu Arg Asp Cys Ser Val Gln Arg
                85                  90                 95
Arg His Gln Lys Val Val Glu Val Ala Pro Ala Lys Thr Leu Pro Arg
            100                 105                110
Glu Val Arg Asp Ala Ile Leu Thr Asp Ala Val Lys Leu Ala Lys Glu
            115                 120                125
Cys Gly Tyr Arg Asn Ala Gly Thr Ala Glu Phe Leu Val Asp Asn Gln
     130                135                 140
```

INFORMATION FOR SEQ ID NO:101:

(i) SEQUENCE CHARACTERISTICS:
        (A) LENGTH: 51 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:101:

```
Asn Arg His Tyr Phe Ile Glu Ile Asn Pro Arg Ile Gln Val Glu His
               5                  10                 15
Thr Ile Thr Glu Glu Ile Thr Gly Ile Asp Ile Val Ala Ala Gln Ile
            20                  25                 30
Gln Ile Ala Ala Gly Ala Ser Leu Pro Gln Leu Gly Leu Phe Gln Asp
          35                  40                 45
Lys Ile Thr
 50
```

(2) INFORMATION FOR SEQ ID NO:102:

(i) SEQUENCE CHARACTERISTICS:
        (A) LENGTH: 20 amino acids
        (B) TYPE: Amino acid
        (C) STRANDEDNESS: Single
        (D) TOPOLOGY: Linear (ii) MOLECULE TYPE: Peptide (xi) SEQUENCE DESCRIPTION: SEQ ID NO:102:

```
Thr Arg Gly Phe Ala Ile Gln Cys Arg Ile Thr Thr Glu Asp Pro Ala
              5                  10                 15
```

Lys Asn Phe Gln
            20

( 2 ) INFORMATION FOR SEQ ID NO:103:

( i ) SEQUENCE CHARACTERISTICS:
        ( A ) LENGTH: 14 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:103:

Pro Asp Thr Gly Arg Ile Glu Val Tyr Arg Ser Ala Gly Gly
                 5                   10

INFORMATION FOR SEQ ID NO:104:

( i ) SEQUENCE CHARACTERISTICS:
        ( A ) LENGTH: 52 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:104:

Asn Gly Val Arg Leu Asp Gly Gly Asn Ala Tyr Ala Gly Thr Ile Ile
                 5                   10                  15

Ser Pro His Tyr Asp Ser Met Leu Val Lys Cys Ser Cys Ser Gly Ser
             20                  25                  30

Thr Tyr Glu Ile Val Arg Arg Lys Met Ile Arg Ala Leu Ile Glu Phe
         35                  40                  45

Arg Ile Arg Gly
        50

( 2 ) INFORMATION FOR SEQ ID NO:105:

( i ) SEQUENCE CHARACTERISTICS:
        ( A ) LENGTH: 257 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:105:

Val Lys Thr Asn Ile Pro Phe Leu Leu Thr Leu Leu Thr Asn Pro Val
                 5                   10                  15

Phe Ile Glu Gly Thr Tyr Trp Gly Thr Phe Ile Asp Asp Thr Pro Gln
             20                  25                  30

Leu Phe Gln Met Val Ser Ser Gln Asn Arg Ala Gln Lys Leu Leu His
         35                  40                  45

Tyr Leu Ala Asp Val Ala Asp Asn Gly Ser Ser Ile Lys Gly Gln Ile
     50                  55                  60

Gly Leu Pro Lys Leu Lys Ser Asn Pro Ser Val Pro His Ser Tyr Asn
65                   70                  75                  80

Met Tyr Pro Arg Val Tyr Glu Asp Phe Gln Lys Met Arg Glu Thr Tyr
                 85                  90                  95

Gly Asp Leu Ser Val Leu Pro Thr Arg Ser Phe Leu Ser Pro Leu Glu
                100                 105                 110

Thr Asp Glu Glu Ile Glu Val Val Ile Glu Gln Gly Lys Thr Leu Ile

|  |  |  | 115 |  |  |  |  |  | 120 |  |  |  |  | 125 |  |  |
|---|---|---|---|---|---|---|---|---|---|---|---|---|---|---|---|---|
| Ile | Lys | Leu | Gln | Ala | Val | Gly | Asp | Leu | Asn | Lys | Lys | Thr | Gly | Glu | Arg |
|  | 130 |  |  |  | 135 |  |  |  |  | 140 |  |  |  |  |  |
| Glu | Val | Tyr | Phe | Asp | Leu | Asn | Gly | Glu | Met | Arg | Lys | Ile | Arg | Val | Ala |
| 145 |  |  |  |  | 150 |  |  |  |  | 155 |  |  |  |  | 160 |
| Asp | Arg | Ser | Gln | Lys | Val | Glu | Thr | Val | Thr | Lys | Ser | Lys | Ala | Asp | Met |
|  |  |  |  | 165 |  |  |  |  | 170 |  |  |  |  | 175 |  |
| His | Asp | Pro | Leu | His | Ile | Gly | Ala | Pro | Met | Ala | Gly | Val | Ile | Val | Glu |
|  |  |  | 180 |  |  |  |  | 185 |  |  |  |  | 190 |  |  |
| Val | Lys | Val | His | Lys | Gly | Ser | Leu | Ile | Lys | Lys | Gly | Gln | Pro | Val | Ala |
|  |  | 195 |  |  |  |  | 200 |  |  |  |  | 205 |  |  |  |
| Val | Leu | Ser | Ala | Met | Lys | Met | Glu | Met | Ile | Ile | Ser | Ser | Pro | Ser | Asp |
|  | 210 |  |  |  |  | 215 |  |  |  |  | 220 |  |  |  |  |
| Gly | Gln | Val | Lys | Glu | Val | Phe | Val | Ser | Asp | Gly | Glu | Asn | Val | Asp | Ser |
| 225 |  |  |  |  | 230 |  |  |  |  | 235 |  |  |  |  | 240 |
| Ser | Asp | Leu | Leu | Val | Leu | Leu | Glu | Asp | Gln | Val | Pro | Val | Glu | Thr | Lys |
|  |  |  |  | 245 |  |  |  |  | 250 |  |  |  |  | 255 |  |
| Ala |  |  |  |  |  |  |  |  |  |  |  |  |  |  |  |

( 2 ) INFORMATION FOR SEQ ID NO:106:

( i ) SEQUENCE CHARACTERISTICS:
        ( A ) LENGTH: 165 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:106:

| Val | Leu | Thr | Val | Ala | Leu | Phe | Pro | Gln | Pro | Gly | Leu | Lys | Phe | Leu | Glu |
|---|---|---|---|---|---|---|---|---|---|---|---|---|---|---|---|
|  |  |  |  | 5 |  |  |  |  | 10 |  |  |  |  | 15 |  |
| Asn | Arg | His | Asn | Pro | Ala | Ala | Phe | Glu | Pro | Val | Pro | Gln | Ala | Glu | Ala |
|  |  |  | 20 |  |  |  |  | 25 |  |  |  |  | 30 |  |  |
| Ala | Gln | Pro | Val | Ala | Lys | Ala | Glu | Lys | Pro | Ala | Ala | Ser | Gly | Val | Tyr |
|  |  | 35 |  |  |  |  | 40 |  |  |  |  | 45 |  |  |  |
| Thr | Val | Glu | Val | Glu | Gly | Lys | Ala | Phe | Val | Val | Lys | Val | Ser | Asp | Gly |
|  | 50 |  |  |  |  | 55 |  |  |  |  | 60 |  |  |  |  |
| Gly | Asp | Val | Ser | Gln | Leu | Thr | Ala | Ala | Ala | Pro | Ala | Pro | Ala | Pro | Ala |
| 65 |  |  |  |  | 70 |  |  |  |  | 75 |  |  |  |  | 80 |
| Pro | Ala | Pro | Ala | Ser | Ala | Pro | Ala | Ala | Ala | Ala | Pro | Ala | Gly | Ala | Gly |
|  |  |  |  | 85 |  |  |  |  | 90 |  |  |  |  | 95 |  |
| Thr | Pro | Val | Thr | Ala | Pro | Leu | Ala | Gly | Thr | Ile | Trp | Lys | Val | Leu | Ala |
|  |  |  | 100 |  |  |  |  | 105 |  |  |  |  | 110 |  |  |
| Ser | Glu | Gly | Gln | Thr | Val | Ala | Ala | Gly | Glu | Val | Leu | Leu | Ile | Leu | Glu |
|  |  | 115 |  |  |  |  | 120 |  |  |  |  | 125 |  |  |  |
| Ala | Met | Lys | Met | Glu | Thr | Glu | Ile | Arg | Ala | Ala | Gln | Ala | Gly | Thr | Val |
|  | 130 |  |  |  |  | 135 |  |  |  |  | 140 |  |  |  |  |
| Arg | Gly | Ile | Ala | Val | Lys | Ala | Gly | Asp | Ala | Val | Ala | Val | Gly | Asp | Thr |
| 145 |  |  |  |  | 150 |  |  |  |  | 155 |  |  |  |  | 160 |
| Leu | Met | Thr | Leu | Ala |  |  |  |  |  |  |  |  |  |  |  |
|  |  |  |  | 165 |  |  |  |  |  |  |  |  |  |  |  |

( 2 ) INFORMATION FOR SEQ ID NO:107:

( i ) SEQUENCE CHARACTERISTICS:
        ( A ) LENGTH: 123 amino acids
        ( B ) TYPE: Amino acid
        ( C ) STRANDEDNESS: Single
        ( D ) TOPOLOGY: Linear ( i i ) MOLECULE TYPE: Peptide ( x i ) SEQUENCE DESCRIPTION: SEQ ID NO:107:

| Met | Lys | Leu | Lys | Val | Thr | Val | Asn | Gly | Thr | Ala | Tyr | Asp | Val | Asp | Val |
|---|---|---|---|---|---|---|---|---|---|---|---|---|---|---|---|
|  |  |  |  | 5 |  |  |  |  | 10 |  |  |  |  |  | 15 |

| Asp | Val | Asp | Lys | Ser | His | Glu | Asn | Pro | Met | Gly | Thr | Ile | Leu | Phe | Gly |
|---|---|---|---|---|---|---|---|---|---|---|---|---|---|---|---|
|  |  |  | 20 |  |  |  |  | 25 |  |  |  |  | 30 |  |  |

| Gly | Gly | Thr | Gly | Gly | Ala | Pro | Ala | Pro | Arg | Ala | Ala | Gly | Gly | Ala | Gly |
|---|---|---|---|---|---|---|---|---|---|---|---|---|---|---|---|
|  |  | 35 |  |  |  |  | 40 |  |  |  |  | 45 |  |  |  |

| Ala | Gly | Lys | Ala | Gly | Glu | Gly | Glu | Ile | Pro | Ala | Pro | Leu | Ala | Gly | Thr |
|---|---|---|---|---|---|---|---|---|---|---|---|---|---|---|---|
|  | 50 |  |  |  |  | 55 |  |  |  |  | 60 |  |  |  |  |

| Val | Ser | Lys | Ile | Leu | Val | Lys | Glu | Gly | Asp | Thr | Val | Lys | Ala | Gly | Gln |
|---|---|---|---|---|---|---|---|---|---|---|---|---|---|---|---|
| 65 |  |  |  |  | 70 |  |  |  |  | 75 |  |  |  |  | 80 |

| Thr | Val | Leu | Val | Leu | Glu | Ala | Met | Lys | Met | Glu | Thr | Glu | Ile | Asn | Ala |
|---|---|---|---|---|---|---|---|---|---|---|---|---|---|---|---|
|  |  |  |  | 85 |  |  |  |  | 90 |  |  |  |  | 95 |  |

| Pro | Thr | Asp | Gly | Lys | Val | Glu | Lys | Val | Leu | Val | Lys | Glu | Arg | Asp | Ala |
|---|---|---|---|---|---|---|---|---|---|---|---|---|---|---|---|
|  |  |  |  | 100 |  |  |  |  | 105 |  |  |  |  | 110 |  |

| Val | Gln | Gly | Gly | Gln | Gly | Leu | Ile | Lys | Ile | Gly |
|---|---|---|---|---|---|---|---|---|---|---|
|  |  | 115 |  |  |  |  | 120 |  |  |  |

( 2 ) INFORMATION FOR SEQ ID NO:108:

( i ) SEQUENCE CHARACTERISTICS:
        ( A ) LENGTH: 1473 base pairs
        ( B ) TYPE: Nucleic acid
        ( C ) STRANDEDNESS: Single
        ( D ) TOPOLOGY: Linear ( i i ) MOLECULE TYPE: Oligonucleotide ( x i ) SEQUENCE DESCRIPTION: SEQ ID NO:108:

```
GTGATGATCA AGGCATCATG GGGTGGGGGT GGTAAAGGAA TAAGGAAGGT ACATAATGAT    60
GATGAGGTCA GAGCATTGTT TAAGCAAGTG CAAGGAGAAG TCCCCGGATC GCCTATATTT   120
ATTATGAAGG TGGCATCTCA GAGTCGACAT CTAGAGGTTC AATTGCTCTG TGACAAGCAT   180
GGCAACGTGG CAGCACTGCA CAGTCGAGAC TGTAGTGTTC AAAGAAGGCA TCAAAAGATC   240
ATTGAGGAGG GACCAATTAC AGTTGCTCCT CCAGAAACAA TTAAAGAGCT GAGCAGGCG    300
GCAAGGCGAC TAGCTAAATG TGTGCAATAT CAGGGTGCTG CTACAGTGGA ATATCTGTAC   360
AGCATGGAAA CAGGCGAATA CTATTTCCTG GAGCTTAATC CAAGGTTGCA GGTAGAACAC   420
CCTGTGACCG AATGGATTGC TGAAATAAAC TTACCYGCAT CTCAAGTTGT AGTAGGAATG   480
GGCATACCAC TCTACAACAT TCCAGAGATC AGACGCTTTT ATGGAATAGA ACATGGAGGT   540
GGCTATCAYG CTTGGAAGGA AATATCAGCT GTTGCAACTA AATTTGATYT GGACAAAGCA   600
CAGTCTGTAA AGCCAAARGG TCATTGTGTA GCAGTTAGAG TTACTAGCGA GGATCCAGAT   660
GATGGGTTTA AGCCTACMAG TGGAAGAGTR GAAGAGCTGA ACTTTAAAAG TAAACCCAAT   720
GTTTGGGCCT ATTTCTCYGT TARGTCCGGA GGTGCAATTC AYGAGTTCTC TGATTCCCAG   780
TTTGGTCATG TTTTTGCTTY TGGGGAATCT AGGTCWTTGG CAATAGCCAA TATGGTACTT   840
GGGTTAAAAG AGATCCAAAT TCGTGGAGAG ATACGCACTA ATGTTGACTA CACTGTGGAT   900
CTCTTGAATG CTGCAGAGTA CCGAGAAAAT AWGATTCACA CTGGTTGGCT AGACAGCAGA   960
ATAGCWATGC GYGTTAGAGC AGAGAGGCCC CCATGGTACC TTTCAGTTGT TGGTGGAGCT  1020
CTATATGAAG CATCAAGCAG GAGCTCGAGT GTTGTAACCG ATTATGTTGG TTATCTCAGT  1080
AAAGGTCAAA TACCACCAAA GCACATCTCT CTTGTCAAYT TGACTGTAAC ACTGAATATA  1140
```

5,539,092

107                                                                                                                     108

-continued

| GATGGGAGCA | AATATACGAT | TGAGACAGTA | CGAGGTGGAC | CCCGTAGCTA | CAAATTAAGA | 1200 |
| ATTAATGAAT | CAGAGGTTGA | RGCAGAGATA | CATTTCCTGC | GAGATGGCGG | ACYCTTAATG | 1260 |
| CAGTYGGATG | GAAACAGTCA | TGTAATTTAC | GCCGAGACAG | AAGCTKCTGG | CACGCGCCTT | 1320 |
| CTAATCAATG | GGAGAACATG | CTTATTACAG | AAAGAGCAYG | ATCCTTCCAG | GTTGTTGGCT | 1380 |
| GATACACCRT | GCAARCTTCT | TCGGTTTTTG | GTCGCGGATR | GTTCTCATGT | GGTTGCTGAT | 1440 |
| ACGCCATATG | CYGAGGTGGA | GGCCATGAAA | ATG |            |            | 1473 |

( 2 ) INFORMATION FOR SEQ ID NO:109:

( i ) SEQUENCE CHARACTERISTICS:
            ( A ) LENGTH: 491 amino acids
            ( B ) TYPE: Amino acid
            ( C ) STRANDEDNESS: Single
            ( D ) TOPOLOGY: Linear ( i i ) MOLECULE TYPE: Peptide ( i x ) FEATURE:
            ( A ) NAME/KEY: Xaa
            ( B ) LOCATION: 248, 267, 311, 412, 418, 422, 436, and 474
            ( C ) IDENTIFICATION METHOD: Xaa =any amino acid ( x i ) SEQUENCE DESCRIPTION: SEQ ID NO:109:

```
Val Met Ile Lys Ala Ser Trp Gly Gly Gly Gly Lys Gly Ile Arg Lys
              5                  10                  15
Val His Asn Asp Asp Glu Val Arg Ala Leu Phe Lys Gln Val Gln Gly
             20                  25                  30
Glu Val Pro Gly Ser Pro Ile Phe Ile Met Lys Val Ala Ser Gln Ser
             35                  40                  45
Arg His Leu Glu Val Gln Leu Leu Cys Asp Lys His Gly Asn Val Ala
             50                  55                  60
Ala Leu His Ser Arg Asp Cys Ser Val Gln Arg Arg His Gln Lys Ile
 65                  70                  75                  80
Ile Glu Glu Gly Pro Ile Thr Val Ala Pro Pro Glu Thr Ile Lys Glu
                 85                  90                  95
Leu Glu Gln Ala Ala Arg Arg Leu Ala Lys Cys Val Gln Tyr Gln Gly
            100                 105                 110
Ala Ala Thr Val Glu Tyr Leu Tyr Ser Met Glu Thr Gly Glu Tyr Tyr
            115                 120                 125
Phe Leu Glu Leu Asn Pro Arg Leu Gln Val Glu His Pro Val Thr Glu
            130                 135                 140
Trp Ile Ala Glu Ile Asn Leu Pro Ala Ser Gln Val Val Val Gly Met
145                 150                 155                 160
Gly Ile Pro Leu Tyr Asn Ile Pro Glu Ile Arg Arg Phe Tyr Gly Ile
                165                 170                 175
Glu His Gly Gly Gly Tyr His Ala Trp Lys Glu Ile Ser Ala Val Ala
            180                 185                 190
Thr Lys Phe Asp Leu Asp Lys Ala Gln Ser Val Lys Pro Lys Gly His
            195                 200                 205
Cys Val Ala Val Arg Val Thr Ser Glu Asp Pro Asp Asp Gly Phe Lys
            210                 215                 220
Pro Thr Ser Gly Arg Val Glu Glu Leu Asn Phe Lys Ser Lys Pro Asn
225                 230                 235                 240
Val Trp Ala Tyr Phe Ser Val Xaa Ser Gly Gly Ala Ile His Glu Phe
                245                 250                 255
Ser Asp Ser Gln Phe Gly His Val Phe Ala Xaa Gly Glu Ser Arg Ser
            260                 265                 270
```

| | | | | | | | | | | | | | | |
|---|---|---|---|---|---|---|---|---|---|---|---|---|---|---|
| Leu | Ala | Ile | Ala | Asn | Met | Val | Leu | Gly | Leu | Lys | Glu | Ile | Gln | Ile | Arg |
| | | 275 | | | | | 280 | | | | 285 | | | |
| Gly | Glu | Ile | Arg | Thr | Asn | Val | Asp | Tyr | Thr | Val | Asp | Leu | Leu | Asn | Ala |
| | 290 | | | | | 295 | | | | | 300 | | | | |
| Ala | Glu | Tyr | Arg | Glu | Asn | Xaa | Ile | His | Thr | Gly | Trp | Leu | Asp | Ser | Arg |
| 305 | | | | | 310 | | | | | 315 | | | | | 320 |
| Ile | Ala | Met | Arg | Val | Arg | Ala | Glu | Arg | Pro | Pro | Trp | Tyr | Leu | Ser | Val |
| | | | | 325 | | | | | 330 | | | | | 335 | |
| Val | Gly | Gly | Ala | Leu | Tyr | Glu | Ala | Ser | Ser | Arg | Ser | Ser | Ser | Val | Val |
| | | | 340 | | | | | 345 | | | | | 350 | | |
| Thr | Asp | Tyr | Val | Gly | Tyr | Leu | Ser | Lys | Gly | Gln | Ile | Pro | Pro | Lys | His |
| | | 355 | | | | | 360 | | | | | 365 | | | |
| Ile | Ser | Leu | Val | Asn | Leu | Thr | Val | Thr | Leu | Asn | Ile | Asp | Gly | Ser | Lys |
| | 370 | | | | | 375 | | | | | 380 | | | | |
| Tyr | Thr | Ile | Glu | Thr | Val | Arg | Gly | Gly | Pro | Arg | Ser | Tyr | Lys | Leu | Arg |
| 385 | | | | | 390 | | | | | 395 | | | | | 400 |
| Ile | Asn | Glu | Ser | Glu | Val | Glu | Ala | Glu | Ile | His | Xaa | Leu | Arg | Asp | Gly |
| | | | | 405 | | | | | 410 | | | | | 415 | |
| Gly | Xaa | Leu | Met | Gln | Xaa | Asp | Gly | Asn | Ser | His | Val | Ile | Tyr | Ala | Glu |
| | | | 420 | | | | | 425 | | | | | 430 | | |
| Thr | Glu | Ala | Xaa | Gly | Thr | Arg | Leu | Leu | Ile | Asn | Gly | Arg | Thr | Cys | Leu |
| | | 435 | | | | | 440 | | | | | 445 | | | |
| Leu | Gln | Lys | Glu | His | Asp | Pro | Ser | Arg | Leu | Leu | Ala | Asp | Thr | Pro | Cys |
| | 450 | | | | | 455 | | | | | 460 | | | | |
| Lys | Leu | Leu | Arg | Phe | Leu | Val | Ala | Asp | Xaa | Ser | His | Val | Val | Ala | Asp |
| 465 | | | | | 470 | | | | | 475 | | | | | 480 |
| Thr | Pro | Tyr | Ala | Glu | Val | Glu | Ala | Met | Lys | Met | | | | | |
| | | | | 485 | | | | | 490 | | | | | | |

( 2 ) INFORMATION FOR SEQ ID NO:110:

( i ) SEQUENCE CHARACTERISTICS:
        ( A ) LENGTH: 436 base pairs
        ( B ) TYPE: Nucleic acid
        ( C ) STRANDEDNESS: Single
        ( D ) TOPOLOGY: Linear ( i i ) MOLECULE TYPE: Oligonucleotide ( x i ) SEQUENCE DESCRIPTION: SEQ ID NO:110:

```
TCTAGACTTT AACGAGATTC GTCAACTGCT GACAACTATT GCACAAACAG ATATCGCGGA    60
AGTAACGCTC AAAAGTGATG ATTTTGAACT AACGGTGCGT AAAGCTGTTG GTGTGAATAA   120
TAGTGTTGTG CCGGTTGTGA CAGCACCCTT GAGTGGTGTG GTAGGTTCGG GATTGCCATC   180
GGCTATACCG ATTGTAGCCC ATGCTGCCCA ATCTCCATCT CCAGAGCCGG GAACAAGCCG   240
TGCTGCTGAT CATGCTGTCA CGAGTTCTGG CTCACAGCCA GGAGCAAAAA TCATTGACCA   300
AAAATTAGCA GAAGTGGCTT CCCCAATGGT GGGAACATTT TACCGCGCTC CTGCACCAGG   360
TGAAGCGGTA TTTGTGGAAG TCGGCGATCG CATCCGTCAA GGTCAAACCG TCTGCATCAT   420
CGAAGCGATG AAAAUG                                                   436
```

( 2 ) INFORMATION FOR SEQ ID NO:111:

( i ) SEQUENCE CHARACTERISTICS:
        ( A ) LENGTH: 145 amino acids
        ( B ) TYPE: Amino acid
        ( C ) STRANDEDNESS: Single
        ( D ) TOPOLOGY: Linear (  i  i  ) MOLECULE TYPE: Peptide (  x  i  ) SEQUENCE DESCRIPTION: SEQ ID NO:111:

Leu Asp Phe Asn Glu Ile Arg Gln Leu Leu Thr Thr Ile Ala Gln Thr
            5                   10                  15
Asp Ile Ala Glu Val Thr Leu Lys Ser Asp Asp Phe Glu Leu Thr Val
            20                  25                  30
Arg Lys Ala Val Gly Val Asn Asn Ser Val Val Pro Val Val Thr Ala
            35                  40                  45
Pro Leu Ser Gly Val Val Gly Ser Gly Leu Pro Ser Ala Ile Pro Ile
            50                  55                  60
Val Ala His Ala Ala Pro Ser Pro Ser Pro Glu Pro Gly Thr Ser Arg
65                  70                  75                  80
Ala Ala Asp His Ala Val Thr Ser Ser Gly Ser Gln Pro Gly Ala Lys
                85                  90                  95
Ile Ile Asp Gln Lys Leu Ala Glu Val Ala Ser Pro Met Val Gly Thr
            100                 105                 110
Phe Tyr Arg Ala Pro Ala Pro Gly Glu Ala Val Phe Val Glu Val Gly
            115                 120                 125
Asp Arg Ile Arg Gln Gly Gln Thr Val Cys Ile Ile Glu Ala Met Lys
    130                 135                 140
Met
145

( 2 ) INFORMATION FOR SEQ ID NO:112:

( i ) SEQUENCE CHARACTERISTICS:
        ( A ) LENGTH: 22 base units
        ( B ) TYPE: Nucleic acid
        ( C ) STRANDEDNESS: Single
        ( D ) TOPOLOGY: Linear ( i i ) MOLECULE TYPE: Oligonucleotide ( i x ) FEATURE:
        ( A ) NAME/KEY: N
        ( B ) LOCATION: 11, 14
        ( C ) IDENTIFICATION METHOD: N = A, G, C, T ( x i ) SEQUENCE DESCRIPTION: SEQ ID NO:112:

TCGAATTCGT NATNATHAAR GC                    22

( 2 ) INFORMATION FOR SEQ ID NO:113:

( i ) SEQUENCE CHARACTERISTICS:
        ( A ) LENGTH: 22 base pairs
        ( B ) TYPE: Nucleic acid
        ( C ) STRANDEDNESS: Single
        ( D ) TOPOLOGY: Linear ( i i ) MOLECULE TYPE: Oligonucleotide ( i x ) FEATURE:
        ( A ) NAME/KEY: N
        ( B ) LOCATION: 17
        ( C ) IDENTIFICATION METHOD: N = A, G, C, T ( x i ) SEQUENCE DESCRIPTION: SEQ ID NO:113:

GCTCTAGAGK RTGYTCNACY TC                    22

( 2 ) INFORMATION FOR SEQ ID NO:114:

( i ) SEQUENCE CHARACTERISTICS:
        ( A ) LENGTH: 21 base pairs
        ( B ) TYPE: Nucleic acid
        ( C ) STRANDEDNESS: Single
        ( D ) TOPOLOGY: Linear ( i i ) MOLECULE TYPE: Oligonucleotide ( x i ) SEQUENCE DESCRIPTION: SEQ ID NO:114:

GCTCTAGAAT ACTATTTCCT G 21

( 2 ) INFORMATION FOR SEQ ID NO:115:

( i ) SEQUENCE CHARACTERISTICS:
        ( A ) LENGTH: 22 base pairs
        ( B ) TYPE: Nucleic acid
        ( C ) STRANDEDNESS: Single
        ( D ) TOPOLOGY: Linear ( i i ) MOLECULE TYPE: Oligonucleotide ( i x ) FEATURE:
        ( A ) NAME/KEY: N
        ( B ) LOCATION: 10, 20
        ( C ) IDENTIFICATION METHOD: N =A, G, C, T ( x i ) SEQUENCE DESCRIPTION: SEQ ID NO:115:

TCGAATTCWN CATYTTCATN RC 22

( 2 ) INFORMATION FOR SEQ ID NO:116:

( i ) SEQUENCE CHARACTERISTICS:
        ( A ) LENGTH: 23 base pairs
        ( B ) TYPE: Nucleic acid
        ( C ) STRANDEDNESS: Single
        ( D ) TOPOLOGY: Linear ( i i ) MOLECULE TYPE: Oligonucleotide ( x i ) SEQUENCE DESCRIPTION: SEQ ID NO:116:

GCTCTAGAYT TYAAYGARAT HMG 23

CYANOBACTERIAL AND PLANT ACETYL-COA CARBOXYLASE

The U.S. Government may own rights in the present invention pursuant to USDA Grant #90-34190-5207 Through the Midwest Biotechnology Consortium.

DESCRIPTION

1. Technical Field of the Invention

The present invention relates to polynucleotides and polypeptides of acetyl-CoA carboxylase in cyanobacteria and plants. Polynucleotides encoding acetyl-CoA carboxylase have use in conferring herbicide resistance and in determining the herbicide resistance of plants in a breeding program.

2. Background of the Invention

Acetyl-CoA carboxylase (ACC) is the first enzyme of the biosynthetic pathway to fatty acids. It belongs to a group of carboxylases that use biotin as cofactor and bicarbonate as a source of the carboxyl group. ACC catalyzes the addition of $CO_2$ to acetyl-CoA to yield malonyl-CoA in two steps as shown below.

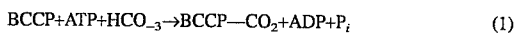

First, biotin becomes carboxylated at the expense of ATP. The carboxyl group is then transferred to Ac-CoA [Knowles, 1989]. This irreversible reaction is the committed step in fatty acid synthesis and is a target for multiple regulatory mechanisms. Reaction (1) is catalyzed by biotin carboxylase (BC); reaction (2) by transcarboxylase (TC); BCCP=biotin carboxyl carrier protein.

ACC purified from *E. coli* contains three distinct, separable components.: biotin carboxylase (BC), a dimer of 49-kD monomers, biotin carboxyl carrier protein (BCCP) a dimer of 17-kD monomers and transcarboxylase (TC), a tetramer containing two each of 33-kD and 35-kD subunits. The biotin prosthetic group is covalently attached to the γ-amino group of a lysine residue of BCCP. The primary structure of *E. coli* BCCP and BC is known (fabE and fabG genes, respectively, have been cloned and sequenced) [Alix, 1989; Maramatsu, et al., 1989; Li, et al., 1992]. In bacteria, fatty acids are primarily precursors of phospholipids rather than storage fuels, and so ACC activity is coordinated with cell growth and division.

Rat and chicken ACC consist of a dimer of about 265 kD (rat has also a 280 kD isoform) subunits that contains all of the bacterial enzyme activities. Both mammalian and avian ACC are cytoplasmic enzymes and their substrate is transported out of mitochondria via citrate. ACC content and/or activity varies with the rate of fatty acid synthesis or energy requirements in different nutritional, hormonal and developmental states. ACC mRNA is transcribed using different promoters and can be regulated by alternative splicing. ACC catalytic activity is regulated allosterically by a number of metabolites and by reversible phosphorylation of the enzyme. The primary structure of rat and chicken enzymes, and the primary structure of the 5'-untranslated region of mRNA have been deduced from cDNA sequences [Lopez-Casillas, et al., 1988; Takai, et al., 1988]. The primary structure of yeast ACC has also been determined [Feel, et al., 1992].

Studies on plant ACC are far less advanced [Harwood, 1988]. It was originally thought that plant ACC consisted of low molecular weight dissociable subunits similar to those of bacteria. Those results appeared to be due to degradation of the enzyme during purification. More recent results indicate that the wheat enzyme, as well as those from parsley and rape, are composed of two about 220 kD monomers, similar to the enzyme from rat and chicken [Harwood, 1988; Egin-Buhler, et al., 1983; Wurtelle, et al., 1990; Slabas, et al., 1985]. The plant ACC is located entirely in the stroma of plastids, where all plant fatty acid synthesis occurs. No plant gene encoding ACC has been reported to date. The gene must be nuclear because no corresponding sequence is seen in the complete chloroplast DNA sequences of tobacco, liverwort or rice. ACC, like the vast majority of chloroplast proteins which are encoded in nuclear DNA, must be synthesized in the cytoplasm and then transported into the chloroplast, probably requiring a chloroplast transport sequence. Although the basic features of plant ACC must be the same as those of prokaryotic and other eucaryotic ACCs, significant differences can be also expected due, for example, to differences in plant cell metabolism and ACC cellular localization.

Structural similarities deduced from the available amino acid sequences suggest strong evolutionary conservation among biotin carboxylases and biotin carboxylase domains of all biotin-dependent carboxylases. On the contrary, the BCCP domains show very little conservation outside the sequence E(A/V)MKM (lysine residue is biotinylated) which is found in all biotinylated proteins including pyruvate carboxylase and propionyl-CoA carboxylase [Knowles, 1989; Samols, et al., 1988]. It is likely that the three functional domains of ACC located in *E. coli* on separate polypeptides are present in carboxylases containing two (human propionyl-CoA carboxylase) or only one (yeast pyruvate carboxylase, mammalian, avian and probably also plant ACC) polypeptide as a result of gene fusion during evolution.

Several years ago it was shown that aryloxyphenoxypropionates and cyclohexanediones, powerful herbicides effective against monocot weeds, inhibit fatty acid biosynthesis in sensitive plants. Recently it has been determined that ACC is the target enzyme for both of these classes of herbicide. Dicotyledonous plants are resistant to these compounds, as are other eukaryotes and prokaryotes. The mechanisms of inhibition and resistance of the enzyme are not known [Lichtenthaler, 1990].

It has occurred to others that the evolutionary relatedness of cyanobacteria and plants make the former useful sources of cloned genes for the isolation of plant cDNAs. For example, Pecker et al used the cloned gene for the enzyme phytoene desaturase, which functions in the synthesis of carotenoids, from cyanobacteria as a probe to isolate the cDNA for that gene from tomato [Pecker, et al., 1992].

BRIEF SUMMARY OF THE INVENTION

In one aspect the present invention provides an isolated and purified polynucleotide of from about 1350 to about 40,000 base pairs that encodes a polypeptide having the ability to catalyze the carboxylation of a biotin carboxyl carrier protein of a cyanobacterium. Preferably, that polypeptide is a subunit of acetyl-CoA carboxylase and participates in the carboxylation of acetyl-CoA. In a preferred embodiment, a cyanobacterium is Anabaena or Synechococcus. The biotin carboxyl carrier protein preferably includes the amino acid residue sequence shown in SEQ ID NO:111 or a functional equivalent thereof.

In another preferred embodiment, the polypeptide has the amino acid residue sequence of FIG. 1 or FIG. 2. The polynucleotide preferably includes the DNA sequence of SEQ ID NO:1, the DNA sequence of SEQ ID NO:1 from about nucleotide position 1300 to about nucleotide position 2650 or the DNA sequence of SEQ ID NO:5.

In another aspect, the present invention provides an isolated and purified polynucleotide of from about 480 to about 40,000 base pairs that encodes a biotin carboxyl carrier protein of a cyanobacterium and, preferably Anabaena. The biotin carboxyl carrier protein preferably includes the amino acid residue sequence of SEQ ID NO:111 and the polynucleotide preferably includes the DNA sequence of SEQ ID NO:110.

Another polynucleotide provided by the present invention encodes a plant polypeptide having the ability to catalyze the carboxylation of acetyl-CoA. A plant polypeptide is preferably (1) a monocotyledonous plant polypeptide such as a wheat, rice, maize, barley, rye, oats or timothy grass polypeptide or (2) a dicotyledonous plant polypeptide such as a soybean, rape, sunflower, tobacco, Arabiodopsis, petunia, Canola, pea, bean, tomato, potato, lettuce, spinach, alfalfa, cotton or carrot polypeptide. Preferably, that polypeptide is a subunit of ACC and participates in the carboxylation of acetyl-CoA.

Such a polynucleotide preferably includes the nucleotide sequence of SEQ ID NO:108 and encodes the amino acid residue sequence of SEQ ID NO:109.

In yet another aspect, the present invention provides an isolated and purified DNA molecule comprising a promoter operatively linked to a coding region that encodes (1) a polypeptide having the ability to catalyze the carboxylation of a biotin carboxyl carrier protein of a cyanobacterium, (2) a biotin carboxyl carrier protein of a cyanobacterium or (3) a plant polypeptide having the ability to catalyze the carboxylation of acetyl-CoA, which coding region is operatively linked to a transcription-terminating region, whereby said promoter drives the transcription of said coding region.

In another aspect, the present invention provides an isolated polypeptide having the ability to catalyze the carboxylation of a biotin carboxyl carrier protein of a cyanobacterium such as Anabaena or Synechococcus. Preferably a biotin carboxyl carrier protein includes the amino acid sequence of SEQ ID NO:111 and the polypeptide has the amino acid residue sequence of FIG. 1 or FIG. 2 (SEQ ID NO:5 and SEQ ID NO:6).

The present invention also provides (1) an isolated and purified biotin carboxyl carrier protein of a cyanobacterium such as Anabaena, which protein includes the amino acid residue sequence of SEQ ID NO:111 and (2) an isolated and purified plant polypeptide having a molecular weight of about 220 kD, dimers of which have the ability to catalyze the carboxylation of acetyl-CoA.

In yet another aspect, the present invention provides a process of increasing the herbicide resistance of a monocotyledonous plant comprising transforming the plant with a DNA molecule comprising a promoter operatively linked to a coding region that encodes a herbicide resistant polypeptide having the ability to catalyze the carboxylation of acetyl-CoA, which coding region is operatively linked to a transcription-terminating region, whereby the promoter is capable of driving the transcription of the coding region in a monocotyledonous plant.

Preferably, a polypeptide is an acetyl-CoA carboxylase enzyme and, more preferably, a dicotyledonous plant acetyl-CoA carboxylase. In a preferred embodiment, a coding region includes the DNA sequence of SEQ ID NO:108 and a promoter is CaMV35.

The present invention also provides a transformed plant produced in accordance with the above process as well as a transgenic plant and a transgenic plant seed having incorporated into its genome a transgene that encodes a herbicide resistant polypeptide having the ability to catalyze the carboxylation of acetyl-CoA.

In yet another aspect, the present invention provides a process of altering the carboxylation of acetyl-CoA in a cell comprising transforming the cell with a DNA molecule comprising a promoter operatively linked to a coding region that encodes a plant polypeptide having the ability to catalyze the carboxylation of acetyl-CoA, which coding region is operatively linked to a transcription-terminating region, whereby the promoter is capable of driving the transcription of the coding region in the cell.

In a preferred embodiment, a cell is a cyanobacterium or a plant cell and a plant polypeptide is a monocotyledonous plant acetyl-CoA carboxylase enzyme such as wheat acetyl-CoA carboxylase enzyme. The present invention also provides a transformed cyanobacterium produced in accordance with such a process.

The present invention still further provides a process for determining the inheritance of plant resistance to herbicides of the aryloxyphenocypropionate or cyclohexanedione class, which process comprises the steps of:

(a) measuring resistance to herbicides of the aryloxyphenocypropionate or cyclohexanedione class in a parental plant line and in progeny of the parental plant line;

(b) purifying DNA from said parental plant line and the progeny;

(c) digesting the DNA with restriction enzymes to form DNA fragments;

(d) fractionating the fragments on a gel;

(e) transferring the fragments to a filter support;

(f) annealing the fragments with a labelled RFLP probe consisting of a DNA molecule that encodes acetyl-CoA carboxylase or a portion thereof; and (g) detecting the presence of complexes between the fragments and the RFLP probe; and (h) correlating the herbicide resistance of step (a) with the complexes of step (g) and thereby the inheritance of herbicide resistance.

Preferably, the acetyl-CoA carboxylase is a dicotyledonous plant acetyl-CoA carboxylase enzyme or a mutated monocotyledonous plant acetyl-CoA carboxylase that confers herbicide resistance or a hybrid acetyl-CoA carboxylase comprising a portion of a dicotyledonous plant acetyl-CoA carboxylase, a portion of a dicotyledonous plant acetyl-CoA carboxylase or one or more domains of a cyanobacterial acetyl-CoA carboxylase.

In still yet another aspect, the present invention provides a process for identifying herbicide resistant variants of a plant acetyl-CoA carboxylase comprising the steps of:

(a) transforming cyanobacteria with a DNA molecule that encodes a monocotyledonous plant acetyl-CoA carboxylase enzyme to form transformed cyanobacteria;

(b) inactivating cyanobacterial acetyl-CoA carboxylase;

(c) exposing the transformed cyanobacteria to a herbicide that inhibits acetyl-CoA carboxylase activity;

(d) identifying transformed cyanobacteria that are resistant to the herbicide; and (e) characterizing DNA that encodes acetyl-CoA carboxylase from the cyanobacteria of step (d).

BRIEF DESCRIPTION OF THE DRAWINGS

In the drawings which form a portion of the specification:

FIG. 1 shows the complete nucleotide sequence (SEQ ID NO:1) of a HindIII fragment that includes the fabG gene coding biotin carboxylase from the cyanobacterium Anabaena 7120, along with the amino acid sequence (SEQ ID NO:2–4) deduced from the coding sequence of the DNA.

FIG. 2 shows the nucleotide sequence (SEQ ID NO:5) of the coding region of the fabG gene from the cyanobacterium *Anacystis nidulans* R2, along with the amino acid sequence deduced from the coding sequence (SEQ ID NO:6) of the DNA.

FIGS. 3A–3E show an alignment of the amino acid sequences (SEQ ID NOS:6–107 and 109) of the BC proteins from both cyanobacteria and from *E. coli*, the BCCP proteins from Anabaena and from *E. coli*, along with the ACC enzymes from rat and chicken and several other biotin-containing carboxylases. Stars indicate positions that are identical in all sequences or all but one. The conventional one letter abbreviations for amino acids are used. The BC domains are indicated by a solid underline, the BCCP domains by a dashed underline. The symbol # indicates sequences not related to BC and, therefore, not considered in the alignment. The wheat ACC sequence deduced from the sequence of our cloned cDNA fragment is on the top line. Abbreviations used in the Figure are: Wh ACC, wheat ACC; Rt, rat; Ch, chicken; Yt, yeast; Sy ACC, Synechococcus BC; An ACC, Anabaena BC and BCCP proteins; EC ACC, *E. coli* BC and BCCP; Hm PCCA, human propionyl CoA carboxylase; Rt PCCA, rat propionyl CoA carboxylase; Yt PC, yeast pyruvate carboxylase.

FIG. 6 shows the nucleotide sequence (SEQ ID NO:108) of a portion of the wheat cDNA corresponding to ACC. The amino acid sequence (SEQ ID NO:109) deduced from the nucleotide sequence is also shown. The underlined sequences correspond to the primer sites shown in FIG. 5. A unique sequence was found for the BC domain, suggesting that a single mRNA was the template for the final amplified products. For the sequence between the BC and BCCP domains, three different variants were found among four products sequenced, suggesting that three different gene transcripts were among the amplified products. This is not unexpected because wheat is hexaploid, i.e. it has three pairs of each chromosome.

FIG. 8 shows the nucleotide sequence (SEQ ID NO:110) of a PCR product corresponding to a portion of the fabE gene encoding about 75% of the biotin carboxyl carrier protein from the cyanobacterium Anabaena, along with the amino acid sequence (SEQ ID NO:111) deduced from the coding sequence. The underlined sequences correspond to the primer sites shown in FIG. 7.

DETAILED DESCRIPTION OF THE INVENTION

I. Definitions

Figure 4:
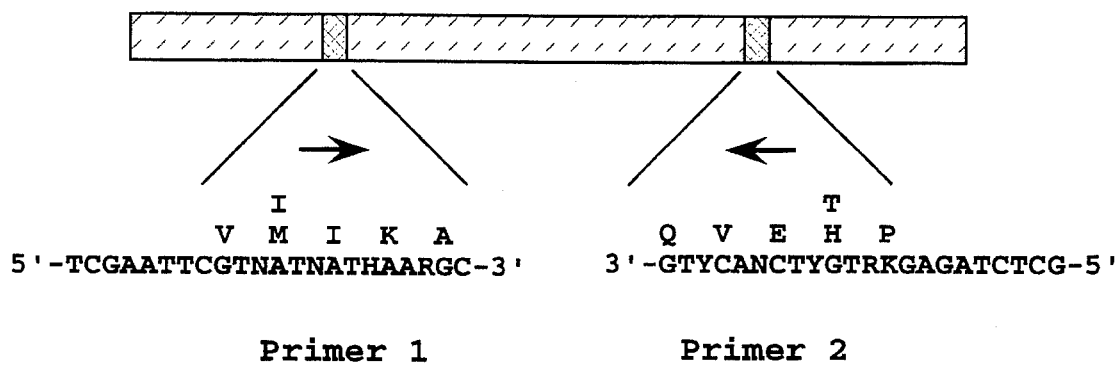
FIG. 4 shows the conserved amino acid sequences used to design primers for the PCR to amplify the BC domain of ACC from wheat. The sequences of the oligonucleotide primers (SEQ ID NOS:112 and 113) are also shown. In this and other figures showing primer sequences, A means adenine, C means cytosine, G means guanine, T means thymine, N means all four nucleotides, Y means T or C, R means A or G, K means G or T, M means A or C, W means A or T, and H means A, C or T.

The following words and phrases have the meanings set forth below.

Expression: The combination of intracellular processes, including transcription and translation undergone by a coding DNA molecule such as a structural gene to produce a polypeptide.

Promoter: A recognition site on a DNA sequence or group of DNA sequences that provide an expression control element for a structural gene and to which RNA polymerase specifically binds and initiates RNA synthesis (transcription) of that gene.

Regeneration: The process of growing a plant from a plant cell (e.g. plant protoplast or explant).

Structural gene: A gene that is expressed to produce a polypeptide.

Transformation: A process of introducing an exogenous DNA sequence (e.g. a vector, a recombinant DNA molecule) into a cell or protoplast in which that exogenous DNA is incorporated into a chromosome or is capable of autonomous replication.

Transformed cell: A cell whose DNA has been altered by the introduction of an exogenous DNA molecule into that cell.

Transgenic cell: Any cell derived or regenerated from a transformed cell or derived from a transgenic cell. Exemplary transgenic cells include plant calli derived from a transformed plant cell and particular cells such as leaf, root, stem, e.g. somatic cells, or reproductive (germ) cells obtained from a transgenic plant.

Transgenic plant: A plant or progeny thereof derived from a transformed plant cell or protoplast, wherein the plant DNA contains an introduced exogenous DNA molecule not originally present in a native, non-transgenic plant of the same strain. The terms "transgenic plant" and "transformed plant" have sometimes been used in the art as synonymous terms to define a plant whose DNA contains an exogenous DNA molecule. However, it is thought more scientifically correct to refer to a regenerated plant or callus obtained from a transformed plant cell or protoplast as being a transgenic plant, and that usage will be followed herein.

Vector: A DNA molecule capable of replication in a host cell and/or to which another DNA segment can be operatively linked so as to bring about replication of the attached segment. A plasmid is an exemplary vector.

Certain polypeptides are disclosed herein as amino acid residue sequences. Those sequences are written left to right in the direction from the amino to the carboxy terminus. In accordance with standard nomenclature, amino acid residue sequences are denominated by either a single letter or a three letter code as indicated below.

| Amino Acid Residue | 3-Letter Code | 1-Letter Code |
| --- | --- | --- |
| Alanine | Ala | A |
| Arginine | Arg | R |
| Asparagine | Asn | N |
| Aspartic Acid | Asp | D |
| Cysteine | Cys | C |
| Glutamine | Gln | Q |
| Glutamic Acid | Glu | E |
| Glycine | Gly | G |

-continued

| Amino Acid Residue | 3-Letter Code | 1-Letter Code |
|---|---|---|
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

The present invention provides polynucleotides and polypeptides relating to a whole or a portion of acetyl-CoA carboxylase (ACC) of cyanobacteria and plants as well as processes using those polynucleotides and polypeptides.

II. Polynucleotides

As used herein the term "polynucleotide" means a sequence of nucleotides connected by phosphodiester linkages. A polynucleotide of the present invention can comprise from about 2 to about several hundred thousand base pairs. Preferably, a polynucleotide comprises from about 5 to about 150,000 base pairs. Preferred lengths of particular polynucleotides are set hereinafter.

A polynucleotide of the present invention can be a deoxyribonucleic acid (DNA) molecule or a ribonucleic acid (RNA) molecule. Where a polynucleotide is a DNA molecule, that molecule can be a gene or a cDNA molecule. Nucleotide bases are indicated herein by a single letter code: adenine (A), guanine (G), thymine (T), cytosine (C), and uracil (U).

A. Cyanobacteria

In one embodiment, the present invention contemplates an isolated and purified polynucleotide of from about 1350 to about 40,000 base pairs that encodes a polypeptide having the ability to catalyze the carboxylation of a biotin carboxyl carrier protein of a cyanobacterium.

Preferably, a biotin carboxyl carrier protein (BCCP) is derived from a cyanobacterium such as Anabaena or Synechococcus. A preferred Anabaena is Anabaena 7120. A preferred Synechococcus is *Anacystis nidulans* R2 (*Synechococcus sp. strain pcc*7942). A biotin carboxyl carrier protein preferably includes the amino acid residue sequence shown in SEQ ID NO:111 or a functional equivalent thereof.

Figure 1A:
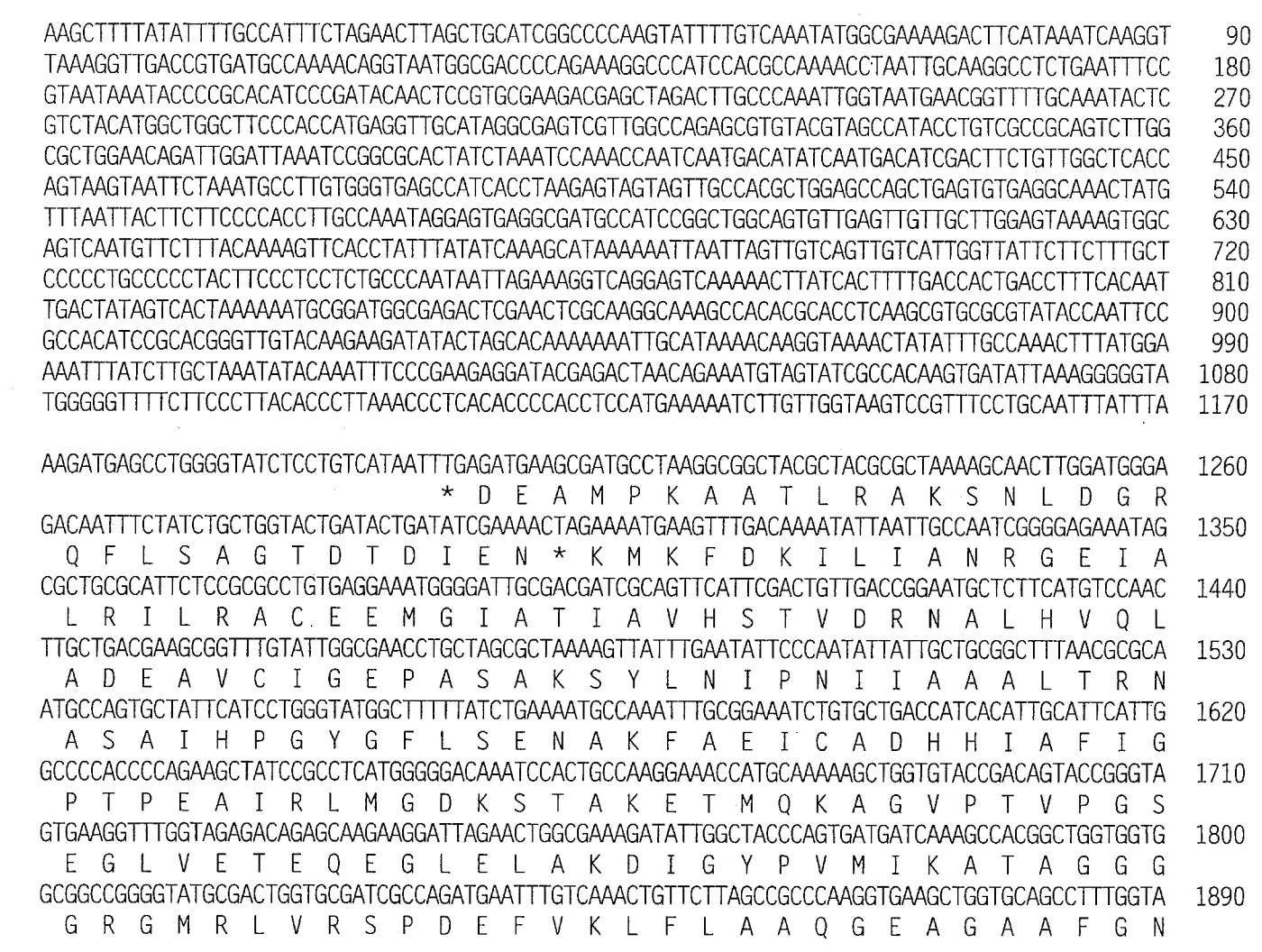

Preferably, a polypeptide is a biotin carboxylase enzyme of a cyanobacterium, which enzyme is a subunit of acetyl-CoA carboxylase and participates in the carboxylation of acetyl-CoA. In a preferred embodiment, a polypeptide encoded by such a polynucleotide has the amino acid residue sequence of FIG. 1 or FIG. 2 (SEQ ID NO:5 and SEQ ID NO:6), or a functional equivalent of those sequences.

A polynucleotide preferably includes the DNA sequence of SEQ ID NO:1 (FIG. 1) or the DNA sequence of SEQ ID NO:1 (FIG. 1) from about nucleotide position 1300 to about nucleotide position 2650.

The polynucleotide of SEQ ID NO:1 contains a gene that encodes the enzyme biotin carboxylase (BC) from the cyanobacterium Anabaena. This gene was cloned in the following way: total DNA from Anabaena was digested with various restriction enzymes, fractionated by gel electrophoresis, and blotted onto GeneScreen Plus (DuPont). The blot was hybridized at low stringency (1M NaCl, 57° C.) with a probe consisting of a SstII-PstI fragment containing about 90% of the coding region of the fabG gene from *E. coli*. This probe identified a 3.1-kb HindIII fragment in the Anabaena digest that contained similar sequences. A mixture of about 3-kb HindIII fragments of Anabaena DNA was purified, then digested with NheI, yielding a HindIII-NheI fragment of 1.6 kb that hybridized with the fabG probe. The 1.6-kb region was purified by gel electrophoresis and cloned into pUC18.

Plasmid minipreps were made from about 160 colonies, of which four were found to contain the 1.6-kb HindIII-NheI fragment that hybridized with the fabG probe. The 1.6-kb Anabaena fragment was then used as probe to screen, at high stringency (1M NaCl, 65° C.), a cosmid library of Anabaena DNA inserts averaging 40 kb in size. Five were found among 1920 tested, all of which contained the same size HindIII and NheI fragments as those identified by the *E. coli* probe previously. From one of the cosmids, the 3.1-kb HindIII fragment containing the Anabaena fabG gene was subcloned into pUC18 and sequenced using the dideoxy chain termination method. The complete nucleotide sequence of this fragment is shown in FIG. 1 (SEQ ID NO:1 and SEQ ID NO:2).

A similar procedure was used to clone the fabG gene from Synechococcus. In this case, the initial Southern hybridization showed that the desired sequences were contained in part on an 0.8-kb BamHI-PstI fragment. This size fragment was purified in two steps and cloned into the plasmid Bluescript KS. Minipreps of plasmids from 200 colonies revealed two that contained the appropriate fragment of Synechococcus DNA. This fragment was used to probe, at high stringency, a library of Synechococcus inserts in the cosmid vector pWB79. One positive clone was found among 1728 tested. This cosmid contained a 2-kb BamHI and a 3-kb PstI fragment that had previously been identified by the *E. coli* fabG probe in digests of total Synechococcus DNA. Both fragments were subcloned from the cosmid into Bluescript KS and 2.4 kb, including the coding part of the fabG gene, were sequenced. The complete sequence of the coding region of the Synechococcus fabG gene is shown in FIG. 2 (SEQ ID NO:5 and SEQ ID NO:6).

In another aspect, the present invention provides an isolated and purified polynucleotide of from about 480 to about 40,000 base pairs that encodes a biotin carboxyl carrier protein of a cyanobacterium. That biotin carboxyl carrier protein preferably includes the amino acid residue sequence of FIG. 8 (SEQ ID NO:111 ) or a functional equivalent thereof. A preferred polynucleotide that encodes that polypeptide includes the DNA sequence of SEQ ID NO:110 (FIG. 8).

B. Plants

Another polynucleotide contemplated by the present invention encodes a plant polypeptide having the ability to catalyze the carboxylation of acetyl-CoA. Such a plant polypeptide is preferably a monocotyledonous or a dicotyledonous plant acetyl-CoA carboxylase enzyme.

An exemplary and preferred monocotyledonous plant is wheat, rice, maize, barley, rye, oats or timothy grass. An exemplary and preferred dicotyledonous plant is soybean, rape, sunflower, tobacco, Arabidopsis, petunia, pea, Canola, bean, tomato, potato, lettuce, spinach, alfalfa, cotton or carrot.

A monocotyledonous plant polypeptide is preferably wheat ACC, which ACC includes the amino acid residue sequence of SEQ ID NO:109 (FIG. 6) or a functional equivalent thereof. A preferred polynucleotide that encodes such a polypeptide includes the DNA sequence of SEQ ID NO:108 (FIG. 6).

Amino acid sequences of biotin carboxylase (BC) from Anabaena and Synechococcus show great similarity with amino acid residue sequences from other ACC enzymes as well as with the amino acid residue sequences of other biotin-containing enzymes (See FIG. 3). Based on that homology, the nucleotide sequences shown in FIG. 4 (SEQ ID NO:112 and SEQ ID NO:113) were chosen for the construction of primers for polymerase chain reaction amplification of a corresponding region of the gene for ACC from wheat. Those primers have the nucleotide sequences shown below:

Primer 1 (SEQ ID NO:112)
5' TCGAATTCGTNATNATHAARGC 3';

Primer 2 (SEQ ID NO:113)
5' GCTCTAGAGKRTGYTCNACYTG 3';

where N is A, C, G or T; H is A, C or T; R is A or G; Y is T or C and K is G or T. Primers 1 and 2 comprise a 14-nucleotide specific sequence based on a conserved amino acid sequence and an 8-nucleotide extension at the 5'-end of the primer to provide anchors for rounds of amplification after the first round and to provide convenient restriction sites for analysis and cloning.

cDNA amplification began with a preparation of total polyA-containing mRNA from eight day-old green plants (*Triticum aestivum* var. Era as described in [Lamppa, et al., 1992]). The first strand of cDNA was synthesized using random hexamers as primers for AMV reverse transcriptase following procedures described in [Haymerle, et al., 1986], with some modifications. Reverse transcriptase was inactivated by heat and low molecular weight material was removed by filtration.

The PCR was initiated by the addition of polymerase at 95° C. Amplification was for 45 cycles, each 1 min at 95°, 1 min at 42°–46° and 2 min at 72° C. Both the reactions using Anabaena DNA and the single-stranded wheat cDNA as template yielded about 440 base pair (bp) products. The wheat product was eluted from a gel and reamplified using the same primers. That product, also 440 bp, was cloned into the Invitrogen (San Diego, Calif.) vector pCR1000 using their A/T tail method, and sequenced.

In eukaryotic ACCs, a BCCP domain is located about 300 amino acids away from the end of the BC domain, on the C-terminal side. Therefore, it is possible to amplify the cDNA covering the interval between the BC and BCCP domains using primers from the C-terminal end of the BC domain and the conserved MKM region of the BCCP. The BC primer was based on the wheat cDNA sequence obtained as described above. Those primers, each with 6- or 8-base 5'-extensions, are shown below and in FIG. 5.

Primer 3 (SEQ ID NO:114)
5' GCTCTAGAATACTATTTCCTG 3'

Primer 4 (SEQ ID NO:115)
5' TCGAATTCWNCATYTTCATNRC 3'

N, R and Y are as defined above. W is A or T. The BC primer (Primer 3) was based on the wheat cDNA sequence obtained as described above. The MKM primer (primer 4) was first checked by determining whether it would amplify the fabE gene coding BCCP from Anabaena DNA. This PCR was primed at the other end by using a primer based on the N-terminal amino acid residue sequence as determined on protein purified from Anabaena extracts by affinity chromatography. Those primers are shown below and in FIG. 7.

Primer 5 (SEQ ID NO:116)
5' GCTCTAGAYTTYAAYGARATHMG 3'

Primer 4 (SEQ ID NO:115)
5' TCGAATTCWNCATYTTCATNRC 3'

H, N, R, T, Y and W are as defined above. M is A or C. This amplification (using the conditions described above) yielded the correct fragment of the Anabaena fabE gene, which was used to identify cosmids that contained the entire fabE gene and flanking DNA. An about 4 kb XbaI fragment containing the gene was cloned into the vector Bluescript KS for sequencing.

Primers 3 and 4 were then used to amplify the intervening sequence in wheat cDNA. Again, the product of the first PCR was eluted and reamplified by another round of PCR, then cloned into the Invitrogen vector pCRII.

The complete 1.1 kb of the amplified DNA was sequenced, shown in FIG. 6, (SEQ ID NO:108); nucleotides 376–1473. The nucleotide sequence of the BC domain is also shown in FIG. 6 (SEQ ID NO:108), nucleotides 1–422. Three clones of the BC domain gave the sequence shown. Four clones of the 1.1-kb fragment differed at several positions, corresponding to three closely related sequences, all of which are indicated in the Figure. Most of the sequence differences are in the third codon position and are silent in terms of the amino acid sequence.

The amino acid sequence of the polypeptide predicted from the cDNA sequence for this entire fragment of wheat cDNA (1473 nucleotides) is compared with the amino acid sequences of other ACC enzymes and related enzymes from various sources in FIG. 3. The most significant identities are with the ACC of rat, chicken and yeast, as shown in the table below. Less extensive similarities are evident with the BC subunits of bacteria and the BC domains of other enzymes such as pyruvate carboxylase of yeast and propionyl CoA carboxylase of rat. The amino acid identities between wheat ACC and other biotin-dependent enzymes, within the BC domain (amino acid residues 312–630 in FIG. 3) are shown below in Table 1.

TABLE 1

|  | % identity with wheat ACC | % identity with rat ACC |
| --- | --- | --- |
| rat ACC | 58 | (100) |
| chicken ACC | 57 | |
| yeast ACC | 56 | |
| Synechococcus ACC | 32 | |
| Anabaena ACC | 30 | |
| E. coli ACC | 33 | |
| rat propionyl CoA carboxylase | 32 | 31 |
| yeast pyruvate carboxylase | 31 | |

C. Probes and Primers

In another aspect, DNA sequence information provided by the invention allows for the preparation of relatively short DNA (or RNA) sequences having the ability to specifically hybridize to gene sequences of the selected polynucleotides disclosed herein. In these aspects, nucleic acid probes of an appropriate length are prepared based on a consideration of a selected ACC gene sequence, e.g., a sequence such as that shown in FIGS. 1, 2, 6 or 8 (SEQ ID NO:110 and SEQ ID NO:111). The ability of such nucleic acid probes to specifically hybridize to an ACC gene sequence lend them particular utility in a variety of embodiments. Most importantly, the probes can be used in a variety of assays for detecting the presence of complementary sequences in a given sample.

In certain embodiments, it is advantageous to use oligonucleotide primers. The sequence of such primers is designed using a polynucleotide of the present invention for use in detecting, amplifying or mutating a defined segment of an ACC gene from a cyanobacterium or a plant using PCR technology. Segments of ACC genes from other organisms can also be amplified by PCR using such primers.

To provide certain of the advantages in accordance with the present invention, a preferred nucleic acid sequence employed for hybridization studies or assays includes sequences that are complementary to at least a 10 to 30 or so long nucleotide stretch of an ACC sequence, such as that shown in FIGS. 1, 2, 6 or 8 (SEQ ID NO:110 and SEQ ID NO:111). A size of at least 10 nucleotides in length helps to ensure that the fragment will be of sufficient length to form a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102, herein incorporated by reference, or by excising selected DNA fragments from recombinant plasmids containing appropriate inserts and suitable restriction sites.

Accordingly, a nucleotide sequence of the invention can be used for its ability to selectively form duplex molecules with complementary stretches of the gene. Depending on the application envisioned, one will desire to employ varying conditions of hybridization to achieve varying degree of selectivity of the probe toward the target sequence. For applications requiring a high degree of selectivity, one will typically desire to employ relatively stringent conditions to form the hybrids, for example, one will select relatively low salt and\or high temperature conditions, such as provided by 0.02M–0.15M NaCl at temperatures of 50° C. to 70° C. These conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate an ACC coding sequences for related species, functional equivalents, or the like, less stringent hybridization conditions will typically be needed in order to allow formation of the heteroduplex. In these circumstances, one may desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it is advantageous to employ a polynucleotide of the present invention in combination with an appropriate label for detecting hybrid formation. A wide variety of appropriate labels are known in the art, including radioactive, enzymatic or other ligands, such as avidin/biotin, which are capable of giving a detectable signal.

In general, it is envisioned that a hybridization probe described herein is useful both as a reagent in solution hybridization as well as in embodiments employing a solid phase. In embodiments involving a solid phase, the test DNA (or RNA) is adsorbed or otherwise affixed to a selected matrix or surface. This fixed nucleic acid is then subjected to specific hybridization with selected probes under desired conditions. The selected conditions depend as is well known in the art on the particular circumstances and criteria required (e.g., on the G+C contents, type of target nucleic acid, source of nucleic acid, size of hybridization probe). Following washing of the matrix to remove nonspecifically bound probe molecules, specific hybridization is detected, or even quantified, by means of the label.

D. Expression Vector

The present invention contemplates an expression vector comprising a polynucleotide of the present invention. Thus, in one embodiment an expression vector is an isolated and purified DNA molecule comprising a promoter operatively linked to an coding region that encodes a polypeptide having the ability to catalyze the carboxylation of a biotin carboxyl carrier protein of a cyanobacterium, which coding region is operatively linked to a transcription-terminating region, whereby the promoter drives the transcription of the coding region.

As used herein, the term "operatively linked" means that a promoter is connected to an coding region in such a way that the transcription of that coding region is controlled and regulated by that promoter. Means for operatively linking a promoter to a coding region are well known in the art.

Where an expression vector of the present invention is to be used to transform a cyanobacterium, a promoter is selected that has the ability to drive and regulate expression in cyanobacteria. Promoters that function in bacteria are well known in the art. An exemplary and preferred promoter for the cyanobacterium Anabaena is the glnA gene promoter. An exemplary and preferred promoter for the cyanobacterium Synechococcus is the psbAl gene promoter. Alternatively, the cyanobacterial fabG gene promoters themselves can be used.

Where an expression vector of the present invention is to be used to transform a plant, a promoter is selected that has the ability to drive expression in plants. Promoters that function in plants are also well known in the art. Useful in expressing the polypeptide in plants are promoters that are inducible, viral, synthetic, constitutive as described by Poszkowski et al., *EMBO J.*, 3:2719 (1989) and Odell et al., *Nature*, 313:810 (1985), and temporally regulated, spatially regulated, and spatiotemporally regulated as given in Chua et al., *Science*, 244:174–181 (1989).

A promoter is also selected for its ability to direct the transformed plant cell's or transgenic plant's transcriptional activity to the coding region. Structural genes can be driven by a variety of promoters in plant tissues. Promoters can be near-constitutive, such as the CaMV 35S promoter, or tissue specific or developmentally specific promoters affecting dicots or monocots.

Where the promoter is a near-constitutive promoter such as CaMV 35S, increases in polypeptide expression are found in a variety of transformed plant tissues (e.g. callus, leaf, seed and root). Alternatively, the effects of transformation can be directed to specific plant tissues by using plant integrating vectors containing a tissue-specific promoter.

An exemplary tissue-specific promoter is the Lectin promoter, which is specific for seed tissue. The Lectin protein in soybean seeds is encoded by a single gene (Le1) that is only expressed during seed maturation and accounts for about 2 to about 5 percent of total seed mRNA. The Lectin gene and seed-specific promoter have been fully characterized and used to direct seed specific expression in transgenic tobacco plants. See, e.g., Vodkin et al., *Cell*, 34:1023 (1983) and Lindstrom et al., *Developmental Genetics*, 11:160 (1990).

An expression vector containing a coding region that encodes a polypeptide of interest is engineered to be under control of the Lectin promoter and that vector is introduced into plants using, for example, a protoplast transformation method. Dhir et al., *Plant Cell Reports*, 10:97 (1991). The expression of the polypeptide is directed specifically to the seeds of the transgenic plant.

A transgenic plant of the present invention produced from a plant cell transformed with a tissue specific promoter can be crossed with a second transgenic plant developed from a plant cell transformed with a different tissue specific promoter to produce a hybrid transgenic plant that shows the effects of transformation in more than one specific tissue.

Exemplary tissue-specific promoters are corn sucrose synthetase 1 (Yang et al. *Proc. Natl. Acad. Sci. U.S.A.*, 87:4144–48 (1990)), corn alcohol dehydrogenase 1 (Vogel et al., *J. Cell Biochem.*, (supplement 13D, 312) (1989)), corn zein 19 KD gene (storage protein) (Boston et al., *Plant Physiol.*, 83:742–46), corn light harvesting complex (Simpson, *Science*, 233:34 (1986), corn heat shock protein (O'Dell et al., *Nature*, 313:810–12 (1985), pea small subunit RuBP Carboxylase (Poulsen et al., *Mol. Gen. Genet.*, 205:193–200 (1986); Cashmore et al., *Gen. Eng. of Plants*, Plenum Press, New York, 29–38 (1983), Ti plasmid mannopine synthase (Langridge et al., *Proc. Natl. Acad. Sci. USA*, 86:3219–3223 (1989), Ti plasmid nopaline synthase (Langridge et al., *Proc. Natl. Acad. Sci. USA*, 86:3219–3223 (1989), petunia chalcone isomerase (Van Tunen et al., *EMBO J.*, 7:1257 (1988), bean glycine rich protein 1 (Keller et al., *EMBO J.*, 8:1309–14 (1989), CaMV 35s transcript (O'Dell et al., *Nature*, 313:810–12 (1985) and Potato patatin (Wenzler et al., *Plant Mol. Biol.*, 12:41–50 (1989). Preferred promoters are the cauliflower mosaic virus (CaMV 35S) promoter and the S-E9 small subunit RuBP carboxylase promoter.

The choice of which expression vector and ultimately to which promoter a polypeptide coding region is operatively linked depends directly on the functional properties desired, e.g. the location and timing of protein expression, and the host cell to be transformed. These are well known limitations inherent in the art of constructing recombinant DNA molecules. However, a vector useful in practicing the present invention is capable of directing the expression of the polypeptide coding region to which it is operatively linked.

Typical vectors useful for expression of genes in higher plants are well known in the art and include vectors derived from the tumor-inducing (Ti) plasmid of *Agrobacterium tumefaciens* described by Rogers et al., *Meth. in Enzymol.*, 153:253–277 (1987). However, several other plant integrating vector systems are known to function in plants including pCaMVCN transfer control vector described by Fromm et al., *Proc. Natl. Acad. Sci. USA*, 82:5824 (1985). Plasmid pCaMVCN (available from Pharmacia, Piscataway, N.J.) includes the cauliflower mosaic virus CaMV 35S promoter.

In preferred embodiments, the vector used to express the polypeptide includes a selection marker that is effective in a plant cell, preferably a drug resistance selection marker. One preferred drug resistance marker is the gene whose expression results in kanamycin resistance; i.e., the chimeric gene containing the nopaline synthase promoter, Tn5 neomycin phosphotransferase II and nopaline synthase 3' nontranslated region described by Rogers et al., in *Methods For Plant Molecular Biology*, A. Weissbach and H. Weissbach, eds., Academic Press Inc., San Diego, Calif. (1988).

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

Means for preparing expression vectors are well known in the art. Expression (transformation vectors) used to transform plants and methods of making those vectors are described in U.S. Pat. Nos. 4,971,908, 4,940,835, 4,769,061 and 4,757,011, the disclosures of which are incorporated herein by reference. Those vectors can be modified to include a coding sequence in accordance with the present invention.

A variety of methods has been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

A coding region that encodes a polypeptide having the ability to catalyze the carboxylation of a biotin carboxyl carrier protein of a cyanobacterium is preferably a biotin carboxylase enzyme of a cyanobacterium, which enzyme is a subunit of acetyl-CoA carboxylase and participates in the carboxylation of acetyl-CoA. In a preferred embodiment, such a polypeptide has the amino acid residue sequence of FIG. 1 or FIG. 2, or a functional equivalent of those sequences. In accordance with such an embodiment, a coding region comprises the entire DNA sequence of SEQ ID NO:1 (FIG. 1) or the DNA sequence of SEQ ID NO:1 (FIG. 1) from about nucleotide position 1300 to about nucleotide position 2650 or the DNA sequence of SEQ ID NO:5 (FIG. 2).

In another embodiment, an expression vector comprises a coding region of from about 480 to about 40,000 base pairs that encodes a biotin carboxyl carrier protein of a cyanobacterium. That biotin carboxyl carrier protein preferably includes the amino acid residue sequence of FIG. 8 (SEQ ID NO:111) or a functional equivalent thereof. A preferred such coding region includes the DNA sequence of SEQ ID NO:110 (FIG. 8).

In still yet another embodiment, an expression vector comprises a coding region that encodes a plant polypeptide having the ability to catalyze the carboxylation of acetyl-CoA. Such a plant polypeptide is preferably a monocotyledonous or a dicotyledonous plant acetyl-CoA carboxylase enzyme.

A preferred monocotyledonous plant polypeptide encoded by such a coding region is preferably wheat ACC, which ACC includes the amino acid residue sequence of SEQ ID NO:109 (FIG. 6) or a functional equivalent thereof. A preferred coding region includes the DNA sequence of SEQ ID NO:108 (FIG. 6).

III. Polypeptide

The present invention contemplates a polypeptide that defines a whole or a portion of an ACC of a cyanobacterium or a plant. In one embodiment, thus, the present invention provides an isolated polypeptide having the ability to catalyze the carboxylation of a biotin carboxyl carrier protein of a cyanobacterium such as Anabaena or Synechococcus. Preferably, a biotin carboxyl carrier protein includes the amino acid sequence of SEQ ID NO:111 and the polypeptide has FIG. 1 or FIG. 2 (SEQ ID NO:5 and SEQ ID NO:6).

The present invention also contemplates an isolated and purified biotin carboxyl carrier protein of a cyanobacterium such as Anabaena, which protein includes the amino acid residue sequence of SEQ ID NO:111.

In another embodiment, the present invention contemplates an isolated and purified plant polypeptide having a molecular weight of about 220 KD, dimers of which have the ability to catalyze the carboxylation of acetyl-CoA. Such a polypeptide preferably includes the amino acid residue sequence of SEQ ID NO:109.

Modification and changes may be made in the structure of polypeptides of the present invention and still obtain a molecule having like or otherwise desirable characteristics. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a polypeptide that defines that polypeptide's biological functional activity, certain amino acid sequence substitutions can be made in a polypeptide sequence (or, of course, its underlying DNA coding sequence) and nevertheless obtain a polypeptide with like or even counterveiling properties (e.g., antagonistic v. agonistic).

In making such changes, the hydropathic index of amino acids may be considered. The importance of the hydropathic amino acid index in conferring interactive biologic function on a protein is generally understood in the art (Kyte & Doolittle, J. Mol. Biol., 157:105–132, 1982). It is known that certain amino acids may be substituted for other amino acids having a similar hydropathic index or score and still result in a protein with similar biological activity. Each amino acid has been assigned a hydropathic index on the basis of their hydrophobicity and charge characteristsics, these are: isoleucine (+4.5); valine (+4.2); leucine (+3.8); phenylalanine (+2.8); cysteine/cystine (+2.5); methionine (+1.9); alanine (+1.8); glycine (–0.4); threonine (–0.7); serine (–0.8); tryptophan (–0.9); tyrosine (–1.3); proline (–1.6); histidine (–3.2); glutamate (–3.5); glutamine (–3.5); aspartate (–3.5); asparagine (–3.5); lysine (–3.9); and arginine (–4.5).

It is believed that the relative hydropathic character of the amino acid determines the secondary structure of the resultant polypeptide, which in turn defines the interaction of the polypeptide with other molecules, for example, enzymes, substrates, receptors, antibodies, antigens, and the like. It is known in the art that an amino acid may be substituted by another amino acid having a similar hydropathic index and still obtain a biological functionally equivalent protein. In such changes, the substitution of amino acids whose hydropathic indices are within ±2 is preferred, those which are within ±1 are particularly preferred, and those within ±0.5 are even more particularly preferred.

Substitution of like amino acids can also be made on the basis of hydrophilicity, particularly where the biological functional equivalent protein or peptide thereby created is intended for use in immunological embodiments. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein.

As detailed in U.S. Pat. No. 4,554,101, the following hydrophilicity values have been asssigned to amino acid residues: arginine (+3.0); lysine (+3.0); aspartate (+3.0±1); glutamate (+3.0±1); serine (+0.3); asparagine (+0.2); glutamine (+0.2); glycine (0); proline (–0.5±1); threonine (–0.4); alanine (–0.5); histidine (–0.5); cysteine (–1.0); methionine (–1.3); valine (–1.5); leucine (–1.8); isoleucine (–1.8); tyrosine (–2.3); phenylalanine (–2.5); tryptophan (–3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

The present invention thus contemplates functional equivalents of the polypeptides set forth above. A polypeptide of the present invention is prepared by standard techniques well known to those skilled in the art. Such techniques include, but are not limited to, isolation and purification from tissues known to contain that polypeptide and expression from cloned DNA using transformed cells.

IV. Transformed or Transgenic Cells or Plants

A cyanobacterium, a plant cell or a plant transformed with an expression vector of the present invention is also contemplated. A transgenic cyanobacterium, plant cell or plant derived from such a transformed or transgenic cell is also contemplated.

Means for transforming cyanobacteria are well known in the art. Typically, means of transformation are similar to those well known means used to transform other bacteria such as E. coli. Synechococcus can be transformed simply by incubation of log-phase cells with DNA. (Golden, et al., 1987)

The application of brief, high-voltage electric pulses to a variety of mammalian and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of clones genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

Methods for DNA transformation of plant cells include Agrobacterium-mediated plant transformation, protoplast transformation, gene transfer into pollen, injection into reproductive organs, injection into immature embryos and particle bombardment. Each of these methods has distinct advantages and disadvantages. Thus, one particular method of introducing genes into a particular plant strain may not necessarily be the most effective for another plant strain, but it is well known which methods are useful for a particular plant strain.

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example, the methods described by Fraley et al., *Biotechnology*, 3:629 (1985) and Rogers et al., *Methods in Enzymology*, 153:253–277 (1987). Further, the integration of the Ti-DNA is a relatively precise process resulting in few rearrangements. The region of DNA to be transferred is defined by the border sequences, and intervening DNA is usually inserted into the plant genome as described by Spielmann et al., *Mol. Gen. Genet.*, 205:34 (1986) and Jorgensen et al., *Mol. Gen. Genet.*, 207:471 (1987).

Modern Agrobacterium transformation vectors are capable of replication in *E. coli* as well as Agrobacterium, allowing for convenient manipulations as described by Klee et al., in *Plant DNA Infectious Agents*, T. Hohn and J. Schell, eds., Springer-Verlag, New York (1985) pp. 179–203.

Moreover, recent technological advances in vectors for Agrobacterium-mediated gene transfer have improved the arrangement of genes and restriction sites in the vectors to facilitate construction of vectors capable of expressing various polypeptide coding genes. The vectors described by Rogers et al., *Methods in Enzymology*, 153:253 (1987), have convenient multi-linker regions flanked by a promoter and a polyadenylation site for direct expression of inserted polypeptide coding genes and are suitable for present purposes. In addition, Agrobacteria containing both armed and disarmed Ti genes can be used for the transformations. In those plant strains where Agrobacterium-mediated transformation is efficient, it is the method of choice because of the facile and defined nature of the gene transfer.

Agrobacterium-mediated transformation of leaf disks and other tissues such as cotyledons and hypocotyls appears to be limited to plants that Agrobacterium naturally infects. Agrobacterium-mediated transformation is most efficient in dicotyledonous plants. Few monocots appear to be natural hosts for Agrobacterium, although transgenic plants have been produced in asparagus using Agrobacterium vectors as described by Bytebier et al., *Proc. Natl. Acad. Sci. USA*, 84:5345 (1987). Therefore, commercially important cereal grains such as rice, corn, and wheat must usually be transformed using alternative methods. However, as mentioned above, the transformation of asparagus using Agrobacterium can also be achieved. See, for example, Bytebier, et al., *Proc. Natl. Acad. Sci. USA*, 84:5345 (1987).

A transgenic plant formed using Agrobacterium transformation methods typically contains a single gene on one chromosome. Such transgenic plants can be referred to as being heterozygous for the added gene. However, inasmuch as use of the word "heterozygous" usually implies the presence of a complementary gene at the same locus of the second chromosome of a pair of chromosomes, and there is no such gene in a plant containing one added gene as here, it is believed that a more accurate name for such a plant is an independent segregant, because the added, exogenous gene segregates independently during mitosis and meiosis.

More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for enhanced carboxylase activity relative to a control (native, non-transgenic) or an independent segregant transgenic plant.

It is to be understood that two different transgenic plants can also be mated to produce offspring that contain two independently segregating added, exogenous genes. Selfing of appropriate progeny can produce plants that are homozygous for both added, exogenous genes that encode a polypeptide of interest. Back-crossing to a parental plant and out-crossing with a non-transgenic plant are also contemplated.

Transformation of plant protoplasts can be achieved using methods based on calcium phosphate precipitation, polyethylene glycol treatment, electroporation, and combinations of these treatments. See, for example, Potrykus et al., *Mol. Gen. Genet.*, 199:183 (1985); Lorz et al., *Mol. Gen. Genet.*, 199:178 (1985); Fromm et al., *Nature*, 319:791 (1986); Uchimya et al., *Mol. Gen. Genet.*, 204:204 (1986); Callis et al., *Genes and Development*, 1:1183 (1987); and Marcotte et al., *Nature*, 335:454 (1988).

Application of these systems to different plant strains depends upon the ability to regenerate that particular plant strain from protoplasts. Illustrative methods for the regeneration of cereals from protoplasts are described in Fujimura et al., *Plant Tissue Culture Letters*, 2:74 (1985); Toriyama et al., *Theor Appl. Genet.*, 73:16 (1986); Yamada et al., *Plant Cell Rep.*, 4:85 (1986); Abdullah et al., *Biotechnology*, 4:1087 (1986).

To transform plant strains that cannot be successfully regenerated from protoplasts, other ways to introduce DNA into intact cells or tissues can be utilized. For example, regeneration of cereals from immature embryos or explants can be effected as described by Vasil, *Biotechnology*, 6:397 (1988). In addition, "particle gun" or high-velocity microprojectile technology can be utilized. (Vasil, 1992)

Using that latter technology, DNA is carried through the cell wall and into the cytoplasm on the surface of small metal particles as described in Klein et al., *Nature*, 327:70 (1987); Klein et al., *Proc. Natl. Acad. Sci. U.S.A.*, 85:8502 (1988); and McCabe et al., *Biotechnology*, 6:923 (1988). The metal particles penetrate through several layers of cells and thus allow the transformation of cells within tissue explants.

Metal particles have been used to successfully transform corn cells and to produce fertile, stable transgenic tobacco plants as described by Gordon-Kamm, W. J. et al., *The Plant Cell*, 2:603–618 (1990); Klein, T. M. et al., *Plant Physiol.*, 91:440–444 (1989); Klein, T. M. et al., *Proc. Natl. Acad. Sci. USA*, 85:8502–8505 (1988); and Tomes, D. T. et al., *Plant Mol. Biol.*, 14:261–268 (1990). Transformation of tissue explants eliminates the need for passage through a protoplast stage and thus speeds the production of transgenic plants.

Thus, the amount of a gene coding for a polypeptide of interest (i.e., a polypeptide having carboxylation activity) can be increased in monocotyledonous plants such as corn by transforming those plants using particle bombardment methods. Maddock et al., *Third International Congress of Plant Molecular Biology*, Abstract 372 (1991). By way of example, an expression vector containing an coding region for a dicotyledonous ACC and an appropriate selectable marker is transformed into a suspension of embryonic maize (corn) cells using a particle gun to deliver the DNA coated on microprojectiles. Transgenic plants are regenerated from transformed embryonic calli that express ACC. Particle bombardment has been used to successfully transform wheat (Vasil et al., 1992).

DNA can also be introduced into plants by direct DNA transfer into pollen as described by Zhou et al., *Methods in Enzymology*, 101:433 (1983); D. Hess, *Intern Rev. Cytol.*, 107:367 (1987); Luo et al., *Plant Mol. Biol. Reporter*, 6:165 (1988). Expression of polypeptide coding genes can be obtained by injection of the DNA into reproductive organs of a plant as described by Pena et al., *Nature*, 325:274 (1987). DNA can also be injected directly into the cells of immature embryos and the rehydration of desiccated embryos as described by Neuhaus et al., *Theor. Appl. Genet.*, 75:30 (1987); and Benbrook et al., in *Proceedings Bio Expo* 1986, Butterworth, Stoneham, Mass., pp. 27–54 (1986).

The development or regeneration of plants from either single plant protoplasts or various explants is well known in the art. See, for example, *Methods for Plant Molecular Biology*, A. Weissbach and H. Weissbach, eds., Academic Press, Inc., San Diego, Calif. (1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by Agrobacterium from leaf explants can be achieved by methods well known in the art such as described by Horsch et al., *Science*, 227:1229–1231 (1985). In this procedure, transformants are cultured in the presence of a selection agent and in a medium that induces the regeneration of shoots in the plant strain being transformed as described by Fraley et al., *Proc. Natl. Acad. Sci. U.S.A.*, 80:4803 (1983).

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, as discussed before. Otherwise, pollen obtained from the regenerated plants is crossed to seed-grown plants of agronomically important, preferably inbred lines. Conversely, pollen from plants of those important lines is used to pollinate regenerated plants.

A transgenic plant of the present invention containing a desired polypeptide is cultivated using methods well known to one skilled in the art. Any of the transgenic plants of the present invention can be cultivated to isolate the desired ACC or fatty acids which are the products of the series of reactions of which that catalyzed by ACC is the first.

A transgenic plant of this invention thus has an increased amount of an coding region (e.g. gene) that encodes a polypeptide of interest. A preferred transgenic plant is an independent segregant and can transmit that gene and its activity to its progeny. A more preferred transgenic plant is homozygous for that gene, and transmits that gene to all of its offspring on sexual mating.

Seed from a transgenic plant is grown in the field or greenhouse, and resulting sexually mature transgenic plants are self-pollinated to generate true breeding plants. The progeny from these plants become true breeding lines that are evaluated for, by way of example, herbicide resistance, preferably in the field, under a range of environmental conditions.

The commercial value of a transgenic plant with increased herbicide resistance or with altered fatty acid production is enhanced if many different hybrid combinations are available for sale. The user typically grows more than one kind of hybrid based on such differences as time to maturity, standability or other agronomic traits. Additionally, hybrids adapted to one part of a country are not necessarily adapted to another part because of differences in such traits as maturity, disease and herbicide resistance. Because of this, herbicide resistance is preferably bred into a large number of parental lines so that many hybrid combinations can be produced.

V. Process of Increasing Herbicide Resistance

Herbicides such as aryloxyphenoxypropionates and cyclohexanediones inhibit the growth of monocotyledonous weeds by interfering with fatty acid biosynthesis of herbicide sensitive plants. ACC is the target enzyme for those herbicides. Dicotyledonous plants, other eukaryotic organisms and prokaryotic organisms are resistant to those compounds.

Thus, the resistance of sensitive monocotyledonous plants to herbicides can be increased by providing those plants with ACC that is not sensitive to herbicide inhibition. The present invention therefore provides a process of increasing the herbicide resistance of a monocotyledonous plant comprising transforming the plant with a DNA molecule comprising a promoter operatively linked to a coding region that encodes a herbicide resistant polypeptide having the ability to catalyze the carboxylation of acetyl-CoA, which coding region is operatively linked to a transcription-terminating region, whereby the promoter is capable of driving the transcription of the coding region in a monocotyledonous plant.

Preferably, a herbicide resistant polypeptide, a dicotyledonous plant polypeptide such as an acetyl-CoA carboxylase enzyme from soybean, rape, sunflower, tobacco, Arabidopsis, petunia, Canola, pea, bean, tomato, potato, lettuce, spinach, alfalfa, cotton or carrot, or functional equivalent thereof. A promoter and a transcription-terminating region are preferably the same as set forth above.

Transformed monocotyledonous plants can be identified using herbicide resistance. A process for identifying a transformed monocotyledonous plant cell comprises the steps of:

(a) transforming the monocotyledonous plant cell with a DNA molecule that encodes a dicotyledonous acetyl-CoA carboxylase enzyme; and (b) determining the resistance of the plant cell to a herbicide and thereby the identification of the transformed monocotyledonous plant cell.

Means for transforming a monocotyledonous plant cell are the same as set forth above.

The resistance of a transformed plant cell to a herbicide is preferably determined by exposing such a cell to an effective herbicidal dose of a preselected herbicide and maintaining that cell for a period of time and under culture conditions sufficient for the herbicide to inhibit ACC, alter fatty acid biosynthesis or retard growth. The effects of the herbicide can be studied by measuring plant cell ACC activity, fatty acid synthesis or growth.

An effective herbicidal dose of a given herbicide is that amount of the herbicide that retards growth or kills plant cells not containing herbicide-resistant ACC or that amount of a herbicide known to inhibit plant growth. Means for determining an effective herbicidal dose of a given herbicide are well known in the art. Preferably, a herbicide used in such a process is an aryloxyphenoxypropionate or cyclohexanedione herbicide.

VI. Process of Altering ACC Activity

Acetyl-CoA carboxylase catalyzes the carboxylation of acetyl-CoA. Thus, the carboxylation of acetyl-CoA in a cyanobacterium or a plant can be altered by, for example, increasing an ACC gene copy number or changing the composition (e.g., nucleotide sequence) of an ACC gene. Changes in ACC gene composition can alter gene expression at either the transcriptional or translational level. Alternatively, changes in gene composition can alter ACC function (e.g., activity, binding) by changing primary, secondary or tertiary structure of the enzyme. By way of example, certain changes in ACC structure are associated with changes in the resistance of that altered ACC to herbicides. The copy number of such a gene can be increased by transforming a cyanobacterium or a plant cell with an appropriate expression vector comprising a DNA molecule that encodes ACC.

In one embodiment, therefore, the present invention contemplates a process of altering the carboxylation of acetyl-CoA in a cell comprising transforming the cell with a DNA molecule comprising a promoter operatively linked to a coding region that encodes a polypeptide having the ability to catalyze the carboxylation of acetyl-CoA, which coding region is operatively linked to a transcription-terminating region, whereby the promoter is capable of driving the transcription of the coding region in the cyanobacterium.

In a preferred embodiment, a cell is a cyanobacterium or a plant cell, a polypeptide is a cyanobacterial ACC or a plant ACC. Exemplary and preferred expression vectors for use in such a process are the same as set forth above.

Where a cyanobacterium is transformed with a plant ACC DNA molecule, that cyanobacterium can be used to identify herbicide resistant mutations in the gene encoding ACC. In accordance with such a use, the present invention provides a process for identifying herbicide resistant variants of a plant acetyl-CoA carboxylase comprising the steps of:

(a) transforming cyanobacteria with a DNA molecule that encodes a monocotyledonous plant acetyl-CoA carboxylase enzyme to form transformed or transfected cyanobacteria;

(b) inactivating cyanobacterial acetyl-CoA carboxylase;

(c) exposing the transformed cyanobacteria to an effective herbicidal amount of a herbicide that inhibits acetyl-CoA carboxylase activity;

(d) identifying transformed cyanobacteria that are resistant to the herbicide; and (e) characterizing DNA that encodes acetyl-CoA carboxylase from the cyanobacteria of step (d).

Means for transforming cyanobacteria as well as expression vectors used for such transformation are preferably the same as set forth above. In a preferred embodiment, cyanobacteria are transformed or transfected with an expression vector comprising an coding region that encodes wheat ACC.

Cyanobacteria resistant to the herbicide are identified. Identifying comprises growing or culturing transformed cells in the presence of the herbicide and recovering those cells that survive herbicide exposure.

Transformed, herbicide-resistant cells are then grown in culture, collected and total DNA extracted using standard techniques. ACC DNA is isolated, amplified if needed and then characterized by comparing that DNA with DNA from ACC known to be inhibited by that herbicide.

VII. Process for Determining Herbicide Resistance Inheritibility

In yet another aspect, the present invention provides a process for determining the inheritance of plant resistance to herbicides of the aryloxyphenocypropionate or cyclohexanedione class. That process comprises the steps of:

(a) measuring resistance to herbicides of the aryloxyphenocypropionate or cyclohexanedione class in a parental plant line and in progeny of the parental plant line to;

(b) purifying DNA from the parental plant line and the progeny;

(c) digesting the DNA with restriction enzymes to form DNA fragments;

(d) fractionating the fragments on a gel;

(e) transferring the fragments to a filter support;

(f) annealing the fragments with a labelled RFLP probe consisting of a DNA molecule that encodes acetyl-CoA carboxylase or a portion thereof;

(g) detecting the presence of complexes between the fragments and the RFLP probe; and (h) correlating the herbicide resistance of step (a) with the complexes of step (g) and thereby the inheritance of herbicide resistance.

In a preferred embodiment, the herbicide resistant variant of acetyl-CoA carboxylase is a dicotyledonous plant acetyl-CoA carboxylase enzyme or a portion thereof. In another preferred embodiment, the herbicide resistant variant of acetyl-CoA carboxylase is a mutated monocotyledonous plant acetyl-CoA carboxylase that confers herbicide resistance or a hybrid acetyl-CoA carboxylase comprising a portion of a dicotyledonous plant acetyl-CoA carboxylase, a portion of a dicotyledonous plant acetyl-CoA carboxylase or one or more domains of a cyanobacterial acetyl-CoA carboxylase.

The inheritibility of phenotypic traits such as herbicide resistance can be determined using RFLP analysis. Restriction fragment length polymorphisms (RFLPs) are due to sequence differences detectable by lengths of DNA fragments generated by digestion with restriction enzymes and typically revealed by agarose gel electrophoresis. There are large numbers of restriction endonucleases available, characterized by their recognition sequences and source.

Restriction fragment length polymorphism analyses are conducted, for example, by Native Plants Incorporated (NPI). This service is available to the public on a contractual basis. For this analysis, the genetic marker profile of the parental inbred lines is determined. If parental lines are essentially homozygous at all relevant loci (i.e., they should have only one allele at each locus), the diploid genetic marker profile of the hybrid offspring of the inbred parents should be the sum of those parents, e.g., if one parent had the allele A at a particular locus, and the other parent had B, the hybrid AB is by inference.

Probes capable of hybridizing to specific DNA segments under appropriate conditions are prepared using standard techniques well known to those skilled in the art. The probes are labelled with radioactive isotopes or fluorescent dyes for ease of detection. After restriction fragments are separated by size, they are identified by hybridization to the probe. Hybridization with a unique cloned sequence permits the identification of a specific chromosomal region (locus). Because all alleles at a locus are detectable, RFLP's are co-dominant alleles, thereby satisfying a criteria for a genetic marker. They differ from some other types of markers, e.g., from isozymes, in that they reflect the primary DNA sequence, they are not products of transcription or translation. Furthermore, different RFLP profiles result from different arrays of restriction endonucleases.

The foregoing examples illustrate particular embodiments of the present invention. It will be readily apparent to a skilled artisan that changes, modification and alterations can be made to those embodiments without departing from the true scope or spirit of the invention.

EXAMPLE 1

Isolation of Cyanobacterial ACC Polynucleotides

The polynucleotide of SEQ ID NO:1 contains a gene that encodes the enzyme biotin carboxylase (BC) enzyme from the cyanobacterium Anabaena 7120. This gene was cloned from a total DNA extract of Anabaena that was digested with various restriction enzymes, fractionated by gel electrophoresis, and blotted onto GeneScreen Plus (DuPont).

The blot was hybridized at low stringency (1M NaCl, 57° C.) with a probe consisting of a SstII-PstI fragment containing about 90% of the coding region of the fabG gene from *E. coli*. This probe identified a 3.1-kb HindIII fragment in the Anabaena digest that contained similar sequences. A mixture of about 3-kb HindIII fragments of Anabaena DNA was purified, then digested with NheI, yielding a HindIII-NheI fragment of 1.6 kb that hybridized with the fabG probe. The 1.6-kb region was purified by gel electrophoresis and cloned into pUC18. Plasmid minipreps were made from about 160 colonies, of which four were found to contain the 1.6-kb HindIII-NheI fragment that hybridized with the fabG probe. The 1.6-kb Anabaena fragment was then used as probe to screen, at high stringency (1M NaCl, 65° C.), a cosmid library of Anabaena DNA inserts averaging 40 kb in size. Five were found among 1920 tested, all of which contained the same size HindIII and NheI fragments as those identified by the *E. coli* probe previously. From one of the cosmids, the 3.1-kb HindIII fragment containing the Anabaena fabG gene was subcloned into pUC18 and sequenced using the dideoxy chain termination method. The complete nucleotide sequence of this fragment is shown in FIG. 1 (SEQ ID NO:1 and SEQ ID NO:2).

A similar procedure was used to clone the fabG gene from Synechococcus. In this case, the initial Southern hybridization showed that the desired sequences were contained in part on an 0.8-kb BamHI-PstI fragment. This size fragment was purified in two steps and cloned into the plasmid Bluescript KS. Minipreps of plasmids from 200 colonies revealed two that contained the appropriate fragment of Synechococcus DNA. This fragment was used to probe, at high stringency, a library of Synechococcus inserts in the cosmid vector pWB79. One positive clone was found among 1728 tested. This cosmid contained a 2-kb BamHI and a 3-kb PstI fragment that had previously been identified by the *E. coli* fabG probe in digests of total Synechococcus DNA. Both fragments were subcloned from the cosmid into Bluescript KS and 2.4 kb, including the coding part of the fabG gene, were sequenced. The complete sequence of the coding region of the Anacystis fabG gene is shown in FIG. 2 (SEQ ID NO:5 and SEQ ID NO:6).

EXAMPLE 2

Plant ACC

Figure 5:
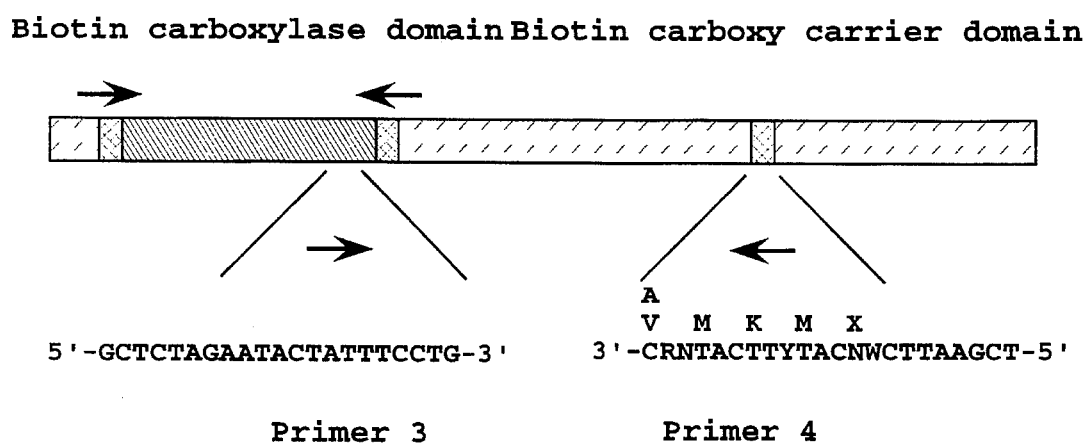
FIG. 5 shows the sequences of the oligonucleotides (SEQ ID NOS:114 and 115) used as primers for the PCR used to amplify the region of wheat ACC cDNA between the BC and BCCP domains.

The amino acid sequences of the fabG genes encoding BC from Anabaena and Synechococcus are aligned with sequences of ACC and other biotin-containing enzymes from several sources in FIG. 3. This comparison allows the designation of several areas of significant conservation among all the proteins, indicated by stars in the Figure. Based on this alignment, the sequences shown in FIG. 4 were chosen for the construction of primers for the polymerase chain reaction, in order to amplify the corresponding region of the gene for ACC from wheat. The primers used for this amplification are shown in FIG. 4. Each consists of a 14-nucleotide specific sequence based on the amino acid sequence and an 8-nucleotide extension at the 5'-end of the primer to provide anchors for rounds of amplification after the first round and to provide convenient restriction sites for future analysis and cloning.

cDNA amplification began with a preparation of total polyA-containing mRNA from eight day-old green plants (*Triticum aestivum* var. Era as described in [Lamppa, et al., 1992]). The first strand of cDNA was synthesized using random hexamers as primers for AMV reverse transcriptase following procedures described in [Haymerle, et al., 1986], with some modifications. Reverse transcriptase was inactivated by incubation at 90° C. and low molecular weight material was removed by filtration through centricon 100. All components of the PCR (from the Cetus/Perkin-Elmer kit) together with the two primers shown in FIG. 4, except the Taq DNA polymerase, were incubated for 3–5 min at 95° C. The PCR was initiated by the addition of polymerase. Conditions were established and optimized using Anabaena DNA as template, in order to provide the best yield and lowest level of non-specific products for amplification of the target BC gene from Anabaena DNA. Amplification was for 45 cycles, each 1 min at 95°, 1 min at 42°–46° and 2 min at 72° C. Both the reactions using Anabaena DNA and the single-stranded wheat cDNA as template yielded about 440-bp products. The wheat product was eluted from a gel and reamplified using the same primers. That product, also 440 bp, was cloned into the Invitrogen vector pCR1000 using their A/T tail method, and sequenced. The nucleotide sequence is shown in FIG. 5.

In eukaryotic ACCs, the BCCP domain is located about 300 amino acids away from the end of the BC domain, on the C-terminal side. Therefore, it is possible to amplify the cDNA covering that interval using primers from the C-terminal end of the BC domain and the conserved MKM region of the BCCP. The BC primer was based on the wheat cDNA sequence obtained as described above. These primers, each with 6- or 8-base 5'-extensions, are shown in FIG. 6B.

Figure 7:
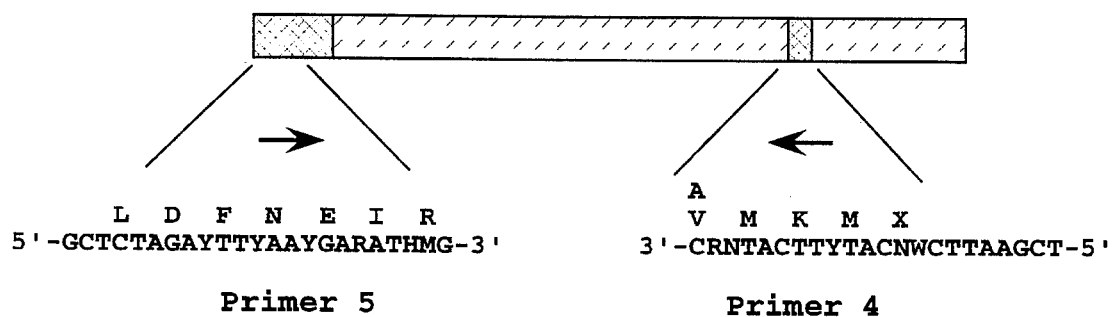
FIG. 7 shows the sequences (SEQ ID NOS:115 and 116) of the oligonucleotides used as primers to amplify most of the fabE gene encoding the biotin carboxyl carrier protein from DNA of Anabaena.

The MKM primer was first checked by determining whether it would amplify the fabE gene encoding BCCP from Anabaena DNA. This PCR was primed at the other end by using a primer based on the N-terminal amino acid sequence, determined on protein purified from Anabaena extracts by affinity chromatography, shown in FIG. 6A. This amplification (using the conditions described above) worked, yielding the correct fragment of the Anabaena fabE gene, whose complete sequence is shown in FIG. 7.

The PCR-amplified fragment of the Anabaena fabE gene was used to identify cosmids (three detected in a library of 1920) that contain the entire fabE gene and flanking DNA. A 4-kb XbaI fragment containing the gene was cloned into the vector Bluescript KS for sequencing. The two primers shown in FIG. 6 were then used to amplify the intervening sequence in wheat cDNA. Again, the product of the first PCR was eluted and reamplified by another round of PCR, then cloned into the Invitrogen vector pCRII. The complete 1.1 kb of the amplified DNA was sequenced, also shown in FIG. 5.

The foregoing examples illustrate particular embodiments of the present invention. One of ordinary skill in the art will readily appreciate that changes, modifications and alterations to those embodiments can be made without departing from the true scope or spirit of the invention.

REFERENCES

The references listed below and all references cited herein are incorporated herein by reference to the extent that they supplement, explain, provide a background for, or teach methodology, techniques, and/or compositions employed herein.

1. J. R. Knowles. 1989. The mechanism of biotin-dependent enzymes. Annu. Rev. Biochem. 58: 195–221.
Alix, J.-H. 1989. A rapid procedure for cloning genes from I libraries by complementation of *E. coli* defective mutants: application to the fabE region of the *E. coli* chromosome. DNA 8: 779–789.
3. Muramatsu, S., and T. Mizuno. 1989. Nucleotide sequence of the fabE gene and flanking regions containing a bent DNA sequence of *Escherichia coli*. Nucleic Acids Res. 17: 3982.
4. Li, S., and J. E. Cronan. 1992. The gene encoding the biotin carboxylase subunit of *Escherichia coli* acetyl-CoA carboxylase. J. Biol. Chem. 267: 855.
5. Lopez-Casillas, F., D. H. Bai, X. Luo, I. S. Kong, M. A. Hermodson, and K. H. Kim. 1988. Structure of the coding sequence and primary amino acid sequence of rat Acetylcoenzyme A carboxylase. Proc. Natl. Acad. Sci. USA 85: 5784–5788.
6. Takai, T., C. Yokoyama, K. Wada, and T. Tanabe. 1988. Primary structure of chicken liver acetyl-coenzyme A carboxylase deduced from cDNA sequence. J. Biol. Chem.: 2651–2657.
6a. W. A. Feel, S. S. Chirala and S. J. Wakil 1992. Cloning of the yeast FAS3 gene and primary structure of yeast acetyl-CoA carboxylase. Proc Natl Acad, Sci USA 89: 4534–4538.
7. J. L. Harwood. 1988. Fatty acid metabolism. Ann. Rev. Physiol. Plant Mol. Biol. 39: 101–138.
8. Egin-Buhler, B., and J. Ebel. 1983. Improved purification and further characterization of ACC from culture cells of parsley. Eur. J. Biochem. 133: 335–339.
9. Wurtele, E. S. and Nikolau, B. J. 1990. Arch. Biochem. Biophys. 278: 179–186.
10. Slabas, A. R. and Hellyer, A. 1985. Plant Sci. 39: 177–182.
11. Samols, D., C. G. Thornton, V. L. Murtif, G. K. Kumar, F. C. Haase, and H. G. Wood. 1988. Evolutionary conservation among biotin enzymes. J. Biol. Chem. 263: 6461–6464.
12. H. K. Lichtenthaler. 1990.Mode of action of herbicides affecting acetyl-CoA carboxylase and fatty acid biosynthesis. Z. Naturforsch. 45c: 521–528.
13. I. Pecker, D. Chamovitz, H. Linden, G. Sandmann and J. Hirschberg. 1992. A single polypeptide catalyzing the conversion of phytoene to z-carotene is transcriptionally regulated during tomato fruit ripening. Proc Natl Acad Sci USA 89: 4962–4666.
14. G. K. Lamppa, G. Morelli and N-H Chua (1985). Structure and developmental regulation of a wheat gene encoding the major chlorophyll a/b-binding polypeptide. Mol. Cell Biol. 5: 1370–1378.
15. H. Haymerle, J. Herz, G. M. Bressan, R. Frank and K. K. Stanley (1986). Efficient construction of cDNA libraries in plasmid expression vectors using an adaptor strategy. Nucl. Acids Res. 14: 8615–8629.
16. V. Vasil, A. M. Castillo, M. E. Fromm and I. K. Vasil (1992). Herbicide-resistant fertile transgenic wheat plants obtained by microprojectile bombardment of regenerable embryogenic callus. Biotechnology 10: 667–674.
17. S. S. Golden, T. Brusslen and R. Haselkorn (1987), Genetic Enginerring of the Cyanobacterial Chromosome. Methods Enzymology 153: 215–231.

What is claimed is:

1. An isolated and purified polynucleotide of from about 1350 to about 4000 base pairs that encodes a polypeptide that is a subunit of acetyl-CoA carboxylase, that possesses the ability to catalyze the carboxylation of a biotin carboxyl carrier protein of a cyanobacterium and hybridizes under low stringency conditions to a nucleotide sequence selected from the group consisting of SEQ ID NO:1 and SEQ ID NO:5.

2. The polynucleotide according to claim 1 wherein said cyanobacterium is Anabaena or Synechococcus.

3. The polynucleotide according to claim 2 wherein said biotin carboxyl carrier protein includes the amino acid residue sequence shown in SEQ ID NO:111.

4. The polynucleotide according to claim 1 wherein said polypeptide has the amino acid residue sequence of SEQ ID NO:3 or SEQ ID NO:6.

5. The polynucleotide according to claim 1 that includes (a) the DNA sequence of SEQ ID NO:1 from about nucleotide position 1300 to about nucleotide position 2650; (b) the DNA sequence of SEQ ID NO:1; or (c) the DNA sequence of SEQ ID NO:5.

6. An isolated and purified polynucleotide of from about 1500 to about 10,000 base pairs that encodes a polypeptide of a monocotyledonous or a dicotyledonous plant which hybridizes under low stringency conditions to the nucleotide sequence SEQ ID NO:108, wherein the polypeptide has the ability to catalyze the carboxylation of acetyl-CoA.

7. The polynucleotide according to claim 6 wherein said monocotyledonous plant is wheat, rice, maize, barley, rye, oats or timothy grass.

8. The polynucleotide according to claim 6 wherein said dicotyledonous plant is soybean, rape, sunflower, tobacco, Arabidopsis, petunia, canola, pea, bean, tomato, potato, lettuce, spinach, carrot, canola, alfalfa, or cotton.

9. The polynucleotide according to claim 6 wherein said polypeptide includes the amino acid residue sequence of SEQ ID NO:109.

\* \* \* \* \*